(12) United States Patent
Bergström

(10) Patent No.: US 6,610,838 B1
(45) Date of Patent: Aug. 26, 2003

(54) P13 ANTIGENS FROM BORRELIA

(75) Inventor: Sven Bergström, Umeå (SE)

(73) Assignee: Symbicom Aktiebolag, Amea (SE)

( * ) Notice: Subject to any disclaimer, the term of this patent is extended or adjusted under 35 U.S.C. 154(b) by 0 days.

(21) Appl. No.: 09/153,447

(22) Filed: Sep. 15, 1998

Related U.S. Application Data

(63) Continuation-in-part of application No. PCT/DK98/00379, filed on Sep. 4, 1998.
(60) Provisional application No. 60/059,036, filed on Sep. 16, 1997.

(30) Foreign Application Priority Data

Sep. 10, 1997 (DK) .............................................. 1041/97

(51) Int. Cl.[7] .......................... C07H 21/04; C07K 14/00
(52) U.S. Cl. ..................... 536/23.7; 536/73.1; 530/350; 530/387.1; 530/388.2
(58) Field of Search ..................... 424/184.1; 536/23.1; 576/23.7, 24.32, 24.33; 530/350, 387.1, 388.2

(56) References Cited

U.S. PATENT DOCUMENTS

| | | |
|---|---|---|
| 3,791,932 A | 2/1974 | Schurrs et al. |
| 3,949,064 A | 4/1976 | Bornstein et al. |
| 4,174,384 A | 11/1979 | Ullman et al. |

(List continued on next page.)

FOREIGN PATENT DOCUMENTS

| | | |
|---|---|---|
| EP | 0 036 776 B1 | 9/1981 |
| EP | 0 243 333 A2 | 10/1987 |
| EP | 0 366 238 | 5/1990 |
| EP | 054057 | 5/1993 |
| WO | WO 88/01875 | 3/1988 |
| WO | WO 90/04411 | 5/1990 |
| WO | WO 93/08299 | 4/1993 |
| WO | WO 95/12675 | 5/1995 |
| WO | WO 95/35119 | 12/1995 |

OTHER PUBLICATIONS

Feng, S. et al. "Characterization of two genes, p. 11 and p. 5, on the *Borrelia burgdorferi* 49–kilo base linear plasmid", Biochimica et Biophysica Acta, vol. 1307, No. 3, dated Jul. 17, 1996.

(List continued on next page.)

*Primary Examiner*—B. L. Sisson
(74) *Attorney, Agent, or Firm*—Frommer Lawrence & Haug LLP; William S. Frommer; Thomas J. Kowalski

(57) ABSTRACT

The invention relates to an isolated nucleic acid fragment which encodes a polypeptide fragment which exhibits a substantial immunological reactivity with a rabbit polyclonal antibody raised against a polypeptide having an apparent molecular weight of 13 kDa as determined by SDS-PAGE followed by visualization, said polypeptide being derived from *Borrelia burgdorferi* B313 and being encoded by the nucleotide sequence of SEQ ID NO: 18, said rabbit polyclonal antibody exhibiting substantially no immunological reactivity with proteins from at least 95% of spirochaetes randomly selected from the group consisting of *Borrelia hermsii, Borrelia crocidurae, Borrelia anserina,* and *Borrelia hispanica,* and/or hybridises readily under highly stringent hybridization conditions with a DNA fragment having a nucleotide sequence selected from the group consisting of SEQ ID NO: 18, SEQ ID NO: 20, and SEQ ID NO: 22, or with a DNA fragment complementary thereto, but exhibits no substantial hybridization when the hybridization conditions are highly stringent with genomic DNA from at least 95% of spirochaetes randomly selected from the group consisting of *Borrelia hermsii, Borrelia crocidurae, Borrelia anserina,* and *Borrelia hispanica.*

Figure 1A:
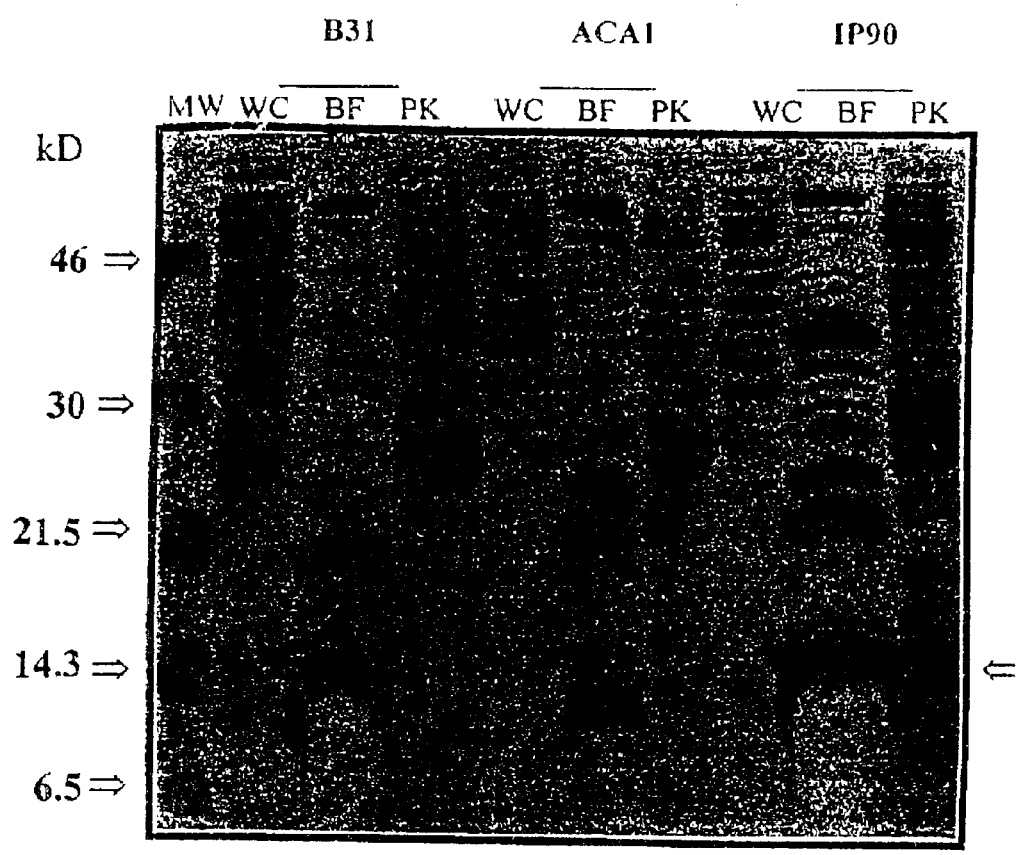

Furthermore, the invention relates to polypeptide fragments, vectors, transformed cells and cell lines, a method of preparing a polypeptide fragment and, vaccines as well as diagnostic compositions and kits.

38 Claims, 16 Drawing Sheets

U.S. PATENT DOCUMENTS

| | | | |
|---|---|---|---|
| 4,358,535 | A | 11/1982 | Falkow et al. |
| 4,554,101 | A | 11/1985 | Hopp |
| 4,578,770 | A | 3/1986 | Mitani |
| 4,596,792 | A | 6/1986 | Vyas |
| 4,599,230 | A | 7/1986 | Milich et al. |
| 4,599,231 | A | 7/1986 | Milich et al. |
| 4,601,903 | A | 7/1986 | Frasch |
| 4,603,102 | A | 7/1986 | Himmelmann et al. |
| 4,608,251 | A | 8/1986 | Mia |
| 5,411,732 | A | 5/1995 | Lowenadler et al. |

OTHER PUBLICATIONS

Fraser et al. Genomic sequence of a Lyme disease spirochete, *Borrelia burgdorferi*, EMBL Data Base Empro: AE00117, dated 1997.

Fraser et al. Genomic sequence of a Lyme disease spirochete, *Borrelia burgdorferi*, EMBL Data Base Empro: Pir:B70104, dated 1998.

U.S. Application Ser. No. 08/373,455 filed Jan. 17, 1995.

Wilske B, Preac–Mursic V, Jauris S, Hofman A, Pradel I, Soutschek E, Schwab E, Will G, Wanner G, 1993. Immunological and molecular polymorphisms of OspC, an immunodominant major outer surface protein of *Borrelia burgdorferi*. Infection and Immunity, 61:2182–2191.

Shanafelt MC, Hinderson P, Soderberg C, Mensi N, Turck CW, Webb D, Yssel H, Peltz G, 1991. T cell and antibody reactivity with the *Borrelia burgdorferi* 60–kDa heat shock protein in Lyme arthritis. Journal of Immunology, 146: 3985–3992.

Norton Hughes CA, Engstrom SM, Coleman LA, Kodner CB, Johnson RC., 1993. Protective immunity is induced by a *Borrelia burgdorferi* mutant that lacks OspA and OspB. Infection and Immunity, 61: 5115–5122.

Messing et al., 1981. Recombinant DNA, Third Cleaveland Symposium on Macromolecules, A.G. Walton, Elsevier Scientific Publishing Company, Amsterdam.

Adam T, Gassmann GS, Rasiah C. Göbel UB. 1991. Phenotypic and gentoypic analysis of *Borrelia burgdorferi* isolates from various sources. Infection and Immunity, 59: 2579–2585.

Adelman JP, Hayflick, JS, Vasser M, Seeburg PH. 1983. In vitro deletional mutagenesis for bacterial production of the 20,000–dalton form of human pituitary growth hormone. DNA. 2(3):183–93.

Anderson, JF, Magnarelli LA, McAnich JB. 1988. Journal of Clinical Microbiology, 26: 2209–2212.

Arimitsu Y, Takashima I, Yoshii Z, Higashi Y, Kameyama S, Mizuguchi J. 1991. Journal of Infectious Diseases, 163: 682–683.

Goeddel DV, Heyneker HL, Hozumi T, Arentzen R, Itakura K, Yanasura DG, Ross MJ, Miozzari G, Crea R, Seeburg PH. 1979, Direct expression in *Escherichiacoli* of a DNA sequence coding for human growth hormone. Nature. 281(5732):544–548.

Goodman JL, Jarkovich P, Kramber JM, Johnson RC. 1991. Molecular detection of persistent *Borrelia burgdorferi* in the urine of patients with active Lyme disease. Infection and Immunity, 59: 269–278.

**Grodzicki RL, Steere AC. 1988. Comparison of immunoblotting and indirect enzyme–linked immunosorbent assay using different antigen preparations for diagnosing early Lyme disease. Journal of Infectious Diseases, 157: 790–797.

Hess et al. 1968. Advances in Enzyme Regulation, 7: 149–166.

Hitzeman RA, Clarke L, Carbon J. 1980. Isolation and characterization of the yeast 3–phosphoglycerokinase gene (PGK) by an immunological screeningtechnique. Journal of Biological Chemistry. 255(24):12073–12080.

Holland MJ, Holland JP. 1978. Isolation and identification of yeast messenger ribonucleic acids coding for enolase, glyceraldehyde–3–phosphate dehydrogenase,and phosphoglycerate kinase. Biochemistry. 17(23):4900–4907.

Honavar N, Schaible UE, Galanos C, Wallich R ansd Simon MM, 1994. A 14,000 MW lipoprotein and a glycolipid–like structure of *Borrelia burgdorferi* induce proliferation and immunoglobulin production in mouse B cells at high frequencies. Immunology 82: 389–396.

Hopp TP, Woods KR. 1981. Proceedings of the National Academy of Sciences USA, 78:3824–3828.

Itakura K, Hirose T, Crea R, Riggs, AD, Heyneker HL, Bolivar F, Boyer HW. 1977. Expression in *Escherichia coli* of a chemically synthesized gene for the hormone somatostatin. Science. 198(4321):1056–63.

Jameson BA, Wolf H. 1988. Computer Applications in the biosciences, 4:181–186.

Jones EW. 1977. Proteinase mutants of *Saccharomyces cerevisiae*. Genetics, 85(1):23–33.

Jonsson M, Noppa L, Barbour AG, Bergström S. 1992. Heterogeneity of outer membrane proteins in *Borrelia burgdorferi*: comparison of osp operons of three isolates of different geographic origins. Infection and Immunity.

Katona LI, Beck G and Habicht GS. 1992. Purification and immunological characterization of a major low–molecular–weight lipoprotein from *Borrelia burgdorferi* Infect. Immun., 60: 4995–5003.

Kingsman AJ, Clarke L, Mortimer RK, Carbon J. 1979. Replication in *Saccharomyces cerevisiae* of plasmid pBR313 carrying DNA from the Yeast trpl region. Gene. 7(2):141–52.

Kryuchechnikov VN, Korenberg EI, Scherbakov SV, Kovalevsky YV, Levin ML. 1988. Identification of Borrelia isolated in the USSR from *Ixodes persulcatus schulze* ticks. Journal of Microbiology, Epidemiology and Immunobiology, 12: 41–44 (this reference is in Russian. Please note the English language abstract and advise, if a full translation is needed).

Kyte J, Doolittle RF. 1982. Journal of Molecular Biology, 157:105–132.

Laemmli UK. 1970. Nature 227:680–685.

Lebech AM, Hindersson P, Vuust J, Hansen KJ. 1991. Comparison of in vitro culture and polymerase chain reaction for detection of *Borrelia burgdorferi* in tissue from experimentally infected animals. Journal of Clinical Microbiology, 29: 731–737.

**Luft BJ, Jiang W, Munoz P, Dattwyler RJ Gorevic PD. 1989. Biochemical and immunological characterization of the surface proteins of *Borrelia burgdorferi*. Infection and Immunity, 57: 3637–3645.

Luke CJ, Carner K, Liang X, Barbour AG. 1997. An OspA–based DNA Vaccine protects mice against infection with *Borrelia burgdorferi*. The Journal of Infectious Diseases, 175:91–97.

**Löwenadler B, Jansson B, Paleus S, Holmgren E, Nilsson B, Moks T, Palm G, Josephson S, Philipson L, Uhlén M. 1987. A gene fusion system for generating antibodies against short peptides. Gene, 58: 87–97.

\*\*Ma B, Christen B, Leung D, Vigo–Pelfrey C. 1992. Serodiagnosis of Lyme borreliosis by Western immunoblot: reactivity of various significant antibodies against *Borrelia burgdorferi*. Journal of Clinical Microbiology, 30: 370–376.

Magnarelli LA., Anderson JF, Barbour AG. 1989. Enzyme–linked immunosorbent assays for Lyme disease: reactivity of subunits of *Borrelia burgdorferi*. Cross–reactivity in serologic tests for Lyme disease and other spirochetal infections. Journal of Infectious Diseases, 159: 43–49.

\*\*Magnarelli LA., Anderson JF, Johnson RC. 1987. Cross–reactivity in serologic tests for Lyme disease and other spirochetal infections. Journal of Infectious Diseases, 156: 183–188.

\*\*Magnarelli LA., Miller JN, Anderson JF, Riviere GR. 1990. Cross–reactivity of nonspecific treponemal antibody in serologic tests of Lyme disease. Journal of Clinical Microbiology, 28: 1276–1279.

Marconi RT, Garon CF. 1992. Phylogenetic analysis of the genus Borrelia: a comparison of North American and European isolates of *Borrelia burgdorferi*. Journal of Bacteriology, 174: 241–244.

Marconi RT, Konkel ME, Garon CF. 1993. Variability of osp genes and gene products among species of Lyme disease spirochetes. Infection and Immunity, 61: 2611–2617.

Marconi RT, Samuels DS, Schwan TG, Garon CF. 1993. Identification of a protein in several Borrelia species which is related to OspC of Lyme disease spirochetes. Journal of Clinical Microbiology, 31: 2577–2583.

Matsudaira P. 1987. Sequence from picomole quantities of proteins electroblotted onto polyvinylidene difluoride membranes. Journal of Biological Chemistry, 262: 10035–10038.

\*\*\*Messing et al. 1981, Third Cleveland Symposium on Macromolecules and Recombinant DNA, Ed. A Walton, Elsevier, Amsterdam.

Nielsen P E et al., 1991, Science 254: 1497–1500.

Norris SJ, Carter CJ, Howell JK, Barbour AG. 1992. Low–passage–associated proteins of *Borrelia burgdorferi* B31: Characterization and molecular cloning of OspD, a surface exposed, plasmid–encoded lipoprotein. Infection and Immunity, 60: 4662–4672.

\*\*\* Norton Hughes CA, Engstrom SM, Coleman LA, Kodner CB, Johnson RC. 1993. Protective immunity is induced by a *Borrelia burgdorferi* mutant that lacks OspA and OspB. Infection and Immunity, 61: 5115–5122.

Olsén B. Jaenson TGT, Noppa L, Bunikis J, Bergstroöm S. 1993. A Lyme borreliosis cycle in seabirds and *Ixodes uriae* ticks. Nature, 362: 340–342.

Porcella SF; Popova TG, Akins DR, Li M, Radolf JD, Norgard MV. 1996. *Borrelia burgdorferi* supercoiled plasmids encode multicopy tandem reading frames and a lipoprotein gene family. Journal of Bacteriology. 178: 3293–3307.

\*\*Preac–Mursic V, Wilske B, Patsouris E, Jauris S, Will G, Soutschek E, Reinhardt S, Lehnert G, Klockmann U, Mehraein P. 1992. Active immunization with pC protein of *Borrelia burgdorferi* protects gerbils against *Borrelia burgdorferi* infection. Infection, 20: 342–349.

\*\*Raoult D, Hechemy KE, Baranton G. 1989. Crossreaction with *Borrelia burgdorferi* antigen of sera from patients with human immunodeficiency virus infection, syphilis, and leptospirosis. Journal of Clinical Microbiology, 27: 2152–2155.

Rhan DW, Malavista SE. 1991. Annals of Internal Medicine, 114: 472–481.

\*Remington: The Science and Practice of Pharmacy, 19$^{th}$ ed., Gennaro, AR, 1995 (this is a general textbook and need not, in our opinion, be filed with the USPTO).

Šadziene A, Thompson PA, Barbour AG. 1993. In vitro inhibition of *Borrelia burgdorferi* growth by antibodies. Journal of Infectious Diseases, 167: 165–172.

Šadziene A, Thomas DD and Barbour AG. 1994. *Borrelia burgdorferi* mutant lacking Osp: Biological and immunological characterization. Infection and Immunity, 63: 1573–1580.

Sambri V, Moroni A, Massaria F, Brocchi E, De Simone F and Cevenini R. 1991. Immunological characterization of a low molecular mass polypeptide antigen of *Borrelia burgdorferi*. FEMS Microb. Immunol. 76: 345–350.

Sambrook J, Fritsch EF, Maniatis T. 1989. Molecular cloning: a laboratory manual 2nd ed. Cold Spring Harbor Laboratory, Cold Spring Harbor, N.Y.

Schaible UE, Kramer MD, Eichmann K, Modolell M, Museteanu C, Simon MM. 1990. Monoclonal antibodies specific for the outer surface protein A (OspA) of *Borrelia burgdorferi* prevent Lyme borreliosis in severe combined immunodeficiency (scid) mice. Proceedings of the National Academy of Sciences.

Baranton G, Postic D, Saint Girons I, Boerlin P, Piffaretti J–C, Assous M, Grimont PAD. 1992. Delineation of *Borrelia burgdorferi* sensu stricto, *Borrelia garinii* sp. nov., and group VS461 associated with Lyme borreliosis. International Journal of Systematic Bacteriology, 42: 378–383.

\*\*Barbour AG, Burgdorfer W, Grunwaldt E, Steere AC. 1983. Antibodies of patients with Lyme disease to components of the *Ixodes damini* spirochete. Journal of Clinical Investigation, 72: 504–515.

Barbour AG, Tessier SL, Hayes SF. 1984. Variation in a major surface protein of Lyme disease spirochetes. Infection and Immunity, 45: 94–100.

Barbour AG. 1984. Immunochemical analysis of Lyme disease spirochetes. The Yale Journal of Biology and Medicine, 57: 581–586.

Barbour AG. 1986. Polymorphisms of major surface proteins of *Borrelia burgdorferi*. Zbl Bakt Hyg, 263: 83–91.

Barbour AG. 1988. Laboratory aspects of Lyme borreliosis Clinical Microbiology Reviews, 1: 399–414.

Barthold SW, Bockenstedt LK. 1993. Passive immunising activity of sera from mice infected with *Borrelia burgdorferi*. Infection and Immunity, 61: 4696–4702.

Bergström S, Sjöstedt A, Dotevall L, Kaijser B, Ekstrand–Hammarstroöm B, Wallberg C, Skogman G, Barbour AG. 1991. Diagnosis of Lyme borreliosis by an enzyme immunoassay detecting immunoglobulin G reactive to purified *Borrelia burgdorferi* cell components. European Journal of Clinical Microbiology and Infectious Diseases, 10: 422–427.

Beaucage SL, Caruthers MM et al. 1981. Tetrahedron Letters, 22: 1859–1862.

Bolivar F, Rodriguez RL, Greene PJ, Betlach MC, Heyneker HL, Boyer HW. 1977. Construction and characterization of new cloning vehicles. II. A multipurpose cloning system. Gene, 2: 95–113.

\*\*Bruckbauer HR, Preac–Mursic V, Fuchs R, Wilske B. 1992. Cross reactive proteins of *Borrelia burgdorferi*. European Journal of Clinical Microbiology and Infectious Diseases, 3: 224–232.

Burgdorfer W, Barbour AG, Hayes SF, Benach JL, Grunwaldt E, Davis JP. 1983 Lyme disease –a tick borne spirochetosis.

Burman N, Bergström S, Restrepo BI, Barbour AG. 1990. The variable antigens Vmp7 and Vmp21 of the relapsing fever bacterium Borrelia hermsii are structurally analogous to the VSG proteins of the African trypanosome. Molecular Microbiology, 4: 1715–1726.

Canica MM, Nato F, duMerle L, Mazie JC, Baranton G, Postic D. 1993. Monoclonal antibodies for identification of Borrelia afzelii sp. Nov. associated with late cutaneous manifestations of Lyme borreliosis. Scandinavian Journal of Infectious Diseases, 25: 441–448.

Chang AC, Nunberg JH, Kaufman RJ, Erlich HA, Schimke RT, Cohen SN. 1978. Phenotypic expression in E. coli of a DNA sequence coding for mousedihydrofolate reductase. Nature. 275(5681):617–624,.

**Coleman JL, Benach JL. 1987. Isolation of antigenic components from the Lyme disease spirochete: their role in early diagnosis. Journal of Infectious Diseases, 155: 756–765.

Craft JE, Grodzicki RL, Steere AC. 1984. Antibody response in Lyme disease: evaluation of diagnostic tests. Journal of Infectious Diseases, 149: 789–795.

Crea R, Kraszewski A, Hirose T, Itakura K. 1978. Chemical synthesis of genes for human insulin. Proceedings of the National Academy of Sciences USA. 75(12):5765–5769.

**Dressler F, Whalen JA, Reinhardt BN, Steere AC. 1993. Western blotting in the serodiagnosis of Lyme disease. The Journal of Infectious Diseases, 167: 392–400.

Eichenlaub R. 1979. Mutants of the mini–F plasmid pML31 thermosensitive in replication. Journal of Bacteriology, 138: 559–566.

Erdile LF, Brandt M–N, Warakomski DJ, Westrack GJ, Sadziene A, Barbour AG, Mays JP. 1993. Role of attached lipid in immunogenicity of Borrelia burgdorferi OspA. Infection and Immunity, 61: 81–90.

Ferdows MS, Barbour AG. 1989. Megabase–sized linear DNA in the bacterium Borrelia burgdorferi, the Lyme disease agent. Proceedings of National Academy of Science, 86: 5969–5973.

Fiers W, Contreras R, Haegemann G, Rogiers R, Van de Voorde A, Van Heuverswyn H, Van Herreweghe J, Volckaert G, Ysebaert M. 1978. Complete nucleotide sequence of SV40 DNA. Nature. 273(5658):113–120.

Fikrig E, Barthold SW, Marcantonio N, DePonte K, Kantor FS, Flavell RA. 1992. Roles of OspA, OspB, and flagellin in protective immunity to Lyme borreliosis in laboratory mice. Infection and Immunity, 60: 657.

*Fraser CM, Casjens S, Huang WM, Sutton GG, Clayton R, Lathigra R, White O, Ketchum KA, Dodson R, Hikey EK, Gwinn M, Doughery B, Tomb JF, Fleischmann RD, Richardson D, Peterson J, Kervalage AR, Quackenbush J, Salzberg S, Hanson M, van Vugt R, Palmer N, Adams MD, Gocayne J, Venter JC et al., 1997. Genomic sequence of a Lyme diseases spirochaete, Borrelia burgdorferi. Nature, 390: 580–586.

**Gassmann GS, Jacobs E, Deutzmann R, Göbel UE. 1991. Analysis of fla gene of Borrelia burgdorferi GeHo and antigenic characterization of its gene product. Journal of Bacteriology, 173: 1452–1459.

Schmid GP. 1985. Reviews of infectious diseases, 7: 41–49.

***Shanafelt MC, Hinderson P, Soderberg C, Mensi N, Turck CW, Webb D, Yssel H, Peltz G. 1991. T cell and antibody reactivity with the Borrelia burgdorferi 60–kDa heat shock protein in Lyme arthritis. Journal of Immunology, 146: 3985–3992.

Siebenlist U, Simpson RB, Gilbert W. 1980. E. coli RNA polymerase interacts homologously with two different promoters. Cell. 20(2):269–281.

**Simpson WJ, Schrumpf ME, Schwan TG. 1990. Reactivity of human Lyme borreliosis sera with a 39–kilodalton antigen specific to Borrelia burgdorferi. Journal of Clinical Microbiology, 28: 1329–1337.

Steere AC, Malavista SE, Syndman DR. 1977. Arthritis and reuhmatism, 20: 7–17.

Steere AC, Taylor E, Wilson ML, Levine JF, Spielman A. 1986. Journal of Infectious Diseases, 154: 295–300.

Steere AC. 1989. Lyme disease. New England Journal of Medicine, 321: 586–596.

Stinchcomb DT, Struhl K, Davis RW. 1979. Isolation and characterisation of a yeast chromosomal replicator. Nature. 282(5734):39–43.

Telford SR, Fikrig E, Barthold SW, Rosa Brunet L, Spielman A, Flavell RA. 1993. Protection aganist antigenically variable Borrelia burgdorferi conferred by recombinant vaccines. Journal of Experimental Medicine, 178: 755–758.

**Theisen M, Frederiksen B, Lebech A–M, Vuust J, Hansen K. 1993. Polymorphism in ospC gene of Borrelia burgdorferi and immunoreactivity of OspC protein: implications for taxonomy and for use of OspC protein as a diagnostic antigen. Journal of Clinical Microbiology, 31: 2570–2576.

Tschumper G, Carbon J. 1980. Sequence of a yeast DNA fragment containing a chromosomal replicator and the TRP1 gene. Gene. 10(2):157–66.

Ulmer JB, Donnelly JJ, Parker SE, Rhodes GH, Felgner PL, Dwarki VJ, Gromkowski SH, Deck RR, DeWitt CM, Friedman A. et al. 1993. Heterologous protection against influenza by injection of DNA encoding a viral protein. Science. 259(5102):1745–1749.

*von Heijne G. 1986. A new method for predicting signal sequences cleavage sites. Nucleic Acid Research, 11: 4683–4690.

Wallich R, Moter SE, Simon MM, Ebnet K, Heiberger A, Kramer MD. 1990. The Borrelia burgdorferi flagellum–associated 41–kilodalton antigen (flagellin): molecular cloning, expression, and amplification of the gene. Infection and Immunity, 58: 1711–1719.

***Wilske B, Preac–Mursic V, Jauris S, Hofman A, Pradel I, Soutschek E, Schwab E, Will G, Wanner G. 1993. Immunological and molecular polymorphisms of OspC, an immunodominant major outer surface protein of Borrelia burgdorferi. Infection and Immunity, 61: 2182–2191.

**Wilske B, Preac–Mursic V, Schierz G, Busch KV. 1986. Immunochemical and immunological analysis of European Borrelia burgdorferi strains. Zbl Bakt Hyg, 263: 92–102.

Zingg BC, Anderson JF, Johnson RC, LeFebvre RB. 1993. Comparative analysis of genetic variability among Borrelia burgdorferi isolates from Europe and the United States by restriction enzyme analysis, gene restriction fragment length polymorphism, and pulse–field gel electrophoresis. Journal of Clinical Microbiology, 31: 3115–3122.

Åsbrink E, Hovmark A, Hederstedt B. 1984. The spirochetal etiology of acrodermatitis chronica atrophicans Herxheimer. Acta Dermatologica et Venereologica, 64: 506–512.

Fig. 2A

Fig. 2B

*B. burgdorferi* B313 pLY-H

SEQUENCE LISTING

<160> NUMBER OF SEQ ID NOS: 31

<210> SEQ ID NO 1
<211> LENGTH: 25
<212> TYPE: PRT
<213> ORGANISM: Borrelia burgdorferi

<400> SEQUENCE: 1

Thr Ser Lys Gln Asp Pro Ile Val Pro Phe Leu Leu Asn Leu Phe Leu
 1               5                  10                  15

Gly Phe Gly Ile Gly Ser Phe Ala Gln
            20                  25

<210> SEQ ID NO 2
<211> LENGTH: 20
<212> TYPE: DNA
<213> ORGANISM: Borrelia burgdorferi
<220> FEATURE:
<221> NAME/KEY: variation
<222> LOCATION: (1)..(20)
<223> OTHER INFORMATION: N stands for any nucleic acid
<220> FEATURE:
<221> NAME/KEY: variation
<222> LOCATION: (1)..(20)
<223> OTHER INFORMATION: R stands for G or A
<220> FEATURE:
<221> NAME/KEY: variation
<222> LOCATION: (1)..(20)
<223> OTHER INFORMATION: Y stands for T/U or C

<400> SEQUENCE: 2
acntcnaarc argayccnat                                           20

<210> SEQ ID NO 3
<211> LENGTH: 20
<212> TYPE: DNA
<213> ORGANISM: Borrelia burgdorferi
<220> FEATURE:
<221> NAME/KEY: variation
<222> LOCATION: (1)..(20)
<223> OTHER INFORMATION: N stands for any nucleic acid
<220> FEATURE:
<221> NAME/KEY: variation
<222> LOCATION: (1)..(20)
<223> OTHER INFORMATION: R stands for G or A
<220> FEATURE:
<221> NAME/KEY: variation
<222> LOCATION: (1)..(20)
<223> OTHER INFORMATION: D stands for A or G or T/U

<400> SEQUENCE: 3
tgngcraarc tnccdatncc                                           20

<210> SEQ ID NO 4
<211> LENGTH: 74
<212> TYPE: DNA
<213> ORGANISM: Borrelia burgdorferi

<400> SEQUENCE: 4

-continued acatctaagc aggaccctat tgtaccatct ttattgaacc ttttttagg gtttggcatc    60 gggagcttcg ccca    74

<210> SEQ ID NO 5
<211> LENGTH: 34
<212> TYPE: DNA
<213> ORGANISM: Borrelia burgdorferi

<400> SEQUENCE: 5
tgtaccatct ttattgaacc ttttttagg gttt    34

<210> SEQ ID NO 6
<211> LENGTH: 26
<212> TYPE: DNA
<213> ORGANISM: Borrelia burgdorferi

<400> SEQUENCE: 6
aaaccctaaa aaaggttca ataaag    26

<210> SEQ ID NO 7
<211> LENGTH: 26
<212> TYPE: DNA
<213> ORGANISM: Borrelia burgdorferi

<400> SEQUENCE: 7
gatttttcat tggatcccag aatttg    26

<210> SEQ ID NO 8
<211> LENGTH: 26
<212> TYPE: DNA
<213> ORGANISM: Borrelia burgdorferi

<400> SEQUENCE: 8
ctataccaac cgaattcaaa tccaag    26

<210> SEQ ID NO 9
<211> LENGTH: 21
<212> TYPE: DNA
<213> ORGANISM: Borrelia burgdorferi

<400> SEQUENCE: 9 ggttttatg gatccacttt t    21

<210> SEQ ID NO 10
<211> LENGTH: 25
<212> TYPE: DNA
<213> ORGANISM: Borrelia burgdorferi

<400> SEQUENCE: 10
tatgctacca tggatccagt tttaa    25

<210> SEQ ID NO 11
<211> LENGTH: 31
<212> TYPE: DNA
<213> ORGANISM: Borrelia burgdorferi

<400> SEQUENCE: 11
cgggatccgt tttttctagc tttgctcaag c    31

<210> SEQ ID NO 12
<211> LENGTH: 50
<212> TYPE: DNA
<213> ORGANISM: Borrelia burgdorferi

<400> SEQUENCE: 12
ggaattccct ggttccgcgt ggatccatga ataaactttt aatttttgtt    50

<210> SEQ ID NO 13
<211> LENGTH: 25
<212> TYPE: DNA
<213> ORGANISM: Borrelia burgdorferi

<400> SEQUENCE: 13
taaaaaaatt taaagaaaag gaggg    25

<210> SEQ ID NO 14
<211> LENGTH: 27
<212> TYPE: DNA
<213> ORGANISM: Borrelia burgdorferi

<400> SEQUENCE: 14
ggcttataga atccggggct tatttgg    27

<210> SEQ ID NO 15
<211> LENGTH: 24
<212> TYPE: DNA
<213> ORGANISM: Borrelia burgdorferi

<400> SEQUENCE: 15
tagaattcag caattgcaat acag    24

<210> SEQ ID NO 16
<211> LENGTH: 32
<212> TYPE: DNA
<213> ORGANISM: Borrelia burgdorferi

<400> SEQUENCE: 16
cacccatttt ctagataaat aaaattaata gc    32

<210> SEQ ID NO 17
<211> LENGTH: 33
<212> TYPE: DNA
<213> ORGANISM: Borrelia burgdorferi

<400> SEQUENCE: 17 ataaaggta ccatagcttt ttttgaaaga cag    33

<210> SEQ ID NO 18
<211> LENGTH: 759
<212> TYPE: DNA
<213> ORGANISM: Borrelia burgdorferi
<220> FEATURE:
<221> NAME/KEY: CDS
<222> LOCATION: (170)..(709)

<400> SEQUENCE: 18
attgttaaaa gaattgaaat tgataatttt atggtcaaat caagaagctc tattgggaag    60
cgaatttcaa gcaataattt gaaaaaagtt aaatttaaat aactttaaaa acctttttta    120
aatttcatta atatgctacc atagtaccag ttttaataaa gggttttt atg aat aaa    178
                                                     Met Asn Lys
                                                      1 ctt tta att ttt gtt ttg gca acc ttt tgt gtt ttt tct agc ttt gct    226
Leu Leu Ile Phe Val Leu Ala Thr Phe Cys Val Phe Ser Ser Phe Ala
         5                  10                  15 caa gct aat gat tct aaa aat ggt gcg ttt ggg atg agt gct gga gaa    274

```
Gln Ala Asn Asp Ser Lys Asn Gly Ala Phe Gly Met Ser Ala Gly Glu
         20                  25                  30                  35 aaa ctt ttg gtt tat gaa act agc aag caa gat cct att gta cca ttt        322
Lys Leu Leu Val Tyr Glu Thr Ser Lys Gln Asp Pro Ile Val Pro Phe
             40                  45                  50 tta ttg aac ctt ttt tta ggg ttt gga ata ggc tcc ttt gct caa gga        370
Leu Leu Asn Leu Phe Leu Gly Phe Gly Ile Gly Ser Phe Ala Gln Gly
                 55                  60                  65 gat att ctt gga ggt tct ctt att ctt gga ttt gat gcg gtt ggt ata        418
Asp Ile Leu Gly Gly Ser Leu Ile Leu Gly Phe Asp Ala Val Gly Ile
         70                  75                  80 ggg ctt ata ctt gcg ggg gct tat ttg gat atc aaa gcg ctt gat ggt        466
Gly Leu Ile Leu Ala Gly Ala Tyr Leu Asp Ile Lys Ala Leu Asp Gly
     85                  90                  95 att act aaa aaa gct gct ttt caa tgg act tgg ggt aag gga gtt atg        514
Ile Thr Lys Lys Ala Ala Phe Gln Trp Thr Trp Gly Lys Gly Val Met
100                 105                 110                 115 tta gca ggt gtg gtt act atg gct gtg aca aga tta aca gaa att att        562
Leu Ala Gly Val Val Thr Met Ala Val Thr Arg Leu Thr Glu Ile Ile
                120                 125                 130 ctt cca ttt aca ttt gct aat agt tat aat agg aag cta aaa aat agc        610
Leu Pro Phe Thr Phe Ala Asn Ser Tyr Asn Arg Lys Leu Lys Asn Ser
            135                 140                 145 ctt aat gta gct tta gga gga ttt gaa cct agt ttt gat gtt gca atg        658
Leu Asn Val Ala Leu Gly Gly Phe Glu Pro Ser Phe Asp Val Ala Met
        150                 155                 160 ggc caa tcc agt gct ctt ggg ttt gaa ctg tct ttc aaa aaa agc tat        706
Gly Gln Ser Ser Ala Leu Gly Phe Glu Leu Ser Phe Lys Lys Ser Tyr
    165                 170                 175 taa ttttatttat tacaaaaatg ggtgattgca attctgtatt gaaatgggtg             759

<210> SEQ ID NO 19
<211> LENGTH: 179
<212> TYPE: PRT
<213> ORGANISM: Borrelia burgdorferi

<400> SEQUENCE: 19

Met Asn Lys Leu Leu Ile Phe Val Leu Ala Thr Phe Cys Val Phe Ser
  1               5                  10                  15

Ser Phe Ala Gln Ala Asn Asp Ser Lys Asn Gly Ala Phe Gly Met Ser
                 20                  25                  30

Ala Gly Glu Lys Leu Leu Val Tyr Glu Thr Ser Lys Gln Asp Pro Ile
             35                  40                  45

Val Pro Phe Leu Leu Asn Leu Phe Leu Gly Phe Gly Ile Gly Ser Phe
         50                  55                  60

Ala Gln Gly Asp Ile Leu Gly Gly Ser Leu Ile Leu Gly Phe Asp Ala
 65                  70                  75                  80

Val Gly Ile Gly Leu Ile Leu Ala Gly Ala Tyr Leu Asp Ile Lys Ala
                 85                  90                  95

Leu Asp Gly Ile Thr Lys Lys Ala Ala Phe Gln Trp Thr Trp Gly Lys
            100                 105                 110

Gly Val Met Leu Ala Gly Val Val Thr Met Ala Val Thr Arg Leu Thr
        115                 120                 125

Glu Ile Ile Leu Pro Phe Thr Phe Ala Asn Ser Tyr Asn Arg Lys Leu
    130                 135                 140

Lys Asn Ser Leu Asn Val Ala Leu Gly Gly Phe Glu Pro Ser Phe Asp
145                 150                 155                 160
```

-continued

```
Val Ala Met Gly Gln Ser Ser Ala Leu Gly Phe Glu Leu Ser Phe Lys
            165                 170                 175

Lys Ser Tyr

<210> SEQ ID NO 20
<211> LENGTH: 862
<212> TYPE: DNA
<213> ORGANISM: Borrelia afzelii
<220> FEATURE:
<221> NAME/KEY: CDS
<222> LOCATION: (219)..(755)

<400> SEQUENCE: 20
gatttttcat tggatcccag aatttgtaga attttcgaca aataaagaca ttattaaaag      60
aattgaaatt gctaattta tggtcaaatc aagaagctct attgggaagc gaatttcaag     120
taatactttg aaaaagtta aatttaaata gttttaaaaa cctttttta atttcattaa      180 tatgttacta ataccagt tttaataaag aggtttttt atg aat aaa ttt tta att    236
                                          Met Asn Lys Phe Leu Ile
                                            1               5 gtt gtt ttg cta gcc ttt tgt gtt ttt tct agc ttt gct caa gct gat    284
Val Val Leu Leu Ala Phe Cys Val Phe Ser Ser Phe Ala Gln Ala Asp
         10                  15                  20 gat tct aaa agc gct ttt aat ttg gga gcg gga gaa aaa ctt tta gct    332
Asp Ser Lys Ser Ala Phe Asn Leu Gly Ala Gly Glu Lys Leu Leu Ala
     25                  30                  35 tat gaa act agt aag aaa gat cct att gtg cca ttt tta ttg aac ctt    380
Tyr Glu Thr Ser Lys Lys Asp Pro Ile Val Pro Phe Leu Leu Asn Leu
 40                  45                  50 ttt tta ggg ttt gga ata ggt tct ttt gct caa gga gat att ctt ggg    428
Phe Leu Gly Phe Gly Ile Gly Ser Phe Ala Gln Gly Asp Ile Leu Gly
 55                  60                  65                  70 ggt ttt ctt att ctt gga ttt gat gca gtt ggt ata ggg tta ata ctt    476
Gly Phe Leu Ile Leu Gly Phe Asp Ala Val Gly Ile Gly Leu Ile Leu
             75                  80                  85 aca gga gct tat tta gat atc aaa gct ctt gat aag aat gct cca aaa    524
Thr Gly Ala Tyr Leu Asp Ile Lys Ala Leu Asp Lys Asn Ala Pro Lys
         90                  95                 100 gcc gct ttt aag tgg act tgg ggt aag gga atg atg ttg gca ggt gca    572
Ala Ala Phe Lys Trp Thr Trp Gly Lys Gly Met Met Leu Ala Gly Ala
     105                 110                 115 gtt act atg gct gtg aca aga ttg aca gaa att att att ccg ttt aca    620
Val Thr Met Ala Val Thr Arg Leu Thr Glu Ile Ile Ile Pro Phe Thr
 120                 125                 130 ttt gct aat agt tat aat agg aaa ctg aaa aat agc ctt aat ata gct    668
Phe Ala Asn Ser Tyr Asn Arg Lys Leu Lys Asn Ser Leu Asn Ile Ala
135                 140                 145                 150 ttt gga ggg ttt gag cct agt ttt gat att aat atg ggc caa gct agc    716
Phe Gly Gly Phe Glu Pro Ser Phe Asp Ile Asn Met Gly Gln Ala Ser
             155                 160                 165 gct ctt ggg ttt gaa cta tct ttc aaa aaa agt tat taa ttttatttta    765
Ala Leu Gly Phe Glu Leu Ser Phe Lys Lys Ser Tyr
         170                 175 ttattaaaat gagtgatagc aattttgtat tgtgattgct cattgtaatt gaaaattaga    825
gcttttgttt attatttata ttttatttct ctgctaa                              862

<210> SEQ ID NO 21
<211> LENGTH: 178
<212> TYPE: PRT
<213> ORGANISM: Borrelia afzelii
```

<400> SEQUENCE: 21

| | | | | | | | | | | | | | | |
|---|---|---|---|---|---|---|---|---|---|---|---|---|---|---|
|Met|Asn|Lys|Phe|Leu|Ile|Val|Val|Leu|Leu|Ala|Phe|Cys|Val|Phe|Ser|
|1| | |  |5| | | | |10| | | | |15| |

Ser Phe Ala Gln Ala Asp Asp Ser Lys Ser Ala Phe Asn Leu Gly Ala
                20                  25              30

Gly Glu Lys Leu Leu Ala Tyr Glu Thr Ser Lys Lys Asp Pro Ile Val
        35                40                  45

Pro Phe Leu Leu Asn Leu Phe Leu Gly Phe Gly Ile Gly Ser Phe Ala
    50                  55                  60

Gln Gly Asp Ile Leu Gly Gly Phe Leu Ile Leu Gly Phe Asp Ala Val
65              70                  75              80

Gly Ile Gly Leu Ile Leu Thr Gly Ala Tyr Leu Asp Ile Lys Ala Leu
            85                  90              95

Asp Lys Asn Ala Pro Lys Ala Ala Phe Lys Trp Thr Trp Gly Lys Gly
            100              105           110

Met Met Leu Ala Gly Ala Val Thr Met Ala Val Thr Arg Leu Thr Glu
        115              120              125

Ile Ile Ile Pro Phe Thr Phe Ala Asn Ser Tyr Asn Arg Lys Leu Lys
    130                135              140

Asn Ser Leu Asn Ile Ala Phe Gly Gly Phe Glu Pro Ser Phe Asp Ile
145              150                155           160

Asn Met Gly Gln Ala Ser Ala Leu Gly Phe Glu Leu Ser Phe Lys Lys
        165              170              175

Ser Tyr

<210> SEQ ID NO 22
<211> LENGTH: 749
<212> TYPE: DNA
<213> ORGANISM: Borrelia garinii
<220> FEATURE:
<221> NAME/KEY: CDS
<222> LOCATION: (192)..(725)

<400> SEQUENCE: 22
tagaattttc aacaaataaa gatattgtta aaagaattga aattgctaat tttatggtta          60
aatcaagaag ctctattggt aagcgaattt cgagtaacaa tttgaaaaaa gttaaattta         120
aatagttcca aaagcctttt ttaaatttca ttaatatgct accataatac cagtttaata         180
aagggttttt t atg aat aag ttt tta att ttt att ttg gta atc ttt tgt          230
             Met Asn Lys Phe Leu Ile Phe Ile Leu Val Ile Phe Cys
             1             5                10 gct ttt tct agt ttt gct caa gat gat tct aaa agc act ttt aat ctg          278
Ala Phe Ser Ser Phe Ala Gln Asp Asp Ser Lys Ser Thr Phe Asn Leu
    15                  20                  25 gga gcg gga gaa aaa ttt ttg gtt tat gaa act aat aag aaa gat tct          326
Gly Ala Gly Glu Lys Phe Leu Val Tyr Glu Thr Asn Lys Lys Asp Ser
  30                35                  40              45 ctt gta cca ttt tta ttg aac ctt ttt tta ggg ttc ggg ata ggt tct          374
Leu Val Pro Phe Leu Leu Asn Leu Phe Leu Gly Phe Gly Ile Gly Ser
            50                  55                  60 ttt gct caa gga gat atc ctt gga ggt tct ctt att ctt gga ttt gat          422
Phe Ala Gln Gly Asp Ile Leu Gly Gly Ser Leu Ile Leu Gly Phe Asp
                65                70              75 gcg gtt ggt ata ggg tta ata ctt aca gga gct tat ttg gac atc aag          470
Ala Val Gly Ile Gly Leu Ile Leu Thr Gly Ala Tyr Leu Asp Ile Lys
        80                  85                  90

-continued

```
gat ttt gat aat aat gct aaa aaa gct gat ttt aag tgg act tgg ggt      518
Asp Phe Asp Asn Asn Ala Lys Lys Ala Asp Phe Lys Trp Thr Trp Gly
     95                 100                 105 aag gga atg atg ttg gca ggt gtg gtt act atg gct gtg aca aga ttg      566
Lys Gly Met Met Leu Ala Gly Val Val Thr Met Ala Val Thr Arg Leu
110                 115                 120                 125 aca gaa att gtt ctt cca ttt aca ttt gct aat aat tat aac agg aag      614
Thr Glu Ile Val Leu Pro Phe Thr Phe Ala Asn Asn Tyr Asn Arg Lys
                130                 135                 140 ctg aaa aat agt ctt aat ata gcc ttg gga gga ttt gag cct agt ttt      662
Leu Lys Asn Ser Leu Asn Ile Ala Leu Gly Gly Phe Glu Pro Ser Phe
            145                 150                 155 gat att aac atg ggc caa gct agt gct ctt ggt ttt gga ctg tct ttc      710
Asp Ile Asn Met Gly Gln Ala Ser Ala Leu Gly Phe Gly Leu Ser Phe
        160                 165                 170 aaa aaa agc tat taa ttttatttat ctagaaaatg ggtg                       749
Lys Lys Ser Tyr
    175

<210> SEQ ID NO 23
<211> LENGTH: 177
<212> TYPE: PRT
<213> ORGANISM: Borrelia garinii

<400> SEQUENCE: 23

Met Asn Lys Phe Leu Ile Phe Ile Leu Val Ile Phe Cys Ala Phe Ser
  1               5                  10                  15

Ser Phe Ala Gln Asp Asp Ser Lys Ser Thr Phe Asn Leu Gly Ala Gly
            20                  25                  30

Glu Lys Phe Leu Val Tyr Glu Thr Asn Lys Lys Asp Ser Leu Val Pro
        35                  40                  45

Phe Leu Leu Asn Leu Phe Leu Gly Phe Gly Ile Gly Ser Phe Ala Gln
     50                  55                  60

Gly Asp Ile Leu Gly Gly Ser Leu Ile Leu Gly Phe Asp Ala Val Gly
 65                  70                  75                  80

Ile Gly Leu Ile Leu Thr Gly Ala Tyr Leu Asp Ile Lys Asp Phe Asp
                 85                  90                  95

Asn Asn Ala Lys Lys Ala Asp Phe Lys Trp Thr Trp Gly Lys Gly Met
            100                 105                 110

Met Leu Ala Gly Val Val Thr Met Ala Val Thr Arg Leu Thr Glu Ile
        115                 120                 125

Val Leu Pro Phe Thr Phe Ala Asn Asn Tyr Asn Arg Lys Leu Lys Asn
    130                 135                 140

Ser Leu Asn Ile Ala Leu Gly Gly Phe Glu Pro Ser Phe Asp Ile Asn
145                 150                 155                 160

Met Gly Gln Ala Ser Ala Leu Gly Phe Gly Leu Ser Phe Lys Lys Ser
                165                 170                 175

Tyr

<210> SEQ ID NO 24
<211> LENGTH: 32
<212> TYPE: DNA
<213> ORGANISM: Borrelia burgdorferi

<400> SEQUENCE: 24
ttggcaggta cctgtgtttt ttctagcttt gc                                   32

<210> SEQ ID NO 25
```

```
<210> SEQ ID NO 25
<211> LENGTH: 32
<212> TYPE: DNA
<213> ORGANISM: Borrelia burgdorferi

<400> SEQUENCE: 25
cacccatttt ctagataaat aaaattaata gc                                    32

<210> SEQ ID NO 26
<211> LENGTH: 33
<212> TYPE: DNA
<213> ORGANISM: Borrelia burgdorferi

<400> SEQUENCE: 26
ataaaaggta ccatagcttt ttttgaaaga cag                                   33

<210> SEQ ID NO 27
<211> LENGTH: 32
<212> TYPE: DNA
<213> ORGANISM: Borrelia burgdorferi

<400> SEQUENCE: 27
ttggcagaat tctgtgtttt ttctagcttt gc                                    32

<210> SEQ ID NO 28
<211> LENGTH: 21
<212> TYPE: DNA
<213> ORGANISM: Borrelia burgdorferi

<400> SEQUENCE: 28
tcttttctgc agtcaccgtc g                                                21

<210> SEQ ID NO 29
<211> LENGTH: 30
<212> TYPE: DNA
<213> ORGANISM: Borrelia burgdorferi

<400> SEQUENCE: 29
ttgcttacag aattcgctgg gcgaaacgaa                                       30

<210> SEQ ID NO 30
<211> LENGTH: 396
<212> TYPE: DNA
<213> ORGANISM: Borrelia burgdorferi
<220> FEATURE:
<221> NAME/KEY: CDS
<222> LOCATION: (109)..(396)

<400> SEQUENCE: 30
acgagctcaa tccaaacttt atttgcttgc aataaattaa tattaattta ttataaattg      60
cgctaatatt ttacttgtca aaacttacca ttaggagata ataaaaac atg aaa aaa      117
                                                    Met Lys Lys
                                                      1 att ttc aca tta ata tta att ttt ggg ttg aca att gaa atc ttt gcc      165
Ile Phe Thr Leu Ile Leu Ile Phe Gly Leu Thr Ile Glu Ile Phe Ala
      5                  10                  15 aca aaa gac aca caa aat aga att gaa aaa ggc att gaa agt ttt aac      213
Thr Lys Asp Thr Gln Asn Arg Ile Glu Lys Gly Ile Glu Ser Phe Asn
 20                  25                  30                  35 aaa tat gat aaa gag aaa aaa aat cca ata ggg cca ttc ctt tta aat      261
Lys Tyr Asp Lys Glu Lys Lys Asn Pro Ile Gly Pro Phe Leu Leu Asn
             40                  45                  50 tta ttt ttg ccc ttt gga ata gga tcc ttt gtc caa ggg gat tat att      309
Leu Phe Leu Pro Phe Gly Ile Gly Ser Phe Val Gln Gly Asp Tyr Ile
```

-continued

```
                  55                  60                  65
ggt gga ggc tca gtg ctt gga ttt aat tta tta gga gca atc ctt tgg       357
Gly Gly Gly Ser Val Leu Gly Phe Asn Leu Leu Gly Ala Ile Leu Trp
            70                  75                  80 gaa ctg gaa tta ttc tta atc acc gag aaa cac aat taa                   396
Glu Leu Glu Leu Phe Leu Ile Thr Glu Lys His Asn
        85                  90                  95
```

<210> SEQ ID NO 31
<211> LENGTH: 95
<212> TYPE: PRT
<213> ORGANISM: Borrelia burgdorferi

<400> SEQUENCE: 31

Met Lys Lys Ile Phe Thr Leu Ile Leu Ile Phe Gly Leu Thr Ile Glu
 1               5                  10                  15

Ile Phe Ala Thr Lys Asp Thr Gln Asn Arg Ile Glu Lys Gly Ile Glu
                20                  25                  30

Ser Phe Asn Lys Tyr Asp Lys Glu Lys Lys Asn Pro Ile Gly Pro Phe
            35                  40                  45

Leu Leu Asn Leu Phe Leu Pro Phe Gly Ile Gly Ser Phe Val Gln Gly
    50                  55                  60

Asp Tyr Ile Gly Gly Ser Val Leu Gly Phe Asn Leu Leu Gly Ala
65                  70                  75                  80

Ile Leu Trp Glu Leu Glu Leu Phe Leu Ile Thr Glu Lys His Asn
                85                  90                  95

P13 ANTIGENS FROM BORRELIA

RELATED APPLICATIONS

This application claims priority from DK 1041/97, filed Sep. 10, 1997; U.S. No. 60/059,036, filed Sep. 16, 1997; and PCT/DK98/00379, filed Sep. 4, 1998; and each of these applications is incorporated herein by reference. Further, this application is a continuation-in-part of PCT/DK98/00379, filed Sep. 4, 1998 and designating the U.S. In addition, reference is made to U.S. Pat. Nos. 5,777,095; 5,688,512; 5,582,990 and 5,523,089 and U.S. applications Ser. No. 08/750,494, filed Jun. 12, 1997 as the U.S. National Phase of as PCT/US95/07665, and U.S. Ser. No. 08/264,036, filed Jun. 22, 1994. Each of these patents and applications, as well as all documents cited in the text of this application, and references cited in the documents in this application (including references cited in the aforementioned patents and applications) are hereby incorporated herein by reference. And, with respect to the following text, as well as to the aforementioned patents and applications, the term "substantially pure" can mean free of other Borrelia proteins, e.g., a "substantially pure" P13 can be P13 free of other Borrelia proteins (which would be present in a lysate or could be present if P13 is merely isolated from such a lysate).

FIELD OF THE INVENTION

The present invention relates to nucleic acid sequences encoding antigenic proteins associated with *Borrelia burgdorferi sensu lato* (*Borrelia burgdorferi sensu stricto, Borrelia garinii,* and *Borrelia afzelii;* collectively designated Bb hereinafter), particularly polypeptides associated with virulence; vaccine formulations comprising these polypeptides are also part of the invention. The invention also relates to methods for producing Bb immunogenic polypeptides and corresponding antibodies. Other embodiments of the invention relate to methods for detecting Lyme disease and transformed cells comprising Bb associated nucleic acids.

BACKGROUND OF THE INVENTION

Lyme disease is a multisystem disease resulting from tick transmission of the infectious agent, Bb (Rahn and Malawista, 1991). Although recognised as a clinical entity within the last few decades (Steere et al., 1977), case reports resembling Lyme disease date back to the early part of the 20th century. Cases of the disease have been reported in Europe, Asia and North America (Schmid, 1985). Despite a relatively low total incidence compared to other infectious diseases, Lyme disease represents a significant health problem because of its potentially severe cardiovascular, neurologic and arthritic complications, difficulty in diagnosis and treatment and high prevalence in some geographic regions.

Bb is not a homogeneous group but has a variable genetic content, which may in turn affect its virulence, pattern of pathogenesis and immunogenicity. Lyme borreliosis associated borreliae are so far taxonomically placed into three species, *Borrelia burgdorferi sensu stricto, Borrelia garinii,* and *Borrelia afzelii* (Burgdorfer et al., 1983, Baranton et al., 1992, Canica et al., 1993). It is well documented that considerable genetic, antigenic and immunogenic heterogeneity occurs among them, as well as among the strains within the separate species (Baranton et al., 1992, Canica et al., 1993, Zingg et al., 1993, Wilske et al., 1993, Adam et al., 1991, Marconi and Garon 1992). The major evidence of this phenomenon is provided by the molecular studies of the plasmid-encoded outer surface protein A (OspA), OspB and OspC (Barbour et al., 1984, Jonsson et al., 1992, Wilske et al., 1993, Marconi et al., 1993). In different animal models efficient protection is achieved by passive and active immunisation with OspA (Schaible et al., 1990, Fikrig et al., 1992, Erdile et al., 1993), and therefore, OspA remains one of the main candidates for Borrelia vaccine. It is unclear, however, whether inter- and intra-species heterogeneity of OspA, as well as other competitors for immunoprophylaxis, allow efficient cross-protection (Fikrig et al., 1992, Norris et al., 1992). Furthermore, it was recently suggested that certain protective antibodies produced early in the course of Borrelia infection are unrelated to OspA (Norton Hughes et al., 1993, Barthold and Bockenstedt, 1993).

Its virulence factors, pathogenetic mechanisms and means of immune evasion are unknown. At the level of patient care, diagnosis of the disease is complicated by its varied clinical presentation and the lack of practical, standardised diagnostic tests of high sensitivity and specificity. Antimicrobial therapy is not always effective, particularly in the later stages of the disease.

Variation among Bb strains and species and the changes resulting from in vitro passage add to the problems of developing vaccines or immunodiagnostics from either the whole organism or specifically associated proteins. Using a PCR assay, it was found that one set of oligonucleotide primers was specific for North American Bb isolates, another for most European isolates and a third set recognised all Bb strains (Rosa et al., 1989).

Serological assays for the diagnosis and detection of Lyme disease are thought to offer the best promise for sensitive and specific diagnosis. However, serologic assays generally use whole Bb as antigen and suffer from a low "signal to noise" ratio, i.e., a low degree of reactivity in positive samples, particularly early in the disease, as compared to negative samples. This problem results in high numbers of false negatives and the potential for false positives. Background reactivity in negative controls may be due in part to conserved antigens such as the 41K flagellin and the 60K "Common Antigen". These Bb proteins possess a high degree of sequence homology with similar proteins found in other bacteria. Therefore normal individuals will often express anti-flagellar and anti-60K antibodies. Unique, highly reactive Bb antigens for serological assays are therefore desirable but heretofore unavailable.

Diagnosis of Lyme disease remains a complex and uncertain endeavour, due to lack of any single diagnostic tool that is both sensitive and specific. Clinical manifestations and history are the most common bases for diagnosis. However, there is a pressing need for specific, sensitive, reproducible and readily available confirmatory tests. Direct detection offers proof of infection but is hampered by the extremely low levels of Bb that are typically present during infection, as well as the inaccessibility of sites that tend to be consistently positive (e.g., heart and bladder). Culture, although sensitive, is cumbersome and requires 1–3 weeks to obtain a positive result. PCR appears to offer promise in terms of direct detection (Lebech et al., 1991) and indeed Goodman et al. (1991) have reported detection of Bb DNA in the urine of patients with active Lyme disease using a PCR method. However, it is unlikely that PCR assays will become commonly used in clinical laboratories because of the degree of skill required for its use and the high risk of DNA contamination.

Another problem in detection of Lyme disease is the substantial number of humans exposed to Bb who develop inapparent or asymptomatic infections. This number has been estimated to be as high as 50% (Steere et al., 1986).

There is clearly a need for means of preparing Bb-specific antigens, e.g., for the development of diagnostic tests for Lyme disease. Adequate assays do not exist and should ideally meet several criteria, including (1) expression of an antigen by all pathogenic Bb strains, (2) elicitation of an immune response in all Lyme disease patients, (3) high immunogenicity with a detectable antibody response early in the infection stage, (4) antigens unique to Bb without cross-reactivity to other antigens, and (5) distinction between individuals exposed to non-pathogenic as opposed to pathogenic forms of Bb.

There have been several studies describing low molecular weight proteins from Bb. Katona et al. showed the presence of a major low-molecular weight lipoprotein specific for *B. burgdorferi* and raised the possibility that it was a borrelial equivalent of Braun's lipoprotein (Katona et al., 1992). Another study reported an immunogenic 14 kDa surface protein of *B. burgdorferi* recognised by sera from Lyme disease patients (Sambri et al., 1991). A 14 kDa mitogenic lipoprotein of *B. burgdorferi* was reported by Honarvar et al. (1994).

Sadziene et al. (1994) when analysing an Osp-less *B. burgdorferi* strain identified a 13 kDa surface exposed protein which was designated p13.

OBJECT OF THE INVENTION

It is an object of the invention to provide novel nucleic acid fragments and polypeptide fragments which are useful in the preparation of diagnostics and prophylactic means and compositions relating to infections with Bb. It is a further object to provide novel vaccines and diagnostic means as well as methods for the preparation and use of such vaccines and diagnostic means. Finally, it is an object of the invention to provide tools such as vectors and transformed cells which facilitate the preparation of the polypeptide fragments and the vaccines.

SUMMARY OF THE INVENTION

The inventors have surprisingly found that an antigen from Bb with an apparent molecular weight of 13 kDa (determined by SDS-PAGE, and subsequent visualization such as staining with Coomassie Blue) is highly conserved in the three strains *B. burgdorferi sensu stricto* B31, *B. garinii* IP90, and *B. afzelii* ACAI, whereas this antigen cannot be found in Borrelia species related to relapsing fever and avian borreliosis. The disclosed antigens are therefore excellent candidates for vaccines and diagnostics relating to infections with Bb. The antigens will be termed P13.

The present invention thus addresses one or more of the foregoing or other problems associated with the preparation and use of Bb specific antigens, particularly those antigens associated with virulence and which are useful for developing detection and diagnostic methods for Lyme disease. The present invention involves the identification of such antigens, which herein are designated P13 as well as the identification and isolation of Bb nucleic acid sequences that encode P13 antigens or antigenic polypeptides derived therefrom. These sequences are useful for preparing expression vectors for transforming host cells to produce recombinant antigenic polypeptides. It is further proposed that these antigens will be useful as vaccines or immunodiagnostic agents for Bb associated diseases such as Lyme disease in particular.

The DNA of the present invention was isolated from Bb. The microorganism is a spiral-shaped organism approximately 0.2 micron in diameter and ranging in length from about 10 to 30 microns. Like other spirochaetes, it possesses an inner membrane, a thin peptidoglycan layer, an outer membrane, and periplasmic flagella which lie between the inner and outer membranes. Bb is an obligate parasite found only in association with infected animals and arthropod vectors in endemic areas. Bb-like organisms have also been identified in birds raising the possibility that birds could also serve as an animal reservoir. While some Bb isolates have been cloned, most isolates have not been cloned and most likely represent mixtures of different variants even at the time of culture origin.

Bb has similarities with other relapsing fever organisms such as *B. hermsii*. Bb has a single chromosome with two unusual features, linear conformation and small size (approximately 900 kilobase pairs). Fresh isolates of Bb contain up to four linear plasmids and six circular supercoiled plasmids. The plasmid content of different Bb isolates is highly variable. For example, in one study only two of thirteen strains had similar plasmid profiles. Some plasmids are lost during in vitro passage which may correlate with loss of virulence. Outer surface proteins OspA and OspB are encoded on the 49 kbp linear plasmid. The P13 membrane-associated/outer surface proteins discovered by the inventors are encoded on the Bb chromosome. The P13 protein gene being localised to the chromosome of borreliae shows a higher degree of conservation among Lyme disease associated borreliae contrary to the plasmid-encoded major outer surface proteins A, B, and C which exhibit a significant species and strain dependent genetic and antigenic polymorphism (Barbour 1986, Jonsson et al., 1992, Wilske et al., 1993). Furthermore, the level of similarity and identity between the deduced amino acid sequence of the P13 protein from different borrelia strains further shows that this protein can be useful as a vaccine against Lyme disease as well as a target for diagnostic use.

In order to identify DNA segments encoding the P13 proteins, purified protein was isolated from *B. burgdorferi* B313 by preparative SDS-PAGE for subsequent use in amino acid sequencing. Attempts to N-terminally sequence the purified protein by standard techniques were unsuccessful. The protein was therefore subjected to V8 protease cleavage. After protease cleavage the peptide was transferred to polyvinylene diffusable membranes, and sequence analysis was performed using standard sequencing techniques (Matsudaira, 1987). A 25 amino acid sequence was identified (SEQ ID NO: 1).

DNA libraries were prepared by restriction enzyme digestion of DNA prepared from the strains *B. burgdorferi* B31, *B. afzelii* ACAI and *B. garinii* IP90.

Codons for the amino acid sequence obtained, SEQ ID NO: 1, were selected by reverse translation based on (1) conclusion that codons containing A or T were favoured and (2) knowledge of published DNA sequences for several Bb proteins. A choice favouring A or T containing codons was based on the observation that the G+C content of Bb is only 28–35% (Burman et al., 1990). Two oligonucleotides were synthesized having the sequences shown in in SEQ ID NO: 2 and SEQ ID NO:3. These were used as primers in a PCR reaction with DNA prepared from *B. burgdorferi* B31 as template. The amplified fragment was sequenced, SEQ ID NO: 4, and verified to code for the amino acid sequence, SEQ ID NO: 1.

A DNA probe, designated Y7 (SEQ ID NO:7), was designed and used to screen the DNA library prepared from *B. burgdorferi* B31 in an attempt to identify DNA encoding the P13 protein from this Bb species. This attempt proved unsuccessful.

An RsaI restriction site identified in the DNA sequence of the PCR fragment was used in a further attempt to clone the P13 gene. Bb DNA was digested with RsaI and the fragments cloned into a pUC plasmid. Further PCR amplification using the sequence identified surrounding the RsaI site yielded DNA fragments which were found to code for the P13 protein.

The identified sequence of the P13 gene from *B. burgdorferi* B31 was used to design PCR primers which were subsequently used to clone the P13 gene from *B. afzelii* ACAI and *B. garinii* IP90.

The P13 protein which has been cloned by the inventors of the present invention has been shown to have a molecular weight of about 19,000 as calculated from the deduced amino acid sequence of the full-length protein but a molecular weight of about 14,000 as determined by MS but nevertheless to be identical to a protein from Bb which has an apparent molecular weight in SDS-PAGE of 13 kDa. This difference can be explained by post-translational modifications of the P13 protein. This is in accordance with the observation that it was not possible by standard methods to obtain an N-terminal amino acid sequence of P13 protein prepared from Bb.

The deduced amino acid sequences of P13 from *B. burgdorferi* B31, *B. afzelii* ACAI and *B. garinii* IP90 were analysed and it was found that the N-terminal regions of the deduced amino acid sequences are typical of the signal peptides of bacterial proteins. These leader peptide sequences are typical of exported proteins with a basic residue followed by a hydrophobic and a potential leader peptidase I cleavage site according to the criteria established by von Heijne (1986).

Amino acid sequences resembling the signal sequences of bacterial lipoproteins can also be found in the N-terminal region of the deduced amino acid sequences. The N-terminal methionine is followed by a hydrophobic region and a signal peptidase 11 recognition sequence. The signal sequences, Leu Ala Thr Phe Cys for *B. burgdorferi* B31, Leu Leu Ala Phe Cys for *B. afzelii* ACAI and Leu Val lie Phe Cys for *B. garinii* I P90, differed somewhat from the consensus signal peptidase II recognition sequence (Leu Xaa Xaa Cys) found in most bacteria, but resembled the cleavage sequence Leu Ser Ile Ser Cys of the outer surface protein D (OspD) of Bb and Leu Met Ile Gly Cys of the variable major proteins Vmp7 and Vmp21 of *B. hermsii*. These surface antigens have been shown to be lipoproteins (Norris et al., 1992; Burman et al., 1990). The presence of this leader sequence may imply that mature P13 proteins are translocated across the cytoplasmic membrane and are anchored to the cytoplasmic membrane and/or outer membranes via fatty acids associated with an N-terminal cysteinyl residue. Lipidated forms of the outer surface protein A (OspA) from Bb have been shown to be more immunogenic that non-lipidated forms of OspA (Erdile et al., 1993).

However, it should be understood that when the terms "13 kDa protein" or "13 kDa antigen" or "13 kDa polypeptide" are used in the present specification and claims, this is an alternative designation of the P13 polypeptide.

Antigenicity of the P13 protein was verified by immunisation of a rabbit. Antiserum collected from rabbits injected with the P13 protein prepared from *B. burgdorferi* B313 was found to recognise the P13 protein of *B. burgdorferi* B31, *B. afzelii* ACAI, and *B. grainii* IP90. There was no apparent reactivity of the antiserum with *B. hemsii, B. crocidurae, B. anserina*.

The nucleic acid segments of the present invention encode antigenic amino acid sequences associated with Bb. These sequences are important for their ability to selectively hybridise with complementary stretches of Bb gene segments. Varying conditions of hybridization may be desired, depending on the application envisioned and the selectivity of the probe toward the target sequence. Where a high degree of selectivity is desired, one may employ relatively stringent conditions to form the hybrids, such as relatively low salt and/or high temperature conditions. Under these conditions, little mismatch between the probe and template or target strand is tolerated. Less stringent conditions might be employed when, for example, one desires to prepare mutants or to detect mutants when significant divergence exists.

In clinical diagnostic embodiments, nucleic acid segments of the present invention may be used in combination with an appropriate means, such as a label, to determine hybridization with DNA of a pathogenic organism. Typical methods of detection might utilise, for example, radioactive species, enzyme-active or other marker ligands such as avidin/biotin, which are detectable directly or indirectly. In preferred diagnostic embodiments, one will likely desire to employ an enzyme tag such as alkaline phosphatase or peroxidase rather than radioactive or other reagents that may have undesirable environmental effects. Enzyme tags, for example, often utilise calorimetric indicator substrates that are readily detectable spectrophotometrically, many in the visible wavelength range. Luminescent substrates could also be used for increased sensitivity.

Hybridisable DNA segments may include any of a number of segments of the disclosed DNA. For example, relatively short segments of at least 12 or so base pairs may be employed, or, more preferably when probes are desired, longer segments of at least 20, at least 30, and at least 40 base pairs, depending on the particular applications desired. Shorter segments are preferred as primers in molecular amplification techniques such as PCR, while some of the longer segments are generally preferable for blot hybridizations. It should be pointed out, however, that while sequences disclosed for the DNA segments of the present invention are defined by SEQ ID NO: 18, SEQ ID NO: 20 and SEQ ID NO: 22, a certain amount of variation or base substitution would be expected, e.g., as may be found in mutants or strain variants, but which do not significantly affect hybridization characteristics. Such variations, including base modifications occurring naturally or otherwise, are intended to be included within the scope of the present invention.

While the Bb P13 antigens of the present invention have been disclosed in terms of the specific amino acid sequences SEQ ID NO: 19, SEQ ID NO: 21 and SEQ ID NO: 23, it is nonetheless contemplated that the amino acid sequences will be found to vary from species to species and from isolate to isolate. Moreover, it is quite clear that changes may be made in the underlying amino acid sequence through, e.g., site-directed mutagenesis of the DNA coding sequence, in a way that will not negate its antigenic capability.

The invention also relates to at least partially purified antigenic Bb proteins or polypeptides which are capable of producing an in vivo immunogenic response when challenged with Bb. These proteins may comprise all or part of the amino acid sequence encoded by the DNA disclosed herein. Particularly preferred antigenic proteins have the amino acid sequence shown in SEQ ID NO: 19, SEQ ID NO: 21 and SEQ ID NO: 23. Post-translationally modified forms of these antigenic proteins are also the subject of this invention. These proteins as well as their epitopes will be useful in connection with vaccine development, and as antigen(s) in immunoassays for detection of Bb antibodies in biological fluids such as serum, seminal or vaginal fluids, urine, saliva, body exudates and the like.

In other aspects, the invention concerns recombinant vectors such as plasmids, phages or viruses, which comprise DNA segments in accordance with the invention, for use in replicating such sequences or even for the expression of encoded antigenic peptides or proteins. Vectors or plasmids may be used to transform a selected host cell. In preparing a suitable vector for transforming a cell, desired DNA segments from any of several Bb sources may be used, including genomic fragments, cDNA or synthetic DNA. In the practice of the present invention, an expression vector may incorporate at least part of the DNA sequence of SEQ ID NO: 18, SEQ ID NO: 20 and SEQ ID NO: 22, encoding one or more epitopic segments of the disclosed antigens of the present invention.

Expression vectors may be constructed to include any of the DNA segments hereinabove disclosed. Such DNA might encode an antigenic protein specific for virulent strains of Bb or even hybridization probes for detecting Bb nucleic acids in samples. Longer or shorter DNA segments could be used, depending on the antigenic protein desired. Epitopic regions of the disclosed proteins of the present invention expressed or encoded by the disclosed DNA could be included as relatively short segments of DNA. A wide variety of expression vectors are possible including, for example, DNA segments encoding reporter gene products useful for identification of heterologous gene products and/or resistance genes such as antibiotic resistance genes which may be useful in identifying transformed cells.

Recombinant vectors such as those described are particularly preferred for transforming bacterial host cells. Accordingly, a method is disclosed for preparing transformed bacterial host cells that generally includes the steps of selecting a suitable bacterial host cell, preparing a vector containing a desired DNA segment and transforming the selected bacterial host cell. Several types of bacterial host cells may be employed, including Bb, *E. coli, B. subtilis,* and the like as well as prokaryotic host cells.

Transformed cells may be selected using various techniques, including screening by differential hybridization, differential display techniques, identification of fused reporter gene products, resistance markers, anti-antigen antibodies and the like. After identification of an appropriate clone, it may be selected and cultivated under conditions appropriate to the circumstances, as for example, conditions favouring expression or, when DNA is desired, replication conditions.

Another aspect of the invention involves the preparation of antibodies and vaccines from the antigenic P13 proteins or epitopic regions of these proteins encoded by the disclosed DNA. It is expected that the sensitivity and specificity of an antibody response to these P13 proteins and their epitopes will be superior to the response that has been obtained from other Bb antigens that are not associated with virulence. Previous work with several Bb antigens isolated from both virulent and avirulent strains indicated low sensitivity when immunofluorescence and ELISA assays were employed, especially during early stages of infection.

In both immunodiagnostics and vaccine preparation, it is often possible and indeed more practical to prepare antigens from segments of a known immunogenic protein or polypeptide. Certain epitopic regions may be used to produce responses similar to those produced by the entire antigenic polypeptide. Potential antigenic or immunogenic regions may be identified by any of a number of approaches, e.g., Jameson-Wolf or Kyte-Doolittle antigenicity analyses or Hopp and Woods (1981) hydrophobicity analysis (see, e.g., Kyte and Doolittle, 1982, or U.S. Pat. No. 4,554,101). Hydrophobicity analysis assigns average hydrophilicity values to each amino acid residue, and from these values average hydrophilicities can be calculated and regions of greatest hydrophilicity determined. Using one or more of these methods, regions of predicted antigenicity may be derived from the amino acid sequence of the disclosed P13 polypeptides. Proposed epitopic regions from the disclosed P13 antigens include the sequences corresponding to amino acid residues 7–15, 21–24, 29–35, 83–92, 126–135 and 162–167 in SEQ ID NO: 19; amino acid residues 7–14, 20–23, 28–35, 82–89, 125–134 and 162–166 in SEQ ID NO: 21; and amino acid 35 residues 6–14, 18–21, 27–34, 79–92, 125–133 and 161–165 in SEQ ID NO: 23.

Antigenic epitopes can also be determined using different experimental procedures known to the skilled person. For example, the DNA encoding the P13 polypeptides can be digested with restriction enzymes in such a manner that DNA fragments encoding specific parts of the P13 polypeptide are obtained. These DNA fragments can be expressed in a suitable expression system. The P13 polypeptide fragments obtained can be analysed with monoclonal or polyclonal antibodies obtained by immunisation with the full-length form of the P13 polypeptide or fragments thereof, or with Lyme disease patient sera to obtain information about immunogenicity and the presence of epitopes. Fragments found to be positive in such a simple screening assay where they react specifically with e.g. polyclonals raised against P13 are thus suitable candidates for a multitude of the applications where full-length P13 would also be suitable.

A similar approach can be used where random mutations are introduced in the nucleotide sequence encoding P13, and only the expression products which retain a suitable reactivity with e.g. P13 positive polyclonal antibodies will be used as candidates for further applications.

Peptide fragments for the identification of epitopes can also be obtained by synthetic methods. Suitable peptides can be synthetised based on the amino acid sequence of the P13 polypeptides, e.g. peptides with amino acid sequences identical to consecutive fragments from the N-terminus to the C-terminus of the P13 polypeptide can be synthetised on solid-phase media. Such custom-made peptide libraries can be obtained from commercial sources.

Finally, another way of simply identifying epitopes is to digest a polypeptide antigen with a known amino acid sequence with endo- and exopeptidases. The obtained fragments are tested against antibodies directed against the whole polypeptide, and by way of deduction, the precise location of the linear epitopes can be determined. A variation of this method involves the recombinant production of subfragments (cf. the above) of the full-length polypeptide followed by the same test procedure.

It is contemplated that the antigens and immunogens of the invention will be useful in providing the basis for one or more assays to detect antibodies against Bb. Previous assays have used whole Bb as the antigen. Sera from normal individuals not exposed to Bb often contain antibodies that react with Bb antigens, in particular antigens that have epitopes in common with other bacteria. It is necessary to adjust assay conditions or the diagnostic threshold of reactivity to avoid false positive reactions due to these cross-reactive antibodies in normal sera. These adjustments may in turn decrease the sensitivity of the assay and lead to false negative reactions, particularly in the early stages of Bb infection. Assays using the disclosed P13 proteins or antigenic polypeptides thereof are expected to give superior results both in terms of sensitivity and selectivity when compared to assays that use whole Bb or even purified flagella in either an indirect ELISA or an antibody capture ELISA format. Western immunoblots based on reactions with such antigens (whole Bb, flagella and the like) have been difficult to interpret due to the presence of antibodies in sera from unexposed individuals. These antibodies cross-react with Bb antigens, most particularly the 41 kDa flagellin and the 60 kDa common antigen protein. Generally, assays which use whole organisms or purified flagella tend to contain antigens with epitopes that will cross-react with other bacterial antigens. For example, the N and C terminal regions of the Bb flagellin possess 52–55% sequence identity with the *Salmonella typhimurium* and *Bacillus subtilis* sequences (Wallich et al., 1990), exemplifying the highly conserved nature of flagellin structure. The 60 kDa Bb protein is likewise 58% homologous with the *E. coli* protein (Shanafelt et al., 1991). Such cross-reactivity is not likely with the disclosed P13 antigens, which are apparently unique to Bb.

It is further anticipated that recombinantly derived P13 Bb proteins will be particularly preferred for detecting Bb infections. Unexposed individuals should have a low reactivity to one or more epitopes of the P13 proteins thereby making it possible to use lower dilutions of serum and increase sensitivity. Using a combination of more than one of these unique antigens may also enhance sensitivity without sacrificing specificity.

Preferred immunoassays are contemplated as including various types of enzyme linked immunoassays (ELISAs), immunoblot techniques, and the like, known in the art. However, it readily appreciated that utility is not limited to such assays, and useful embodiments include RIAs and other non-enzyme linked antibody binding assays or procedures.

Yet another aspect of the invention is a method of detecting Bb nucleic acid in a sample. The presence of Bb nucleic acid in the sample may be indicated by the presence of the polypeptide products which it encodes. The method therefore includes detecting the presence of at least a portion of any of the polypeptides herein disclosed. Suitable detection methods include, for example, immunodetection reagents, PCR amplification, and hybridization.

Yet another aspect of the invention includes one or more primers capable of priming amplification of the disclosed DNA of SEQ ID NO: 18, SEQ ID NO: 20 and SEQ ID NO: 22. Such primers are readily generated taking into account the base sequence of the DNA segment of SEQ ID NO: 18, SEQ ID NO: 20 and SEQ ID NO: 22, the disclosed DNA, or deriving a base sequence from the amino acid sequence of a purified polypeptide encoded by the DNA. Primers are analogous to hybridization probes, but are generally relatively short DNA segments, usually about 7–20 nucleotides.

Methods of diagnosing Lyme disease are also included in the invention. In one embodiment, an antibody-based method includes obtaining a sample from a patient suspected of having Lyme disease, exposing that sample to one or more epitopes of the Bb protein which is encoded by the DNA disclosed, and finally determining a reactivity of the antibody with one or more epitopes of a Bb protein that may be in the sample. The reactivity measured is indicative of the presence of Lyme disease. Typical samples obtainable from a patient include human serum, plasma, whole blood, cerebrospinal fluid, seminal or vaginal fluids, exudates and the like.

Several variations of antibody-based methods are contemplated for development; for example, an indirect ELISA using the P13 proteins or other Bb proteins as an antigen. The P13 proteins may be produced in large quantities by recombinant DNA vectors already disclosed and purified. Optimum concentration of the antigen could be determined by checker board titration and diagnostic potential of the P13 proteins assay examined further by testing serum from mice at different stages of infection and infected with different strains of Bb. These results could indicate the relative time course for serum conversion for each of the assays and would also show whether infection with different strains causes variation in anti-P13 protein titers.

Likewise, reactive epitopes of the P13 polypeptides are contemplated as useful either as antigens in an ELISA assay or to inhibit the reaction of antibodies toward intact P13 proteins bound to a well. Epitopic peptides could be generated by recombinant DNA techniques previously disclosed or by synthesis of peptides from individual amino acids. In either case, reaction with a given peptide would indicate presence of antibodies directed against one or more epitopes. In addition to its diagnostic potential, this method is seen as being particularly effective in characterising monoclonal antibodies against the P13 proteins and other virulence associated proteins.

In a further aspect, the present invention concerns a kit for the detection of Bb antigens, the kit including a protein or peptide which includes an epitope thereof, together with means for detecting a specific immunoreaction between an antibody and its corresponding antigen. Examples of suitable means include labels attached directly to the antigen or antibody, a secondary antibody having specificity for human Ig, or protein A or protein G. Alternatively, avidin-biotin mediated *Staphylococcus aureus* binding could be used. For example, the monoclonal antibody may be biotinylated so as to react with avidin complexed with an enzyme or a fluorescent compound.

A particular kit embodiment of the invention concerns detection of antibodies against the described Bb P13 antigens, epitopes thereof as represented by portions of the amino acid sequences, or closely related proteins or peptides, such as epitopes associated with other virulence-associated proteins detected by comparison of low-passage, virulent and high-passage, avirulent strains of Bb. The antigen for the kit(s) consists of the Bb P13 proteins or portions thereof produced by a recombinant DNA vector in *E. coli* or another bacterial or non-bacterial host. Alternatively, the antigen may be purified directly from Bb or manufactured as a synthetic peptide. Samples for the assays may be body fluids or other tissue samples from humans or animals. The presence of reactive antibodies in the samples may be demonstrated by antibody binding to antigen followed by detection of the antibody-antigen complex by any of a number of methods, including ELISA, TRIFMA (time-resolved immunofluorometric assay), RIA, fluorescence, agglutination or precipitation reactions, nephelometry, or any of these assays using avidin-biotin reactions. The degree of reactivity may be assessed by comparison to control samples, and the degree of reactivity used as a measure of present or past infection with Bb. The assay(s) could also be used to monitor reactivity during the course of Lyme disease, e.g., to determine the efficiency of therapy.

In still further embodiments, the invention contemplates a kit for the detection of Bb nucleic acids in the sample, wherein the kit includes one or more nucleic acid probes specific for the P13 genes, together with means for detecting

LEGENDS TO THE FIGURES

Figure 1B:
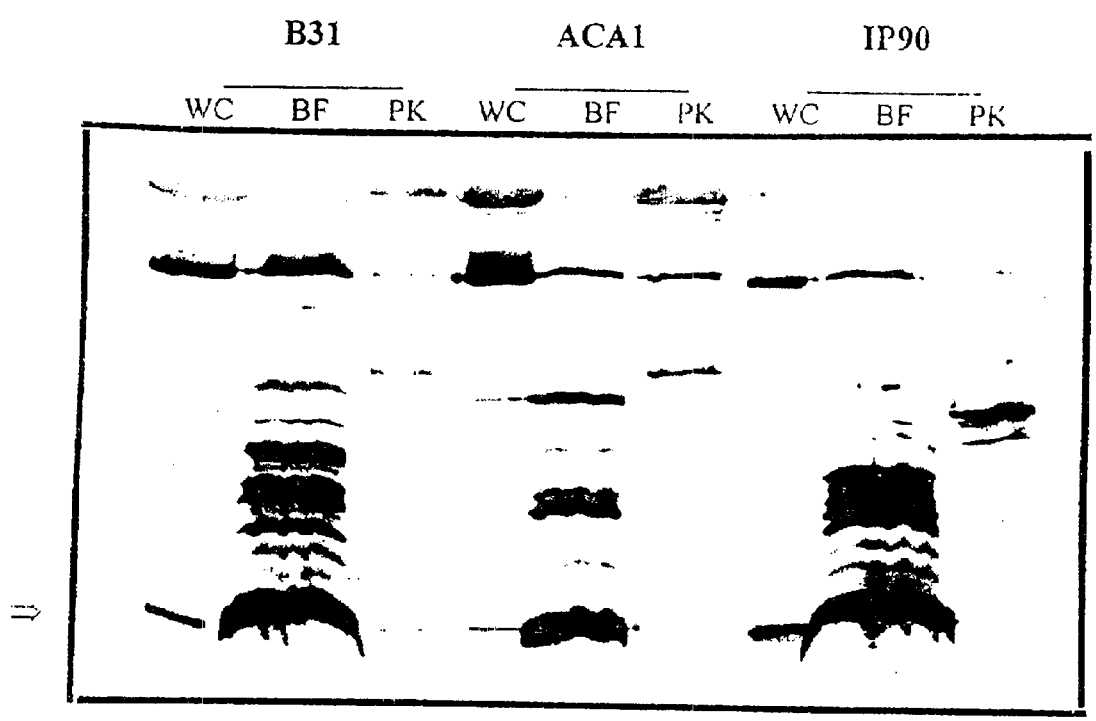
Figure 1C:
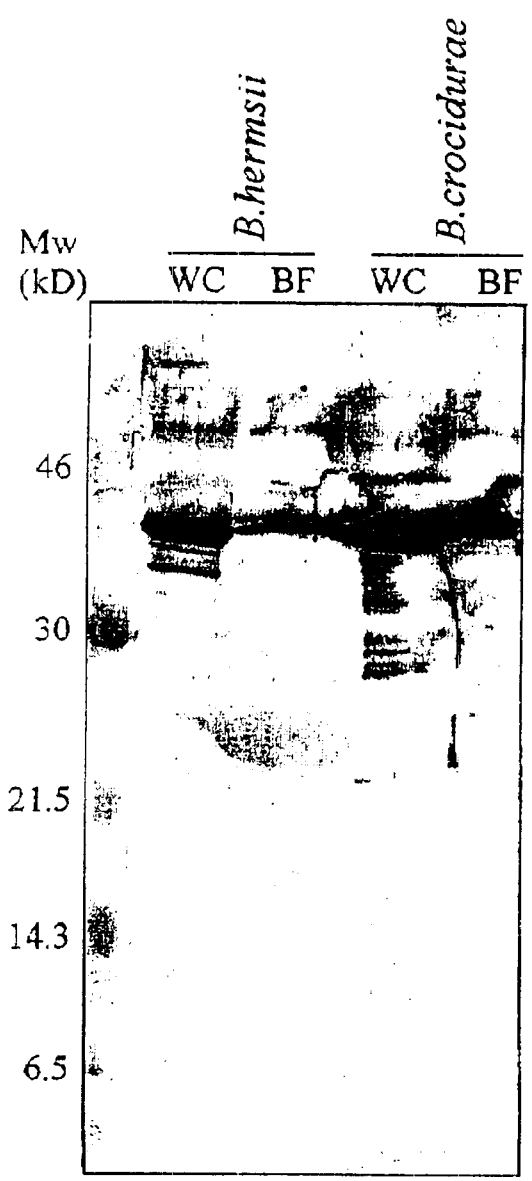

FIGS. 1A, 1B and 1C. Analysis of Borrelia proteins.
  A: Effect of Protease K treatment on Bb cells. Coomassie-blue stained 15% SDS-PAGE gel showing protein profiles of whole cell (WC), B-fraction (BF) and Proteinase K (PK) treated cells from *B. burgdorferi* B31, *B. afzelii* ACA1 and *B. grainii* IP90.
  B: The Western Blot corresponding to FIG. 1A probed with the rabbit polyclonal antiserum raised against the 13 kDa protein prepared from *B. burgdorferi* B313.
  C: Comparison of phenotypic expression of the 13 kDa protein in Borrelia species. Western Blot of SDS-PAGE separated proteins from *B. hermsii* and *B. crocidurae* probed with the rabbit polyclonal antiserum raised against the 13 kDa protein prepared from *B. burgdorferi* B313.
  Arrows indicate the position of 13 kDa protein. Mw—molecular weight standard, kD—kilodalton.

Figure 2A:
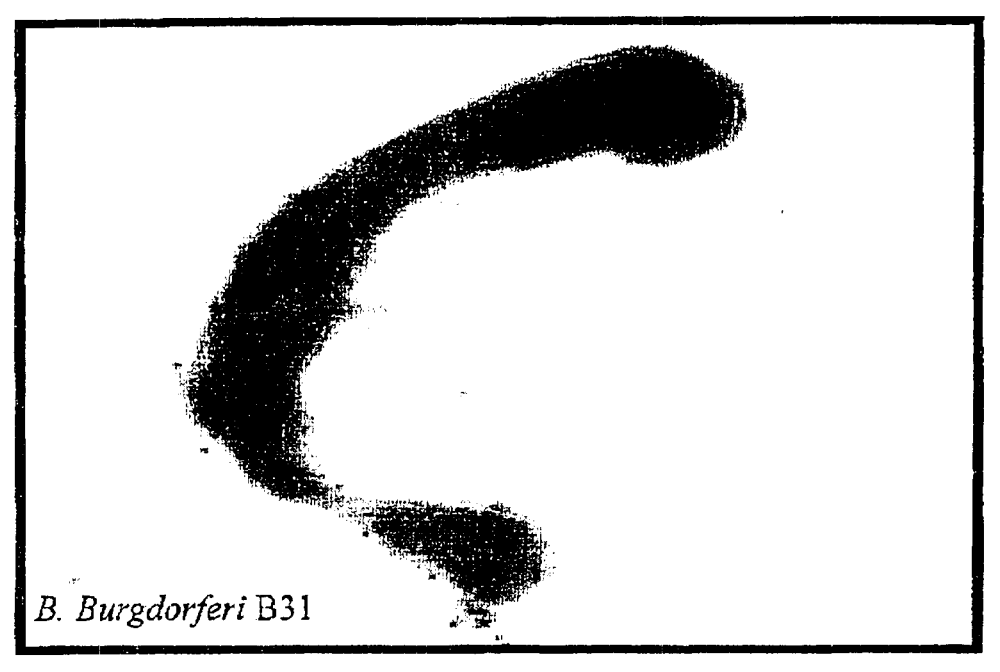
Figure 2B:
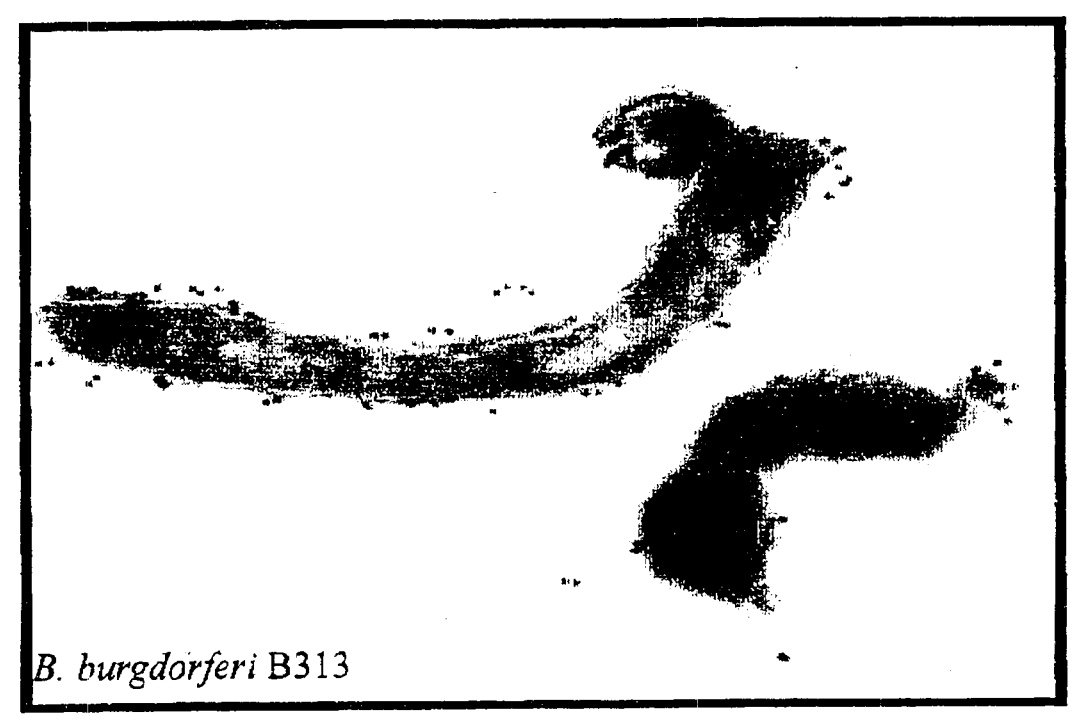

FIGS. 2A and 2B. Demonstration of outer membrane association of the 13 kDa protein.
  A: Electron micrographs of immunogold-stained cells from *B. burgdorferi* B31.
  B: Electron micrographs of immunogold-stained cells from *B. burgdorferi* B313.
  Monoclonal antibody 15G6 was used as the primary antibody.

Figure 3A:
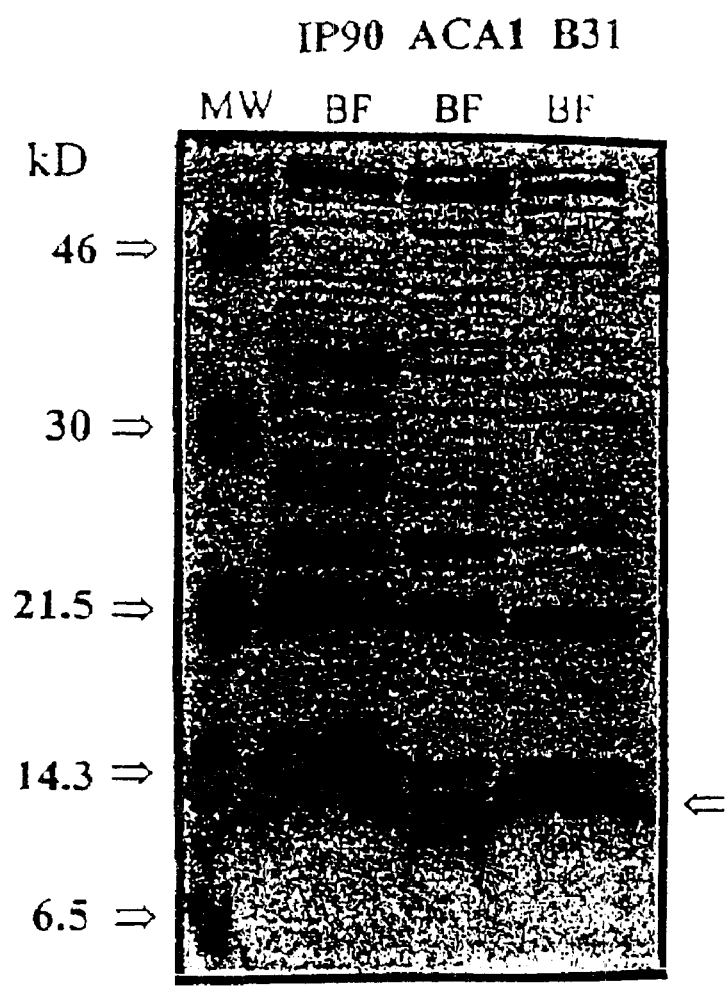
Figure 3B:
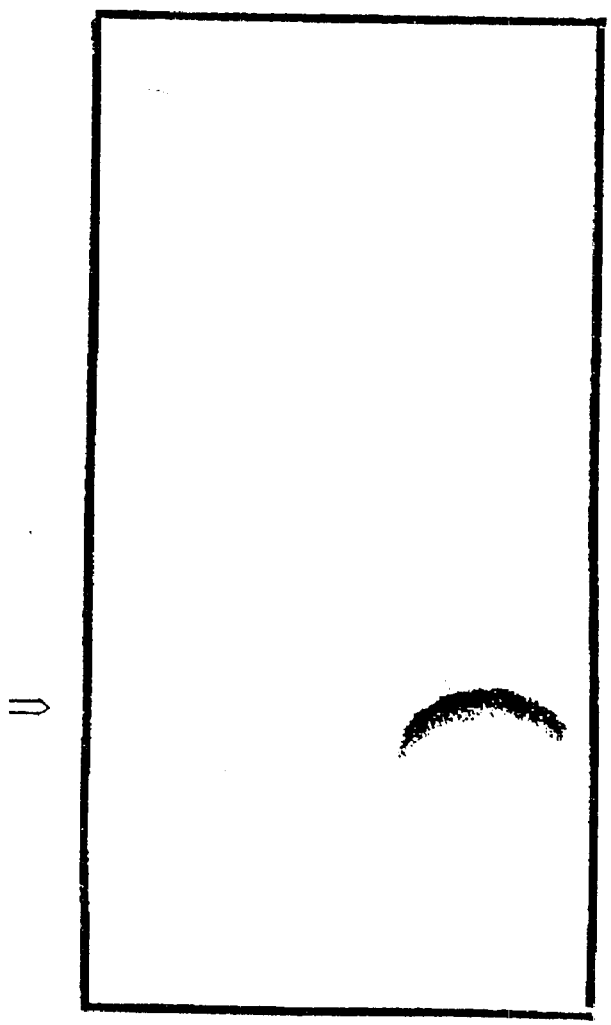

FIGS. 3A and 3B. Analysis of membrane Fraction B.
  A: Coomassie-blue stained 15% SDS-PAGE gel showing protein profiles of Fraction B (BF) prepared from cells from *B. burgdorferi* B31, *B. afzelii* ACA1 and *B. garinii* IP90.
  B: The corresponding Western Blot probed with the monoclonal antibody 15G6.
  Arrows indicate the position of 13 kDa protein. Mw—molecular weight standard, kD—kilodalton.

Figure 4A:
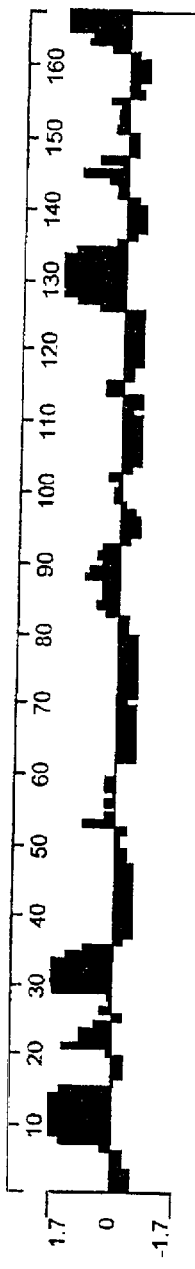
Figure 4:
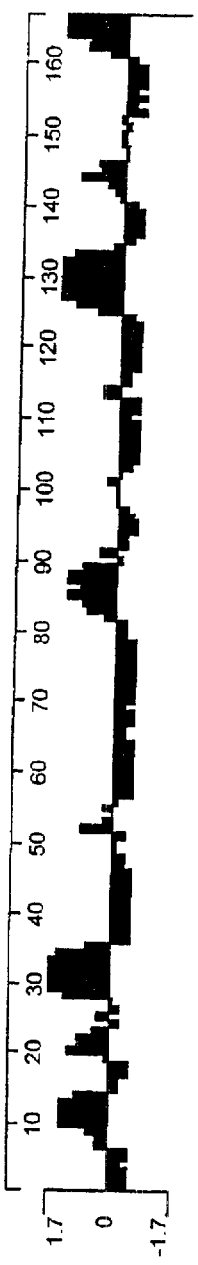
Figure 4:
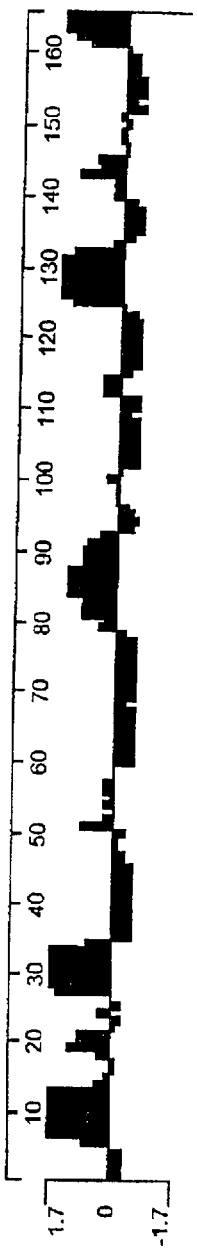

FIG. 4. Antigenicity plot.
  Antigenicity plot according to Jameson-Wolf of the deduced amino acid sequence of P13 from A) *B. burgdorferi* B31, B) *B. afzelii* ACA1 and C) *B. grainii* IP90.

Figure 5A:
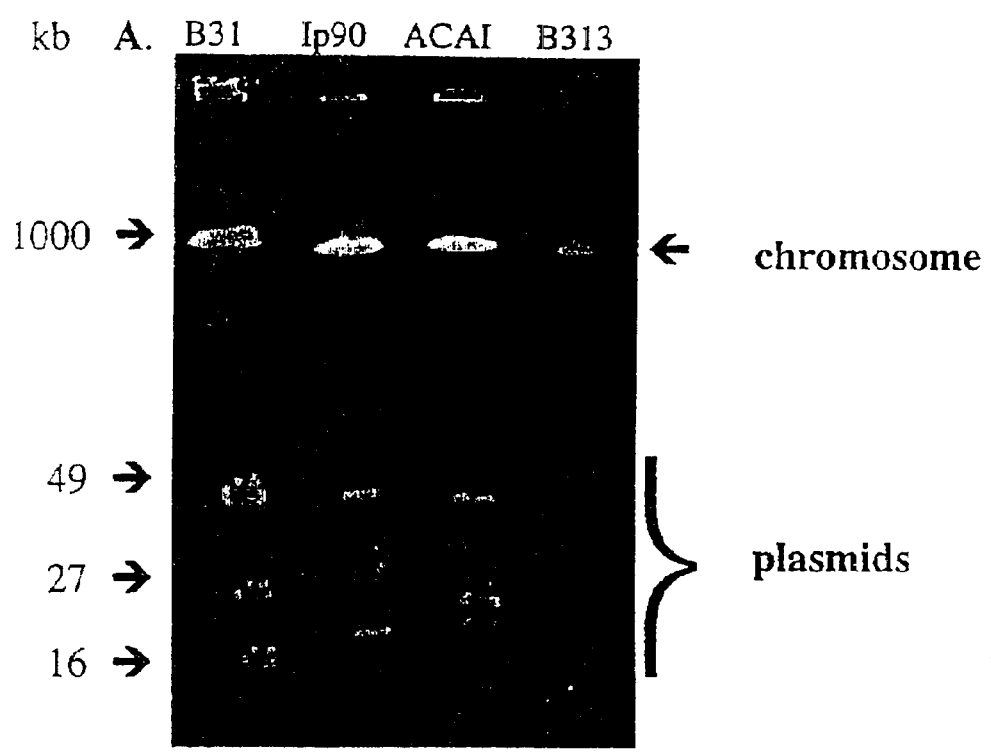
Figure 5B:
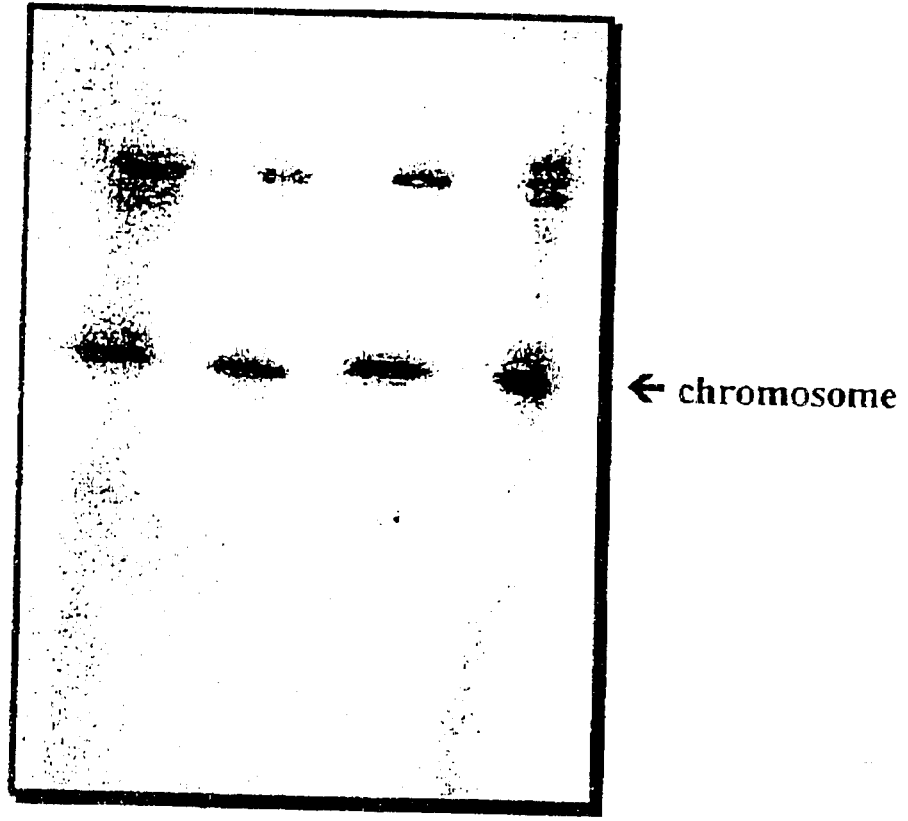

FIGS. 5A and 5B. Gene localisation analysis of the P13 gene.
  A: Separation of total DNA prepared from *B. burgdorferi* B31, *B. burgdorferi* B313, *B. afzelii* ACA1 and *B. grainii* IP90 by pulse-field agarose gel electrophoresis (AGE).
  B: The corresponding Southern blot using an $\alpha$-$^{32}$P labelled probe prepared by PCR amplification of a part of the P13 gene.

Figure 6:
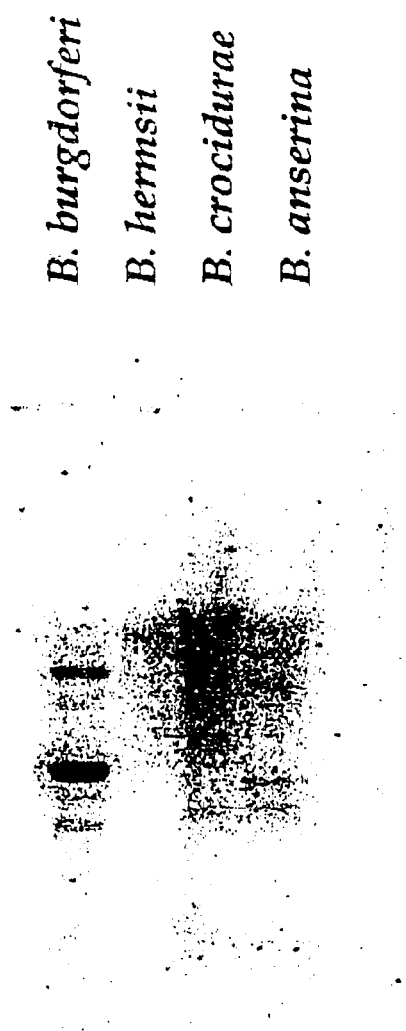

FIG. 6. Southern blot.
  Total DNA from *B. burgdorferi*, *B. hermsii*, *B. crocodurae*, and *B. anserina* was digested with EcoRI and separated by AGE. DNA was transferred to a Hybond-N membrane. The filter was probed with a PCR fragment obtained by amplification using primers Y9 (SEQ ID:7) and Y7R (SEQ ID:6). Hybridization temperature was 55° C. In general as described in section 9.2.

Figure 7A:
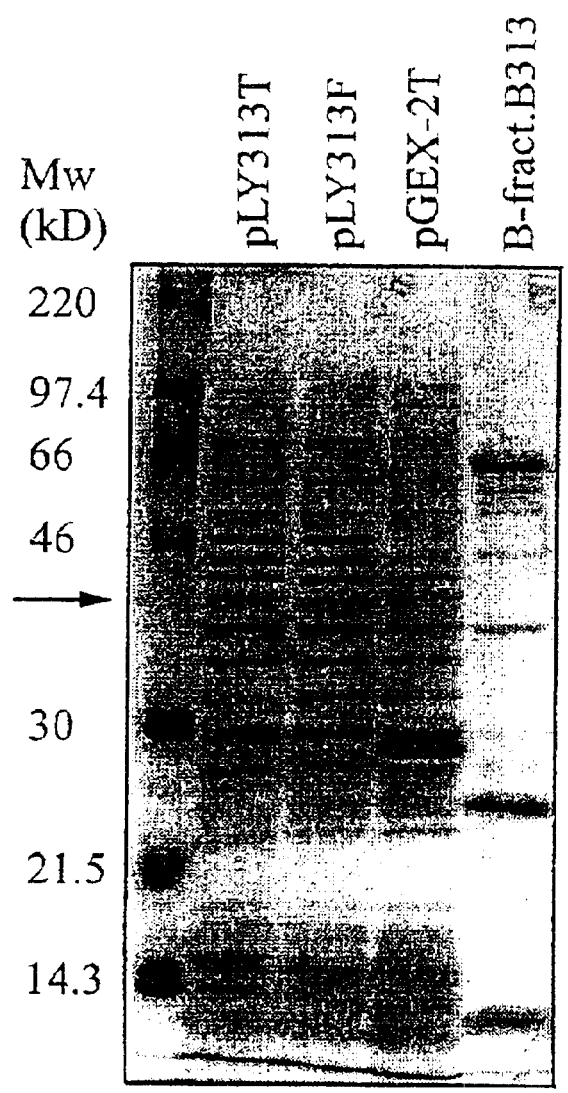
Figure 7B:
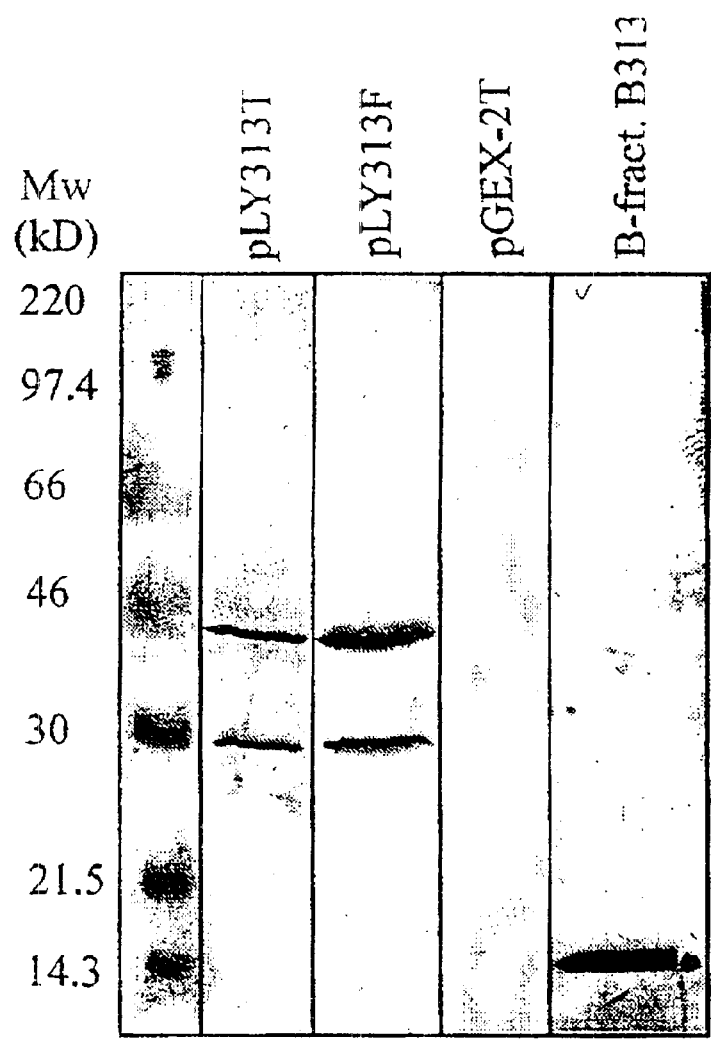

FIGS. 7A and 7B. Expression of recombinant P13 in *E. coli*.
  A: Coomassie-blue stained 15% SDS-PAGE gel showing protein profiles of whole cell lysates of *E. coli* transfected with plasmid pLY313F and plasmid pLY313T.
  B: The corresponding Western Blot probed with the monoclonal antibody 15G6. pGEX-2T, *E. coli* transfected with the control plasmid.

B-fract.B313, B-fraction prepared from *B. burgdorferi* B313.
Mw—molecular weight standard, kD—kilodalton.

Figure 8A:
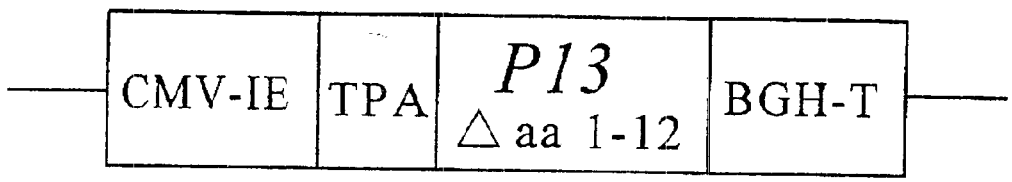
Figure 8B:
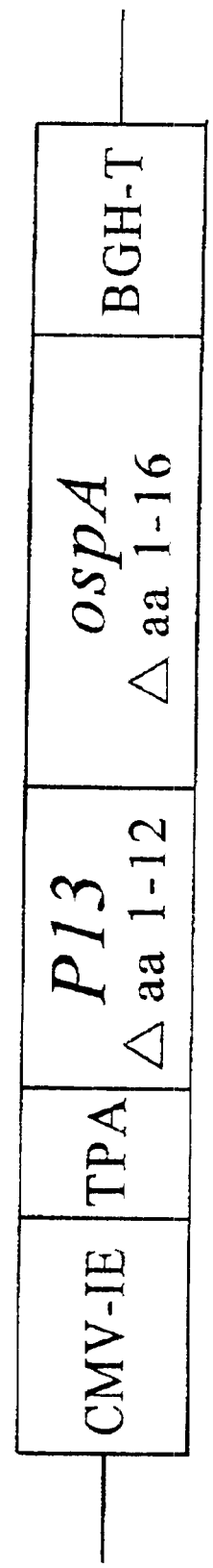

FIGS. 8A and 8B. Constructs for DNA vaccination.
  A: Schematic representation of the insert of plasmid pLY-H used in DNA vaccination for the expression of recombinant P13.
  B: Schematic representation of the insert of plasmid pLY-HA used in DNA vaccination for the expression of fusion of recombinant P13 and recombinant OspA.

Figure 9:
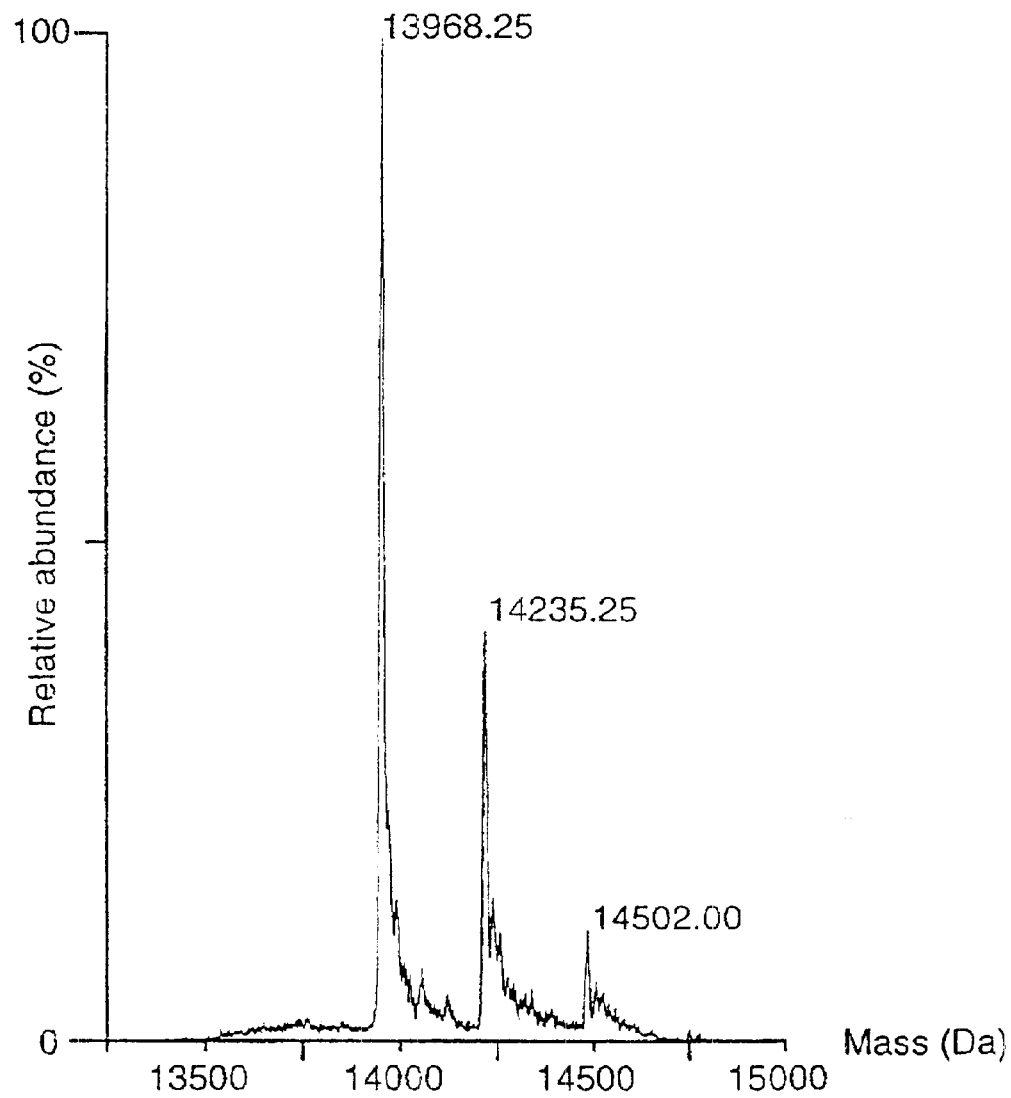

FIG. 9. Electron mass spectrum of purified P13 protein.
  The molecular masses of the three major components are indicated above the peaks.

DETAILED DESCRIPTION OF THE INVENTION

Nucleic Acid Fragments of the Invention

The present invention relates to the utility of Bb associated nucleic acid fragments as diagnostic or preventive tools in Lyme disease as well as for the preparation of P13 and useful P13 analogues.

In a first aspect the present invention therefore relates to an isolated nucleic acid fragment encoding a polypeptide fragment which exhibits a substantial immunological reactivity with a rabbit polyclonal antibody raised against a polypeptide having an apparent molecular weight of 13 kDa as determined by SDS-PAGE and subsequent visualization, said polypeptide being derived from *Borrelia burgdorferi* B313 and consisting of the amino acid sequence of SEQ ID NO: 19 or a post-translationally modified form thereof, said rabbit polyclonal antibody exhibiting substantially no immunological reactivity with proteins from at least 95% of spirochaetes randomly selected from the group consisting of *Borrelia hermsii*, *Borrelia crocidurae*, *Borrelia anserina*, and *Borrelia hispanica*.

By the term "nucleic acid fragment" as used herein is meant a fragment of DNA or RNA, but also of PNA (cf. Nielsen et al., 1991), having a length of at least two joined nucleotides. It will be understood that although the disclosed nucleic acid fragments of the present invention are DNA fragments, it may be desirable to employ an RNA fragment in e.g. a viral vector, the genome of which is natively composed of RNA. For the purposes of preparing e.g. probes for hybridization assays as described below, PNA fragments may prove useful, as these artificial nucleic acids have been demonstrated to exhibit very dynamic hybridization properties.

The term "a substantial immunological reactivity" is meant to designate a marked immunological binding between an antibody/antiserum on the one hand, and on the other hand an antigen, under well-defined conditions with respect to physicochemical parameters as well as concentrations of antigens and antibodies. Thus, a substantial immunological reactivity should be clearly distinguishable from a non-specific interaction between an antibody/antiserum and an antigen. This distinction can for instance be made by reacting the antibody/antiserum with a known concentration of an antigen which has previously been shown not to react with the antibody/antiserum, and then using this reaction as a negative control. A positive control could suitably be the reaction between the antibody/antiserum and the same concentration of the antigen used for the immunisation resulting in the production of the antibody/antiserum. In such an assay, an antigen resulting in a relative signal of at least 10% (calculated as $S_m \cdot (S_p - S_n) \cdot 100$, where $S_m$ is the measured signal, $S_p$ the positive control signal, and $S_n$ the negative control signal) is regarded as having a substantial immunological reactivity. An antigen exhibiting "substantially no immunological reactivity" is therefore defined as an antigen giving a signal of less than 10%.

By the terms "present" and "substantially absent", when referring to amino acid sequences and polypeptides in bacteria, is meant that the concentration of the amino acid sequence/polypeptide in a bacterium where it is "present" is at least 100 times higher than in a bacterium where it is substantially absent. However, it is preferred that the ratio of the concentrations are at least 1000, and more preferred at least 10,000, 100,000 or even higher. It is especially preferred that no concentration of the amino acid sequence/polypeptide can be observed in the bacterium from where it is substantially absent.

Although the data presented herein demonstrate that there is no cross-reactivity between antigens from *Borrelia hermsii, Borrelia crocidurae, Borrelia anserina,* or *Borrelia hispanica* and the disclosed polypeptides, it is conceivable that a few isolates of these bacteria will exhibit some cross-reactivity. As can be deduced from the above it is expected that the cross-reactivity will be less than 5% (since there is no reactivity with at least 95% of randomly chosen *Borrelia hermsii, Borrelia crocidurae, Borrelia anserina,* or *Borrelia hispanica*), and according to the invention this cross-reactivity may be even lower, such as at the most 4% and 3%, preferably at the most 2%, such as 1%. According to the invention the cross-reactivity is most preferred at most ½%, such as 0%. In such a case there will be no substantial immunological reactivity between the rabbit antiserum mentioned above and whole cell preparations of *Borrelia hermsii, Borrelia crocidurae, Borrelia anserina,* or *Borrelia hispanica.*

When using the term "cross-reactivity" is herein meant the phenomenon that two species exhibit a common feature which is detected in a reaction. In the present context the term cross-reactivity is used for similar reactions in antigen-antibody interactions as well as in hybridization interactions. Hence, the above-cited considerations concerning cross-reactivity of polypeptides apply for all cross-reactions between on the one hand the polypeptides/DNA fragments of the invention and on the other hand material from *Borrelia hermsii, Borrelia crocidurae, Borrelia anserina,* and *Borrelia hispanica;* this is also true for the quantitative assessment of whether cross-reactivity is present or not.

Nucleic acid fragments of the invention useful as hybridization probes and/or primers are not necessarily those fragments encoding immunologically useful polypeptides. Therefore the invention also relates to nucleic acid fragments which hybridise readily under highly stringent hybridization conditions with a DNA fragment having a nucleotide sequence selected from the group consisting of SEQ ID NO: 18, SEQ ID NO: 20, and SEQ ID NO: 22, or with a DNA fragment complementary thereto, but exhibit no substantial hybridization when the hybridization conditions are highly stringent with genomic DNA from at least 95% of spirochaetes randomly selected from the group consisting of *Borrelia hermsii, Borrelia crocidurae, Borrelia anserina,* and *Borrelia hispanica.* The term "highly stringent" when used in conjunction with hybridization conditions is as defined in the art, i.e. 5–10° C. under the melting point $T_m$, cf. Sambrook et al, 1989, pages 11.45–11.49.

Interesting nucleic acid fragments of the invention encode a polypeptide fragment comprising an amino acid sequence comprised in a polypeptide, said polypeptide being present in whole cell preparations of *Borrelia burgdorferi* B31, *Borrelia burgdorferi* B313, *Borrelia garinii* IP90, and/or *Borrelia afzelii* ACAI but being substantially absent from whole cell preparations of at least 95% of randomly selected *Borrelia hermsii, Borrelia crocidurae, Borrelia anserina,* or *Borrelia hispanica.* It is preferred that said polypeptide is a protein having an apparent molecular weight of 13 kDa, and it is still more preferred that the encoded polypeptide fragment comprises at least one epitope (such as at least 2, 3, 4, 5, 6, 7, 8, 9, 10, 11, 12, 13, 14, 15, 16, 17, 18, 19, 20, or at least 25 epitopes) being present in whole cell preparations of *Borrelia burgdorferi* B31, *Borrelia burgdorferi* B313, *Borrelia garinii* IP90, or *Borrelia afzelii* ACAI but being substantially absent from whole cell preparations of at least 95% of randomly selected *Borrelia hermsii, Borrelia crocidurae, Borrelia anserina,* and *Borrelia hispanica.* This at least one epitope is preferably one from a protein having an apparent molecular weight of 13 kDa.

By the terms "epitope" and "epitopic region" is meant the spatial part of an antigen responsible for the specific binding to the antigen-binding part of an antibody. It goes without saying that the identification of epitopes of the disclosed antigens will facilitate the production of polypeptides which exhibit marked antigenicity thus making them interesting with respect to diagnosis of Borreliosis and vaccination against infections with Bb; identification of epitopes has been discussed above.

Preferred nucleic acid fragments of the invention are DNA fragments, especially those which have nucleotide sequences with a sequence identity of at least 70% with SEQ ID NO: 18, SEQ ID NO: 20, or SEQ ID NO: 22 or with subsequences thereof of at least 12 nucleotides. However, the degree of sequence identity may be even higher such as at least 75%, 80%, 85%, 87%, and 89%. It is preferred that the degree of sequence identity is at least 90%, such as 92%, 94% or 95%, and especially preferred are DNA fragments with a sequence identity of at least 96% with SEQ ID NO: 18, SEQ ID NO: 20, or SEQ ID NO: 22. Especially for high accuracy hybridization assays, a total sequence identity is necessary, and therefore preferred. Other preferred nucleotide acid fragments of the invention are those which encode a polypeptide of the invention (cf. the below discussions concerning these polypeptides and their degree of sequence identity with the amino acid sequences disclosed herein) which has an amino acid sequence exhibiting a sequence homology of at least 50% with SEQ ID NO: 19, SEQ ID NO: 21, or SEQ ID NO: 23 or with subsequences thereof having a length of at least 10 amino acid residues. Also the sequence identity of the encoded polypeptide fragment is preferably higher, such as at least 60%, at least 70%, at least 75%, at least 80%, at least 85%, at least 90%, at least 92%, at least 94%, at least 95%, and at least 96%.

The term "identity" is, with respect to nucleotide fragments such as DNA fragments, intended to indicate the identity between the nucleotides in question between which the identity is to be established, in the match with respect to nucleotide composition and position in the DNA fragments. With respect to polypeptides and fragments thereof described herein, the term means an identity between the amino acids in question between which the homology is to be established, in the match with respect to amino acid composition and their position in the polypeptides. The term "sequence identity" thus indicates a quantitative measure of the degree of homology between two amino acid sequences or between two nucleotide sequences of equal length: The sequence identity can be calculated as $$\frac{(N_{ref} - N_{dif})100}{N_{ref}}1,$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}$=2 and $N_{ref}$=8).

Considerations similar to those given above for the immunological reactivity and cross-reactivity of antigens can be applied for the distinction between a nucleic acid fragment which "hybridizes readily" and a fragment which "exhibits substantially no hybridization" under high stringency conditions; i.e. a nucleic acid which hybridizes readily should exhibit at least 10% of a true positive signal.

As discussed in the examples, putative epitopes have been identified in the P13 protein sequences. Therefore, especially preferred nucleic acid fragments of the invention are those comprising a sequence encoding a polypeptide which comprises at least one amino acid sequence selected from the group consisting of amino acid residues 19–27, 33–36, 41–47, 95–104, 138–147 and 174–179 in SEQ ID NO: 19; amino acid residues 19–26, 32–35, 40–47, 94–101, 137–146, and 174–178 in SEQ ID NO: 21; and amino acid residues 18–26, 30–33, 39–46, 91–104, 137–145 and 173–177 in SEQ ID NO: 23, all of which have been identified as putative epitopic regions.

Highly preferred nucleic acid fragments are those which encode mature P13, i.e. nucleic acid fragments which encode a protein having an apparent molecular weight of 13 kDa which is present in whole cell preparations of *Borrelia burgdorferi* B31, *Borrelia burgdorferi* B313, *Borrelia garinii* IP90, or *Borrelia afzelii* ACAI but which is substantially absent from whole cell preparations of at least 95% of randomly selected *Borrelia hermsii, Borrelia crocidurae, Borrelia anserina,* and *Borrelia hispanica.* Since this 13 kDa protein has been demonstrated in fraction B of Bb, it is preferred that this encoded protein is present in fraction B from Borrelia burgdorferi B31, *Borrelia burgdorferi* B313, *Borrelia garinii* IP90, or *Borrelia afzelii* ACAI.

Analysis of the effects of exposure of whole Bb cells to proteinase K has now demonstrated that such Bb cells lose their reactivity with antibodies against the 13 kDa polypeptide and that fraction B of Bb cells are devoid of the 13 kDa protein. Hence, it must be concluded that P13 is a surface exposed polypeptide in Bb, and therefore preferred nucleic acid fragments are those which encode a surface exposed protein of *Borrelia burgdofferi* B31, *Borrelia burgdofferi* B313, *Borrelia garinii* IP90, or *Borrelia afzelii* ACAI.

Highly preferred embodiments of the nucleic acid fragments of the invention comprise a nucleotide sequence encoding a polypeptide fragment which includes an amino acid sequence selected from the group consisting of SEQ ID NOs: 19, 21, and 23, and of these, those which comprise a nucleotide sequence selected from the group consisting of SEQ ID NOs: 18, 20, and 22 are especially preferred. Most preferred nucleic acid fragments of the invention are those which consist of a nucleotide sequence encoding a polypeptide fragment consisting of an amino acid sequence selected from the group consisting of SEQ ID NOs: 19, 21, and 23, and the three most preferred are those which consist of the nucleotide sequence selected from the group consisting of SEQ ID NOs: 18, 20, and 22.

Analogues of the disclosed nucleic acid fragments which also form part of the invention are nucleic acid fragments which are fused to at least one other nucleic acid fragment which encodes a fusion partner. This fusion partner can be a protein enhancing the immunogenicity of the fused protein relative to a protein without the encoded fusion partner. Such encoded proteins may e.g. be lipoproteins, e.g. the outer membrane lipoprotein from *E. coli* and OspA from *Borrelia burgdorferi sensu lato;* viral proteins, e.g. from Hepatitis B surface antigen, Hepatitis B core antigen, and the influenza virus non-structural protein NS1 (cf. EP-A-0 366 238 and WO 88/01875); immunoglobulin binding proteins, e.g. protein A, protein G, and the synthetic ZZ-peptide (cf. EP-A-0 243 333 and U.S. Pat. No. 5,411,732); T-cell epitopes; or B-cell epitopes.

Other nucleic acid fragments to form part of a nucleic acid fragment of the invention encoding a fusion polypeptide are those encoding polypeptides which facilitate expression and/or purification of the fused peptide. Such encoded polypeptides could, according to the invention, be bacterial fimbrial proteins, e.g. the pilus components pilin and papA; protein A; the ZZ-peptide; the maltose binding protein; glutathione *S-transferase;* β-galactosidase; calmodulin binding protein; or poly-histidine.

Other nucleic acid fragments to form part of a nucleic acid fragment of the invention encoding a fusion polypeptide are those encoding polypeptides which facilitate modulation in drug resistance of the host thereby facilitating selection of the host harbouring the plasmid. Such hosts could, according to the invention, be a bacterium, a yeast, a protozoan, or a cell derived from a multicellular organism selected from a fungus, an insect cell, a plant cell, and a mammalian cell.

Of course, also fusion partners derived from P13 are interesting and these could be those which have the same amino acid sequence as at least one amino acid sequence selected from the group consisting of amino acid residues 19–27, 33–36, 41–47, 95–104, 138–147 and 174–179 in SEQ ID NO: 19; amino acid residues 19–26, 32–35, 40–47, 94–101, 137–146, and 174–178 in SEQ ID NO: 21; and amino acid residues 18–26, 30–33, 39–46, 91–104, 137–145 and 173–177 in SEQ ID NO: 23.

It will be understood from the above that various analogues and subsequences of the nucleic acids disclosed in the sequence listing herein are interesting aspects of the invention, as are nucleic acid fragments encoding fused polypeptides including polypeptides encoded by nucleic acid fragments of the invention.

The term "analogue" with regard to the nucleic acid fragments of the invention is intended to indicate a nucleotide sequence which encodes a polypeptide identical or substantially identical to a polypeptide encoded by a nucleic acid fragment of the invention (SEQ ID NOs: 18, 20, and 22).

It is well known that the same amino acid may be encoded by various codons, the codon usage being related, inter alia, to the preference of the organisms in question expressing the nucleotide sequence. Thus, one or more nucleotides or codons of a nucleic acid fragment of the invention may be exchanged by others which, when expressed, result in a polypeptide identical or substantially identical to the polypeptide encoded by the nucleic acid fragment in question.

Also, the term "analogue" is used in the present context to indicate a nucleic acid fragment or a nucleic acid sequence of a similar nucleotide composition or sequence as the nucleic acid sequence encoding the amino acid sequence having the immunological properties discussed above, allowing for minor variations which do not have an adverse effect on the biological function and/or immunogenicity as compared to the disclosed polypeptides, or which give interesting and useful novel binding properties or biological functions and immunogenicities etc. of the analogue. The analogous nucleic acid fragment or nucleic acid sequence may be derived from an animal or a human or may be partially or completely of synthetic origin as described herein. The analogue may also be derived through the use of recombinant nucleic acid techniques.

Furthermore, the terms "analogue" and "subsequence" are intended to allow for variations in the sequence such as substitution, insertion (including introns), addition, deletion and rearrangement of one or more nucleotides, which variations do not have any substantial effect on the polypeptide encoded by a nucleic acid fragment or a subsequence thereof. The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence whether at either end of the sequence or at any suitable point within it, and "rearrangement" is intended to mean that two or more nucleotide residues have been exchanged with each other.

Polypeptide Fragments of the Invention

The present invention relates to the utility of Bb associated antigenic proteins as diagnostic or preventive tools in Lyme disease. Proteins have been indentified as associated only (or predominantly) with virulent isolates of Bb, providing a basis for several types of diagnostic tests for Lyme disease, including immunodiagnostic and nucleic acid identification, such as those based on amplification procedures. All these embodiments rely on the availability of the P13 proteins and their analogues.

Another part of the invention therefore pertains to a polypeptide fragment which exhibits a substantial immunological reactivity with a polyclonal rabbit antibody raised against a polypeptide having an apparent molecular weight of 13 kDa as determined by SDS PAGE, followed by visualization, and being derived from *Borrelia burgdorferi* B313, said polypeptide comprising the amino acid sequence 1–167 of SEQ ID NO: 19, said polyclonal rabbit antibody exhibiting substantially no immunological reactivity with whole cell preparations from at least 95% of randomly selected *B. hermsii, B. crocidurae, B. anserina,* or *B. hispanica*, with the proviso that said polypeptide is essentially free from other Borrelia-derived antigens when it is identical in amino acid sequence to a 13 kDa surface exposed polypeptide which can be extracted from *Borrelia burgdorferi sensu lato.*

As mentioned above, the 13 kDa polypeptide has previously been identified in SDS gels. However, the 13 kDa polypeptide has never been purified to homogeneity, let alone been cloned and sequenced. The present invention is therefore the first to provide the 13 kDa polypeptide in a form which is totally free from contaminating and potentially harmful (for e.g. vaccine purposes) Borrelia antigens, i.a. the 13 kDa polypeptide in a substantially pure form. The present invention is also the first to provide useful variants of the 13 kDa polypeptide (such variants including subsequences of the polypeptide as well as analogues wherein changes have been made to the native amino acid sequence). It should be noted that it is highly problematic to purify the native 13 kDa antigen to homogeneity since it is a membrane protein; it is well-known to the skilled person in protein purification that membrane proteins present special problems. However, upon the provision of recombinant or synthetic P13 as disclosed herein, it has become possible to readily prepare P13 in a form free of other Borrelia antigens and it has also become possible to prepare variants of P13 which were not available without access to knowledge of the genetic material encoding the protein.

The polypeptide fragment of the invention is otherwise precisely as described above when discussing the nucleic acid fragments of the invention and all discussions pertaining to polypeptide fragments encoded by the nucleic acid fragments of the invention apply mutatis mutandis to the polypeptide fragments of the invention. Hence, all considerations regarding the presence or absence of the polypeptide fragments and their epitopes in various borrelial species as well as other considerations, apply to the polypeptide fragments of the invention.

Therefore, also analogues of the P13 polypeptides of the invention are embraced by the present invention. When using the terms "analogue" and "subsequence" in connection with polypeptides is meant any polypeptide having the same immunological characteristics as the polypeptides of the invention described above with respect to the ability to confer an equivalent and increased resistance to infections with *Borrelia burgdorferi sensu lato* through immune responses against P13. Thus, included is also a polypeptide from different sources, such as other bacteria or even from eukaryotic cells.

The terms "analogue" and "subsequence" with regard to a polypeptide of the invention are also used in the present context to indicate a protein or polypeptide of a similar amino acid composition or sequence as the characteristic amino acid sequences shown in SEQ ID NOs: 19, 21 and 23, allowing for minor variations which do not have an adverse effect on the ligand binding properties and/or biological function and/or immunogenicity, or which may give interesting and useful novel binding properties or biological functions and immunogenicities etc. The analogous polypeptide or protein may be derived from other microorganisms, cells, or animals and the analogue may also be derived through the use of recombinant DNA techniques as described herein.

The invention also comprises polypeptides which can be the product of post-translational modifications of the polypeptides of the invention described above. By the term "post-translational modification" with regard to a polypeptide of the invention is meant any modification or processing of the full-length polypeptide that can occur during the production of the peptides in Bb, or in the case of recombinant polypeptides in the production of the polypeptides in a host cell. These modifications include, but are not limited to, the processing by various peptidases, such as signal peptidases, and modifications such as glycosylations, phosphorylations, acetylations, formylations, acylations, palmitylations, sulphations and lipidations.

Furthermore, in the present context the term "immunologically equivalent" means that the analogue or subsequence of the polypeptide is functionally equivalent to the polypeptide with respect to the ability of evoking a protective immune response against *Borrelia burgdorferi sensu lato* infections.

The term "protective immune response" has its usual meaning, i.e. that the immune response evoked by the polypeptide in question protects the person immunized from contracting Lyme disease, or that the immune response evoked by the polypeptide at least confers a substantially increased resistance to infections with *Borrelia burgdorferi sensu lato.*

Finally, also fusion polypeptides as described above are part of the invention and this is also true for all considerations relating to fusion partners etc. which are discussed above when dealing with the nucleic acid fragments of the invention.

Vectors, Host Cells and Cell Lines of the Invention

Having provided the genetic information relating to the P13 proteins, the invention also allows for the preparation of P13 and variants thereof by means of genetic engineering. Useful tools in this connection are cloning and expression vectors and therefore another important part of the invention is a non-borrelial vector carrying the nucleic acid fragment according to the invention and described in detail above. Such a vector of the invention is preferably capable of autonomous replication. Preferred vectors are selected from the group consisting of a plasmid, a phage, a cosmid, a mini-chromosome, and a virus.

Even though plasmid vectors are often preferred because of their relative ease of use, vectors which, when introduced in a host cell, are integrated in the host cell genome are especially preferred due to the increased stability of the obtained transformed cells.

In view of the discussion below, a preferred vector of the invention comprises, in the 5'→3' direction and in operable linkage, a promoter for driving expression of the nucleic acid fragment of the invention, a nucleic acid sequence encoding a leader peptide enabling secretion of or integration into the membrane of the polypeptide, the nucleic acid fragment according to the invention, and a nucleic acid sequence encoding a terminator. It is preferred that the promoter drives expression in a eukaryotic cell and also that the leader peptide enables secretion from or integration into the membrane of a mammalian cell.

The invention also relates to a transformed cell carrying the vector of the invention and capable of replicating the nucleic acid fragment according to the invention. Such a transformed cell is preferably a microorganism selected from a bacterium, a yeast, a protozoan, or a cell derived from a multicellular organism selected from a fungus, an insect cell, a plant cell, and a mammalian cell. Especially preferred host cells are bacteria of the genera Escherichia, Bacillus or Salmonella. *E. coli* is preferred. Host cells which are capable of mediating a post-translational modification important for the biological function of the polypeptide of the invention are also a part of the invention.

For the purposes of production of recombinant P13 and variants thereof, a stable cell line is preferred and therefore the invention also relates to a stable cell line producing the polypeptide of the invention, which carries a vector of the invention, and which expresses the nucleic acid fragment of the invention.

In general, of course, prokaryotes are preferred for the initial cloning of DNA sequences and constructing the vectors useful in the invention. For example, in addition to the particular strains mentioned in the specific disclosure below, one may, by way of example, mention strains such as *E. coli* K12 strain 294 (ATCC No. 31446), *E. coli* B, and *E. coli* X 1776 (ATCC No. 31537). These examples are, of course, intended to be illustrative rather than limiting.

Prokaryotes are preferred for expression. The aforementioned strains, as well as *E. coli* W3110 (F-, lambda-, prototrophic, ATCC No. 273325), bacilli such as *Bacillus subtilis,* or other enterobacteriaceae such as *Salmonella typhimurium* or *Serratia marcescens,* and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid or another microbial plasmid or phage must also contain, or be modified to contain, promoters which can be used by the microorganism for expression.

The promoters most commonly used in recombinant DNA construction include the β-lactamase (penicillinase) and lactose promoter systems (Chang et al., 1978; Itakura et al., 1977; Goeddel et al., 1979) and a tryptophan (trp) promoter system (EP-B-0 036 776). While these are the most commonly used, other microbial promoters have been discovered and utilised, and details concerning their nucleotide sequences have been published, enabling a skilled worker to ligate them functionally with plasmid vectors (Siebenlist et al., 1980). Certain genes from prokaryotes may be expressed efficiently in *E. coli* from their own promoter sequences, thus avoiding the need for addition of another promoter by artificial means.

In addition to prokaryotes, eukaryotic microbes, such as yeast cultures may also be used. *Saccharomyces cerevisiae,* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschumper et al., 1980). This plasmid already contains the trpI gene which provides a selection marker for a mutant strain of yeast lacking the ability to grow in tryptophan, for example ATCC No. 44076 or PEP4-1 (Jones, 1977). The use of the trpI lesion as a characteristic of the yeast host cell genome then provides an effective environment for detecting transformation by growth in the absence of tryptophan.

Suitable promoting sequences in yeast vectors include the promoters for 3-phospho-glycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilisation. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BgII site located in the viral origin of replication. Further, it is also possible, and often desirable, to utilise promoter or control sequences normally associated with the desired gene sequence, provided such control sequences are compatible with the host cell systems.

An origin of replication may be provided either by construction of the vector to include an exogenous origin, such as may be derived from SV40 or other viruses (e.g., Polyoma, Adeno, VSV, BPV) or may be provided by the host cell chromosomal replication mechanism. If the vector is integrated into the host cell chromosome, the latter is often sufficient.

Methods of producing the polypeptides of the invention which are themselves part of the invention thus comprise the following steps:

culturing a transformed cell or a stable cell line according to the invention under conditions facilitating the expression of the polypeptide by the cell or cell line, and harvesting the polypeptide, and optionally subjecting the polypeptide to post-translational modification(s);

or, alternatively, synthesising the polypeptide by solid-phase peptide synthesis or by liquid-phase peptide synthesis.

The latter approach is preferred with the present technology when the polypeptide fragment is relatively short, but of course it cannot be excluded that these techniques will ultimately be refined so as to allow feasible production of longer fragments.

The need for post-translational modifications exists because certain polypeptides are prepared in the above-described manner lacking for instance a fatty-acylation of an amino acid residue, or the polypeptide has for some reason been prepared in an elongated version which should be cleaved before the polypeptide will prove functional. The optional post-translational modifications thus preferably involve lipidation or glycosylation when these modifications have not been accomplished by means of the preparative procedure itself. Applicable methods for accomplishing lipidation and/or glycosylation are well-known to the skilled person. Other post-translational modifications include cleavage or elongation of the obtained product. In some instances, the host cell or cell line also processes the translation product so as to obtain a processed polypeptide.

Preparation of Useful Variants of P13

The present invention has addressed the cloning of nucleic acids encoding certain antigenic polypeptides related to the P13 proteins.

A method of preparing variants of the P13 antigens is site-directed mutagenesis. This technique is useful in the preparation of individual peptides, or biologically functional equivalent proteins or peptides, derived from the P13 antigen sequences, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phages are readily commercially available and their use is generally well known to those skilled in the art.

In general, site-directed mutagenesis in accordance herewith is performed by first obtaining a single-stranded vector which includes within its sequence a DNA sequence which encodes the P13 antigens. An oligonucleotide primer bearing the desired mutated sequence is prepared, generally synthetically, for example by the method of Crea et al. (1978). This primer is then annealed with the single stranded vector, and subjected to DNA polymerising enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected P13 genes using site-directed mutagenesis is provided as a means of producing potentially useful species of the P13 genes and is not meant to be limiting as there are other ways in which sequence variants of the P13 genes may be obtained. For example, recombinant vectors comprising the desired P13 genes may be treated with mutagenic agents to obtain sequence variants (see, e.g., a method described by Eichenlaub, 1979) for the mutagenesis of plasmid DNA using hydroxylamine.

Further, another embodiment of the invention is a nucleic acid fragment substantially identical to a nucleic acid fragment of the invention which can be provided e.g. by dual hybridisation. This method employs a nucleic acid fragment which specifically hybridizes under stringency hybridization conditions to a complementary nucleic acid fragment which in turn specifically hybridizes under stringency hybridization conditions to a third nucleic acid fragment encoding a polypeptide comprising the amino acid sequences of the invention. This third nucleic acid fragment will thus be substantially identical to initial nucleic acid fragment.

Vaccine Preparation and Use

Part of the present invention contemplates vaccine preparation and use. General concepts related to methods of preparation and use are discussed as applicable to preparations and formulations with the disclosed P13 antigens, its epitopes and subfragments thereof. In general, a vaccine of the invention comprises an amount of a polypeptide of the invention or produced according to the invention, said amount being effective to confer substantially increased resistance to infections with *Borrelia burgdorferi sensu lato* in an animal, including a human being, the polypeptide being formulated in combination with a pharmaceutically acceptable carrier, diluent or vehicle and the vaccine optionally further comprising an adjuvant. Further, the vaccine is generally used in a method of immunizing an animal, including a human being, against infections with *Borrelia burgdorferi sensu lato,* the method comprising administering an immunogenically effective amount of the vaccine to the animal.

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. In general terms, the preparation of the vaccines of the invention is accomplished by admixing a polypeptide of the invention or prepared by the method thereof, and a pharmaceutically acceptable carrier, vehicle, or diluent, and optionally an adjuvant.

Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts include acid addition salts (formed with the free amino groups of the peptide) which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such an amount as will be therapeutically effective and immunogenic. The quantity to be administered depends on the subject to be treated, including, e.g., the capacity of the individual's immune system to synthesise antibodies, and the degree of protection desired. Precise amounts of active ingredient required to be administered depend on the judgement of the practitioner. However, suitable dosage ranges are of the order of several hundred micrograms of active ingredient per vaccination. For example, suitable dosages can be in the range of 1–1000 $\mu$g, such as between 2 and 750 $\mu$g, between 5 and 500 $\mu$g, between 7.5 and 250 $\mu$g, between 10 and 150 $\mu$g, between 10 and 100 $\mu$g, between 10 and 75 $\mu$g, and between 10 and 50 $\mu$g. Suitable regimes for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine include use of agents such as aluminium hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° C. and 101° C. for 30 second to 2 minute periods, respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. The adjuvant is preferably selected from the group consisting of dimethyldioctadecylammonium bromide (DDA), Quil A, poly I:C, Freund's incomplete adjuvant, IFN-$\gamma$, IL-2, IL-12, monophosphoryl lipid A (MPL), and muramyl dipeptide (MDP).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain levels of the antibodies. The course of the immunisation may be followed by assays for antibodies for the supernatant antigens. The assays may be performed by labelling with conventional labels, such as radionuclides, enzymes, fluorescers, and the like. These techniques are well known and may be found in a wide variety of patents, such as U.S. Pat. Nos. 3,791,932; 4,174,384 and 3,949,064, which are illustrative of these types of assays.

The polypeptide of the invention can also be part of a multi-component or combination vaccine, which is also an important part of the invention. Such a vaccine contains
  an amount of the polypeptide fragment of the invention or of a polypeptide fragment prepared according to the invention, the amount of the polypeptide fragment being effective to confer substantially increased resistance to infections with Borrelia burgdorferi sensu lato in an animal, including a human being; and
  at least one further Borrelia antigen,
the polypeptide fragment and the antigen being formulated in combination with a pharmaceutically acceptable carrier, vehicle, or diluent and the vaccine optionally further comprising an adjuvant. All components of such a vaccine apart from the at least one further Borrelia antigen are as described in detail herein. With respect to the at least one further Borrelia antigen, it is preferred that it is selected from the group consisting of OspA, OspB, OspC, OspD, OspE, OspF, OspG, PC, Oms28, Oms45, Oms 66, decorin binding protein (dbp), LpLA7, EppA, T5, Si, 26 kDa, 39 kDa, 66 kDa, 79 kDa, 85 kDa, and 110 kDa antigen.

Another variant of a combination vaccine of the invention comprises at least two non-identical polypeptide fragments of the present invention or at least two non-identical polypeptide fragments prepared by the method of the invention, the vaccine comprising an amount of the polypeptides effective to confer substantially increased resistance to infections with Borrelia burgdorferi sensu lato in an animal, including a human being, in combination with a pharmaceutically acceptable carrier, vehicle, or diluent, the vaccine optionally further comprising an adjuvant. Also in this case, all components of the vaccine have been described elsewhere herein.

Another known way of achieving a suitable immune response in a vaccinated animal is by employing a so-called live vaccine which i.a. triggers both a B- and a T-cell mediated immune response, and therefore the invention also pertains to such a vaccine comprising a non-pathogenic microorganism carrying and being capable of expressing the nucleic acid fragment of the invention so as to produce the polypeptide of the invention, the live vaccine being effective in conferring increased resistance to infection with Borrelia burgdorferi sensu lato in an animal, including a human being. Preferred non-pathogenic microorganisms are selected from the group consisting of Mycobacterium bovis BCG, Salmonella typhi, Salmonella typhimurium, Salmonella paratyphi, Staphylococcus aureus, and Listeria monocytogenes.

DNA Vaccination

The invention also contemplates the use of disclosed nucleic acid segments in the construction of expression vectors or plasmids and use in host cells with a view to vaccination of the individual housing the host cells. Hence, the invention also pertains to a vaccine comprising a nucleic acid fragment or a vector of the invention, the vaccine effecting in vivo expression of antigens by an animal, including a human being, to whom the vaccine has been administered, the amount of expressed antigens being effective to confer substantially increased resistance to infections with Borrelia burgdorferi sensu lato in an animal, including a human being. The related vaccination method consists of administering an amount of this vaccine which is effective to confer an increased resistance to such infections upon the mammal to which it has been administered.

The following is a general discussion relating to such use of nucleic acid fragments and the particular considerations in practising this aspect of the invention.

Direct injection of plasmid DNA has become a simple and effective method of vaccination against a variety of infectious diseases (see, e.g., Ulmer et al., 1993). It is potentially more potent and longer lasting than recombinant protein vaccination because it elicits both a humoral as well as a cellular immune response.

The present invention also provides for a DNA-based vaccine or immunological composition against Lyme disease (e.g., Borrelia burgdorferi, afzelii, or garinii) which can elicit an immunological response, which can confer protection, even up to 100%, in mice against challenge with an infectious strain of Borrelia burgdorferi. An exemplary plasmid of the invention contains the human cytomegalovirus immediate early promoter driving expression of the P13 protein. To facilitate expression in eukaryotic cells, the natural leader sequence of the gene encoding P13 has been replaced with the human tissue plasminogen activator leader sequence.

Protection can be demonstrated in mice by injecting, intramuscularly, naked plasmid DNA and subsequently challenging with Bb spirochaetes. Following vaccination sera will contain high titers of antibody to P13 which will inhibit spirochaete growth in vitro.

Thus, a DNA vaccine or immunological composition, expressing a P13 antigen, from Borrelia burgdorferi, Borrelia afzelii or Borrelia garinii or any combination thereof, can protect mice against infection by a Borrelia genospecies, the etiologic agent of Lyme disease. The composition is thus useful for eliciting a protective response in a host susceptible to Lyme Disease, as well as for eliciting antigens and antibodies, which are also useful in and of themselves.

Therefore, as discussed above, the invention in a general sense preferably provides methods for immunising, or vaccinating, or eliciting an immunological response in a host, such as a host susceptible to Lyme disease, e.g., a mammalian host, against Borrelia and accordingly Lyme Disease, by administering DNA encoding a P13 antigen, for instance DNA encoding P13 from Borrelia burgdorferi, Borrelia afzelii, Borrelia garinii antigen or combinations thereof, in a suitable carrier or diluent, such as saline; and the invention provides plasmids and compositions for performing the method, as well as methods for making the plasmids, and uses of the expression products of the plasmids, as well as antibodies elicited thereby.

From present dog and human trials based on efficiency studies with mice (Erdile et al., 1993; U.S. Ser. No. 08/373, 455), it is clear that mice are now a suitable animal model with respect to Borrelia and Lyme disease for extrapolation to domestic animals, humans, and other animals susceptible to Lyme disease or Borrelia infection (e.g., wild animals such as deer).

In the present invention, the DNA encoding P13 or an immunologically active fragment thereof can be administered in dosages and by techniques well known to those skilled in the medical or veterinary arts taking into consideration such factors as the age, sex, weight, species and condition of the particular patient, and the route of administration. DNA encoding P13 or an immunologically active fragment thereof can be administered alone, or can be co-administered or sequentially administered with other Bb antigens, or with DNA encoding other Bb antigens; and the DNA encoding P13 or an immunologically active fragment thereof can be sequentially administered, e.g., each spring as the "Lyme Disease season" is about to begin.

As broadly discussed above, the invention also pertains to plasmids comprising DNA including P13 encoding DNA for expression by eukaryotic cells. The DNA, from upstream to downstream (5' to 3'), can comprise: DNA encoding a promoter for driving expression in eukaryotic cells, DNA encoding a leader peptide which enables secretion of a prokaryotic protein sequence from a mammalian cell, DNA encoding a P13 antigen (or antigens) or an immunologically active fragment thereof, DNA encoding other Bb antigens such as OspA, OspB, OspC or OspD or an immunologically active fragment thereof, and DNA encoding a terminator.

For instance, the promoter can be a eukaryotic viral promoter such as a herpes virus promoter, e.g., human cytomegalovirus promoter DNA.

The DNA encoding a leader peptide which enables secretion of a prokaryotic protein sequence from a mammalian cell is any DNA encoding any suitable leader for this purpose such as DNA encoding a eukaryotic, preferably mammalian, leader sequence; for instance, DNA encoding a leader peptide of a peptide hormone, or, for example, of insulin, renin, Factor VIII, TPA, and the like, with DNA encoding human tissue plasminogen activator (TPA) leader peptide being presently preferred.

The human cytomegalovirus promoter can be an immediate early human cytomegalovirus promoter such as HCMV-IE. As to HCMV promoters, reference is made to U.S. Pat. Nos. 5,168,062 and 5,385,839. The plasmid of the invention can contain the HCMV-IE gene 5' untranslated region (UTR) which includes Intron A. This sequence can be 3' to the HCMV-IE promoter and 5' to the activator portion of the 5' UTR sequence and leader peptide. The TPA sequence can be derived from the TPA gene and can encode a portion of the 5' UTR and leader peptide from that gene. The 5' UTR of TPA may increase eukaryotic cell expression.

The transcriptional terminator sequence can be any suitable terminator, such as a eukaryotic terminator, for instance, DNA encoding a terminator for a mammalian peptide, with the BGH terminator being presently preferred.

The plasmid can be in admixture with any suitable carrier, diluent or excipient such as sterile water, physiological saline, and the like. Of course, the carrier, diluent or excipient should not disrupt or damage the plasmid DNA.

The plasmid can be administered in any suitable manner. The plasmid can be in a composition suitable for the manner of administration. The compositions can include: liquid preparations for orifice, e.g., oral, nasal, anal, vaginal, peroral, intragastric administration and the like, such as solutions, suspensions, syrups, elixirs; and liquid preparations for parenteral, subcutaneous, intradermal, intramuscular, intravenous administration, and the like, such as sterile solutions, suspensions or emulsions, e.g., for administration by injection. Intramuscular administration and compositions therefor are presently preferred.

The plasmids of the invention can be used for in vitro expression of antigens by eukaryotic cells. Recovery of such antigens can be by any suitable techniques; for instance, techniques analogous to the recovery techniques employed in the documents cited herein (such as the applications cited under Related Applications and the documents cited therein).

The thus expressed antigens can be used in immunological, antigenic or vaccine compositions, with or without an immunogenicity-enhancing adjuvant ("expressed antigen compositions"). Such compositions can be administered in dosages and by techniques well known to those skilled in the medical or veterinary arts taking into consideration such factors as age, sex, weight, species, condition of the particular patient, and the route of administration. These compositions can be administered alone or with other compositions, and can be sequentially administered, e.g., each spring as the "Lyme Disease season" is about to begin.

The route of administration for the expressed antigen compositions can be oral, nasal, anal, vaginal, peroral, intragastric, parenteral, subcutaneous, intradermal, intramuscular, intravenous, and the like.

The expressed antigen compositions can be solutions, suspensions, emulsions, syrups, elixirs, capsules (including "gelcaps"—a gelatin capsule containing a liquid antigen or fragment thereof—preparations), tablets, hard-candy-like preparations, and the like. The expressed antigen compositions may contain a suitable carrier, diluent, or excipient such as sterile water, physiological saline, glucose or the like. The compositions can also be lyophilised. The compositions can contain auxiliary substances such as wetting or emulsifying agents, pH buffering agents, adjuvants, gelling or viscosity enhancing additives, preservatives, flavouring agents, colours, and the like, depending upon the route of administration and the preparation desired. Standard texts, such as Remington: The Science and Practice of Pharmacy, $19^{th}$ ed., Gennaro, A R, 1995, incorporated herein by reference, may be consulted to prepare suitable preparations, without undue experimentation.

Suitable dosages for plasmid compositions and for expressed antigen compositions can also be based upon the examples below, and upon the documents cited herein. For example, suitable dosages can be in the range of 1–1000 $\mu$g, such as between 2 and 750 $\mu$g, between 5 and 500 $\mu$g, between 7.5 and 250 $\mu$g, between 10 and 150 $\mu$g, between 10 and 100 $\mu$g, between 10 and 75 $\mu$g, and between 10 and 50 $\mu$g, in expressed antigen compositions. In plasmid compositions, the dosage should be a sufficient amount of plasmid to elicit a response analogous to the expressed antigen compositions; or expression analogous to dosages in expressed antigen compositions. For instance, suitable quantities of plasmid DNA in plasmid compositions can be 0.1 to 2 mg, preferably 1–10 $\mu$g.

Thus, in a broad sense, the invention further provides a method comprising administering a composition containing plasmid DNA including DNA encoding a P13 antigen or antigens, for expression of the antigen or antigens in vivo for eliciting an immunological, antigenic or vaccine (protective) response by a eukaryotic cell; or for ex vivo or in vitro expression (that is, the cell can be a cell of a host susceptible to Lyme Disease, i.e., the administration can be to a host susceptible to Lyme Disease such as a mammal, e.g., a human; or the cell can be an ex vivo or in vitro cell). The invention further provides a composition containing a P13 antigen or antigens from expression of the plasmid DNA by a eukaryotic cell, in vitro or ex vivo, and methods for administering such compositions to a host mammal susceptible to Lyme disease to elicit a response.

Since the methods can stimulate an immune or immunological response, the inventive methods can be used for merely stimulating an immune response (as opposed to also being a protective response) because the resulting antibodies (without protection) are nonetheless useful. From eliciting antibodies, by techniques well-known in the art, monoclonal antibodies can be prepared and the monoclonal antibodies can be employed in well known antibody binding assays, diagnostic kits or tests to determine the presence or absence of a P13 antigen or to determine whether an immune response to the bacteria has simply been stimulated. The monoclonal antibodies can also be employed in recovery or testing procedures, for instance, in immunoadsorption chromatography to recover or isolate a P13 antigen.

To prepare the inventive plasmids, the DNA therein is preferably ligated together to form a plasmid. For instance, the promoter, leader sequence, antigen and terminator DNA is preferably isolated, purified and ligated together in a 5' to 3' upstream to downstream orientation. A three-way ligation, as exemplified below, is presently preferred.

Nucleic Acid Hybridisation Embodiments

Also contemplated within the scope of the present invention is the use of the disclosed DNA as a hybridization probe. While particular examples are provided to illustrate such use, the following provides a general background for hybridization applications taking advantage of the disclosed nucleic acid sequences of the invention.

As mentioned, in certain aspects, the DNA sequence information provided by the invention allows for the preparation of relatively short DNA (or RNA) sequences having the ability to specifically hybridise to Bb gene sequences. In these aspects, nucleic acid probes of an appropriate length are prepared based on a consideration of the sequence, e.g., SEQ ID NO: 18, SEQ ID NO: 20 and SEQ ID NO: 22 or derived from flanking regions of these genes. The ability of such nucleic acid probes to specifically hybridise to the Bb gene sequences lend them particular utility in a variety of embodiments. Most importantly, the probes can be used in a variety of diagnostic assays for detecting the presence of pathogenic organisms in a given sample. However, either uses are envisioned, including the use of the sequence information for the preparation of mutant species primers, or primers for use in preparing other genetic constructs.

To provide certain of the advantages in accordance with the invention, the preferred nucleic acid sequence employed for hybridization studies or assays includes sequences that are complementary to at least a 10 to 40, or so, nucleotide stretch of the selected sequence, such as that shown in SEQ ID NO: 18, SEQ ID NO: 20 and SEQ ID NO: 22. A size of at least 10 nucleotides in length helps to ensure that the fragment will be of sufficient length to form a duplex molecule that is both stable and selective. Molecules having complementary sequences over stretches more than 10 bases in length are generally preferred, though, in order to increase stability and selectivity of the hybrid, and thereby improve the quality and degree of specific hybrid molecules obtained. Thus, one will generally prefer to design nucleic acid molecules having gene-complementary stretches of 15 to 20 nucleotides, or even longer where desired. Such fragments may be readily prepared by, for example, directly synthesising the fragment by chemical means, by application of nucleic acid reproduction technology, such as the PCR technology of U.S. Pat. No. 4,603,102, or by introducing selected sequences into recombinant vectors for recombinant production.

The present invention will find particular utility as the basis for diagnostic hybridization assays for detecting Bb-specific RNA or DNA in clinical samples. Exemplary clinical samples that can be used in the diagnosis of infections are thus any samples which could possibly include nucleic acid, including samples from tissue, blood, serum, urine or the like. A variety of tissue hybridization techniques and systems are known which can be used in connection with the hybridization aspects of the invention, including diagnostic assays such as those described in Falkow et al., U.S. Pat. No. 4,358,535.

Accordingly, the nucleotide sequences of the invention are important for their ability to selectively form duplex molecules with complementary stretches of Bb gene segments. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective and tolerate little, if any, mismatch between the probe and the template or target strand.

Of course, for some applications, for example where one desires to prepare mutants employing a mutant primer strand hybridised to an underlying template, less stringent hybridization conditions are called for in order to allow formation of the heteroduplex. In these circumstances, one would desire to employ conditions such as 0.15M–0.9M salt, at temperatures ranging from 20° C. to 55° C. In any case, it is generally appreciated that conditions can be rendered more stringent by the addition of increasing amounts of formamide which serves to destabilise the hybrid duplex in the same manner as increased temperature. Thus, hybridization conditions can be readily manipulated, and will thus generally be a method of choice depending on the desired results.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as alkaline phosphatase or peroxidase, instead of radioactive or other environmentally undesirable reagents. In the case of enzyme tags, calorimetric indicator substrates are known which are employed to provide a means visible to the human eye or spectrophotometrically to identify specific hybridization with pathogenic nucleic acid-containing samples. Luminescent substrates, which give off light upon enzymatic degradation, could also be employed and may provide increased sensitivity.

In general, it is envisioned that the hybridization probes described herein will be useful both as reagents in solution hybridization as well as in embodiments employing a solid phase. In embodiments involving a solid phase, the test DNA (or RNA) from suspected clinical samples, such as exudates, body fluids (e.g., amniotic fluid, cerebrospinal fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridised surface so as to remove non-specifically bound probe molecules, specific hybridization is detected, or even quantified, by means of the label.

Furthermore, it is envisioned that synthetic single stranded nucleotides can be produced (by a series of photolitograpic and chemical steps) on a solid phase based on nucleic acid sequences or the complementary sequence of the invention and sequences comprised thereof. Single-stranded nucleic acid fragments from suspected clinical samples, such as exudates, body fluids (e.g., amniotic fluid, cerebrospinal fluid) or even tissues are then subjected to specific hybridisation under desired conditions. These single-stranded nucleic acid fragments are labeled for detection prior to hybridisation. The selected conditions for hybridisation will depend on the particular circumstances based on the particular criteria required (depending, for example, on the G+C content, type of target nucleic acid, source of nucleic acid, size of hybridization probe, etc.). Following washing of the hybridised surface so as to remove non-specifically bound probe molecules, specific hybridization is detected, or even quantified, by means of the label.

The invention discloses a DNA segment encoding an antigenic Bb protein. Detection of that DNA or various parts thereof is expected to provide the basis for a useful amplification assay. One method of detecting the P13 antigen genes is based on selective amplification of known portions of the gene. A particular method utilises PCR amplification, using any one of a number of primers that could be prepared from knowledge of the nucleic acid sequence of SEQ ID NO: 18, SEQ ID NO: 20 and SEQ ID NO: 22. Generally, such primers are relatively short, e.g., 7–28 base pairs in length, and may be derived from the respective sense or anti-sense strands of the disclosed DNA segment. Synthesis of these primers may utilise standard phosphoramidite chemistry (Beaucage et al., 1981).

In summary, this part of the invention relates to a diagnostic composition adapted for the determination of *Borrelia burgdorferi sensu lato* in a sample, the composition comprising an amount of the nucleic acid fragment of the invention which is effective to detectably bind to a nucleic acid fragment from *Borrelia burgdofferi sensu lato* present in the sample, the composition optionally comprising a detectable label.

Further, another embodiment of the invention is a method of determining the presence of *Borrelia burgdorferi sensu lato* nucleic acids in a sample, comprising incubating the sample with the nucleic acid fragment of the invention, and detecting the presence of hybridized nucleic acids resulting from the incubation. Alternatively, such a method comprises subjecting the nucleic acid fragment of the invention to a molecular amplification reaction, such as PCR, and detecting the presence of amplified nucleic acid which is specific for *Borrelia burgdorferi sensu lato*.

Finally, the invention also provides a diagnostic kit comprising a nucleic acid fragment of the invention and a means for detecting the binding between the nucleic acid fragment and nucleic acid bound thereto, or a set of nucleic acid primers which, when used in a molecular amplification procedure together with the nucleic acid fragment of the invention, will result in specific amplification of said nucleic acid fragment, and a means for detecting the amplified nucleic acid fragment.

Diagnostic Immunological Embodiments

Antibodies could be produced and used for screening strains for protein expression, for determining structural location and for examining bactericidal activity of antibodies against these proteins. Means and measures for producing both monoclonal and polyclonal antibodies against P13 are easily applied by the skilled person on the basis of the teachings herein.

It is contemplated that several assays for Lyme disease may be developed using any of the P13 proteins or its epitopes, the corresponding DNA encoding the protein, functionally similar proteins and their epitopes, or by detection of the appropriate mRNA. An indirect ELISA assay could be used with the P13 protein or other antigenic proteins. These methods are similar in principle to those previously described (Magnarelli et al., 1989; Craft et al., 1984; Bergström et al., 1991). Reactive epitopes representing portions of the P13 protein sequences could be utilised in an analogous manner.

Another promising assay is the microcapsule agglutination technique (MCAT) (Arimitsu et al., 1991). In this procedure, microscopic polystyrene beads are coated with Bb antigen and incubated with dilutions of patient serum. After overnight incubation at 4° C., the agglutination patterns are determined. Using whole Bb as antigen, the MCAT has been shown to be highly discriminatory between Lyme disease patients and healthy individuals, with little overlap in agglutination titre, although false positive reactions have been obtained with rheumatoid arthritis patients (Anderson et al., 1988) and leptospirosis samples (Barbour, 1988) An assay using P13 protein alone or in combination with other antigens such as the 94 kDa, 30 kDa and 21 kDa antigens should be feasible. Such a combination may increase sensitivity of the assay.

In summary, an embodiment of this part of the invention is a diagnostic composition adapted for the determination of Borrelia burgdorferi sensu lato in a sample, the composition comprising the polypeptide of the invention or prepared thereby, the amount of the polypeptide being effective to detectably react with antibodies present in the sample, the antibodies being directed against *Borrelia burgdorferi sensu lato*, the composition optionally comprising a detectable label, e.g. as described above. Related to this is another embodiment of the invention, i.e. a method of determining the presence of antibodies directed against *Borrelia burgdorferi sensu lato* in a sample, comprising incubating the sample with the polypeptide of the invention or prepared by the method of the invention, and detecting the presence of bound antibody resulting from the administration or incubation.

Finally, this part of the invention also pertains to a diagnostic kit comprising a polypeptide of the invention and a means for detecting the polypeptide with antibody bound thereto.

EXAMPLES

Bacterial strains and culture conditions. Borrelia strains used in this study were the following: strain B31 of *B. burgdorferi*, a tick isolate from North America (ATCC 35210); strain ACAI of *B. afzelii*, a human skin isolate from Sweden (Åsbrink et al., 1984); strain IP90 of *B. grainii*, a tick isolate from the Asian Russia (Kryuchechnikov et al., 1988); strain *B. burgdorferi* B313, a mutant of *B. burgdorferi* B31 lacking OspA, OspB, OspC and OspD (Sadziene et al., 1993).

Also used were three relapsing fever borreliae species, *B. hermsii, B. crocidurae,* and *B. hispanica,* as well as *B. anserina,* the causative agent of avian borreliosis.

Borreliae were grown in BSK II medium (Barbour, 1984) and the cells were harvested in late-log phase by centrifugation at 5,000 rpm for 20 min.

The *Escherichia coli* strains DH5α and BL21 were used for transformation with the recombinant plasmids in DNA cloning and gene expression experiments, respectively. *E. coli* strains were grown in Luria broth medium (Gibco BRL, Gaithersburg, Md.) supplemented, when required, with carbenicillin (Sigma, St. Louis, Mo.) at 50 µg/ml.

Monoclonal antibodies 15G6 and 7D4 were obtained from Dr. Alan G. Barbour (Sadziene et al., 1994)

DNA fragments were sequenced by the dideoxy chain termination method, with ABI PRISM™ Dye Terminator Cycle Sequencing Ready Reaction Kit, with AmpliTaq® DNA Polymerase, FS. The sequence fragments were assembled using the GCG software for UNIX computer.

Example 1

Preparation of Bb Proteins, Sodium Dodecyl Sulphate-polyacrylamide Gel Electrophoresis (SDS-PAGE), and Western Blot 1.1 Preparation of Bb Proteins For the whole-cell protein preparations, bacteria harvested from 250 ml of BSK II medium were washed twice with phosphate-buffered saline-5mM $MgCl_2$ (PBS-Mg). The pellet was suspended in 2 ml of PBS, sonicated and the supernatant was collected after centrifugation at 10,000 rpm for 30 min.

The subcellular fraction of borreliae outer membrane components (designated Fraction B) was prepared as described elsewhere (WO 90/04411). Briefly, cells harvested from 1.5l of the culture were washed three times with 10 mM Tris-HCl (pH 7.4), 150 mM NaCl and 5 mM $MgCl_2$ (TSM buffer). Octyl-β-D-glucopyranoside (OGP) (Sigma St. Louis, Mo.) was added to a final concentration of 2% in 10 ml TSM buffer and the suspension was incubated at 37° C. for 60 min. The cell lysate was centrifuged and the supernatant was incubated at 56° C. for 30 min. The precipitate was removed by centrifugation at 20,000 rpm for 30 min at 37° C., and the supernatant was dialysed against water at 4° C. for 2 days. The precipitate (Fraction B) formed in the dialysis bag was recovered by centrifugation at 20,000 rpm for 30 min at 25° C.

1.2 Separation of Proteins by SDS-PAGE

Bacterial proteins were separated by 15% SDS-PAGE essentially according to Laemmli (1970). Subsequently, gels were either stained with Coomassie Blue R-250 (CB) (Sigma, St Louis, Mo.), silver-staining (BioRad Hercules, Calif.), or were subjected to Western blotting.

1.3 Western Blotting

The proteins were transferred to a PVDF-membrane (BioRad, Hercules, Calif.) by electro-blotting at 0.8 $mA/cm^2$ for 1 h. The non-specific binding was blocked by immersing the filter for 2 h into 5% non-fat milk powder (Semper, Stockholm, Sweden) in PBS containing 0.05% Tween-20 (PBS-T). Primary or secondary antibodies were diluted with 2.5% milk-powder in PBS-T, and both incubations of the filter for 1 h were followed by washing in PBS-T. In a developing reaction the substrate for the alkaline phosphatase conjugate was 5-bromo4-chloro-3-indolyl phosphate (BCIP) (Sigma, St. Louis, Mo.).

Example 2

Preparation of Antiserum against the 13 kDa Antigen 2.1 Purification of the 13 kDa Antigen A 13 kDa protein was purified by 15% SDS-PAGE of Fraction B obtained from the *B. burgdorferi* B313 spirochaetes. The appropriate band was visualised by staining the gel with 250 mM KCl in ice-cold water without fixation in MeOH and acetic acid. Elution of 30 protein from the gel was performed in a Schleicher and Schuell Biotrap in 15 mM $NH_4HCO_3$ (200V for 8 hr).

2.2 Immunisation of Rabbits

A mixture of eluted protein and protein from a crushed SDS-PAGE gel of approximately 100 μg of the 13 kDa protein prepared as described above was homogenised and used in each of four immunisations of one rabbit performed at one and two (for the last immunisation) months intervals. Serum samples were obtained during a 5-month period, and serum was diluted 1:1,000 when used for Western blot analysis.

Example 3

Cell Surface Proteolysis of Borrelia Cells 3.1 Protease Treatment of Borrelia Cells Cell surface proteolysis of Bb cells was conducted as previously described (Barbour et al., 1984). Briefly, washed spirochetes were resuspended in PBS-Mg at a concentration of $2\times10^9$ cells/ml. To 950 μl of the cell suspension was added 50 μl of one of the following: distilled water, proteinase K (Sigma, St Louis, Mo.) (4 mg/ml in water) or trypsin (Gibco BRL, Gaithersburg, Md.) (1 mg/ml in $10^{-3}$ M HCl). After incubation for 40 min at 20° C., the proteolytic treatment was stopped by the addition of 10 μl from a solution of the peptidase inhibitor phenylmethylsulfonyl fluoride (PMSF) (Sigma, St. Louis, Mo.) (50 mg of PMSF per 1 ml of isopropanol), and the cells were centrifuged and washed twice with PBS-Mg. The pellets were resuspended in TSM buffer. One-third of the cell suspension of each preparation was subjected to the whole cell protein extraction by boiling in SDS-PAGE sample buffer. The remaining part of the suspensions was used to prepare the subcellular fraction of the borrelial outer membrane components, Fraction B, as described above.

3.2 Analysis of the Protease Treated Borrelia Cells

20 The result of the protease treatment of Bb cells as analysed by SDS-PAGE is presented in FIG. 1A, and followed by Western Blot, FIG. 1B. As seen in the CB stained protein profiles of the whole-cell lysates (FIG. 1A), proteinase K considerably affected the minor protein with an apparent molecular weight of 13 kDa. The protein composition of the subcellular fractions of outer membrane components (Fraction B) recovered from protease treated and untreated spirochaetes, was also investigated. The 13 kDa protein was shown to constitute a substantial part of the Fraction B obtained from the Bb cells. In the Fraction B derived from the proteinase K treated cells, the 13 kDa protein was entirely absent.

The finding that protease treatment eliminates the 13 kDa protein clearly shows that the 13 kDa protein is surface exposed, and most probably associated with the outer membrane of the Bb cells.

Example 4

Immunogold Labelling of Borrelia Cells

The monoclonal antibody 15G6 raised against the 13 kDa protein was used as the primary antibody for immunogold staining of intact *B. burgdorferi* B31 and *B. burgdorferi* B313. Cells from strain B31 (FIG. 2A) were labelled to a minor extent than cells from the strain B313 (FIG. 2B). This was probably due to the presence of outer surface proteins, i.e. OspA, OspB, OspC, OspD, on the surface of the B31 cells. The labelling was confined to the outer surface membrane for both strains indicating that the 13 kDa protein is an outer surface protein.

Example 5

Expression of the 13 kDa Protein in Different Borrelia Species 5.1 SDS-PAGE Analysis The CB stained SDS-PAGE of the whole-cell protein preparations of Lyme disease borreliae is shown in FIG. 1A. The 13 kDa protein was present in the whole-cell preparations (WC) and enriched in the membrane fraction (BF) of *B. burgdorferi* B31, *B. afzelii* ACAI, and *B. grainii* IP90. The PAGE revealed no major differences among the borrelial strains in respect of either apparent molecular weight or expression level of the 13 kDa protein. In the analogous preparations from *B. hermsii*, *B. crocidurae* and *B. anserina*, no visible band corresponding to the 13 kDa protein was detectable.

5.2 Western Blotting

In Western blot analysis of Fraction B prepared from *B. burgdorferi* B31, *B. afzelii* ACAI and *B. grainii* IP90 (FIGS. 3A and 3B), the 13 kDa protein of *B. burgdorferi* B31 reacted with the monoclonal antibody 15G6. The monoclonal antibody failed to recognise the 13 kDa protein from *B. afzelii* ACAI, and *B. grainii* IP90 indicating that the antibody is directed against a variable epitope.

However, polyclonal rabbit antiserum (described in Example 2.2) was able to recognise the 13 kDa protein from all three Lyme Disease species, i.e. *B. burgdorferi* B31, *B. afzelii* ACAI and *B. grainii* IP90 (FIG. 1B).

In another Western blot analysis the rabbit antiserum raised against the 13 kDa protein prepared from *B. burgdorferi* B313 did not recognise a 13 kDa protein or any proteins of similar molecular weight from *B. hermsii* or *B. crocidurae* (FIG. 1C), or *B. anserina* or *B. hispanica* (data not shown).

These data indicate that 13 kDa protein is unique for Lyme disease borreliae. Conversely, it was shown recently that the ospC gene homologues and OspC-related proteins are present in Borrelia species not associated with Lyme borreliosis (Marconi et al., 1993).

Example 6

Isolation and N-terminal Amino Acid Sequencing of the 13 kDa Protein 6.1 Amino Acid Sequencing The 13 kDa protein band was isolated and cut from a SDS-PAGE gel and eluted in a Biotrap as described above, Example 2.1. N-terminal amino acid sequencing of the purified 13 kDa protein was attempted but no sequence was obtained. It was concluded that the N-terminus of the 13 kDa protein was blocked. Therefore, the purified protein was digested with *Staphylococcus aureus* V8 protease. The protein cleavage resulted in two fragments of about equal size. As one of the fragments is blocked, only one can be sequenced. After cleavage the fragments were transferred to a PVDF membrane (Biorad, Hercules, Calif.) by soaking the membrane in the protein solution over night. N-terminal amino acid sequence analysis was performed on a 477A sequenator (Applied Biosystems, Foster City, Calif.) at Umeå University N-terminal amino acid sequence of the peptide fragment obtained by protease cleavage of the 13 kDa protein, recovered from the Fraction B of *B. burgdorferi* B313, resulted in the following sequence

TSKQDPIVPFLLNLFLGFGIGSFAQ (SEQ ID NO: 1)

6.2 Design of Oligonucleotide Probe

The sequence of the 25 amino acid fragment was used to design two oligonucleotides, one designated Y5.2 (SEQ ID NO: 2), and one designated Y6.2 (SEQ ID NO: 3). Codons for the amino acid sequence obtained, SEQ ID NO: 1, were selected by reverse translation based on (1) conclusion that codons containing A or T were favoured and (2) knowledge of published DNA sequences for several Bb proteins. A choice favouring A or T containing codons was based on the observation that the G+C content of Bb is only 28–35% (Burman et al., 1990). These oligonucleotides were used in a PCR reaction with DNA prepared from *B. burgdorferi* B31 as template and a 74 bp fragment was obtained. The PCR fragment was cloned into the T-vector (Novagen, Madison, Wis.) and sequenced, SEQ ID NO: 4. It was verified that the obtained PCR fragment coded for the N-terminal amino acid sequence of the peptide fragment obtained after protease cleavage of the 13 kDa protein, SEQ ID NO: 1. Based on the sequence of the PCR fragment an oligonucleotide designated Y7 (SEQ ID NO: 5) was designed. This oligonucleotide was to be used as a probe.

Example 7

Preparation of Bb DNA Libraries 7.1 Extraction of DNA

Spirochetes harvested from 400 ml of culture of *B. burgdofferi* B31, *B. burgdorferi* B313, *B. afzelii* ACAI, and *B. grainii* IP90 were washed twice with 50 mM Tris-HCl (pH=7.4) and resuspended in 10 ml of buffer containing 50 mM Tris-HCl (pH=7.4), 25% sucrose, and 50 mM EDTA. The cells were lysed by adding SDS to a final concentration of 2%, lysozyme (Sigma, St. Louis, Mo.) (1.5 mg/ml), proteinase K (Sigma, St. Louis, Mo.) (0.1 mg/ml), and RNAase A (Sigma, St Louis, Mo.) (10 pg/ml). The DNA was extracted with buffered phenol and ethanol precipitated.

7.2 Construction of DNA Libraries

Restriction enzymes were obtained from Boehringer, Mannheim, Germany. 100 ng of borrelial DNA prepared as described above was completely or partially digested using EcoRI and XbaI restriction endonucleases separately. For the partial digestions, 1 U of restriction endonuclease was incubated with 100 ng of DNA for 10 min. at 37° C. Twenty nanograms of appropriately digested pUC19 (Pharmacia, Uppsala, Sweden) vector was used for ligations.

Example 8

Cloning and Sequencing of the Gene Encoding the 13 kDa Protein 8.1 Screening of a DNA Library Prepared from *B. burgdodferi*

The recombinant plasmids were transformed into competent *E. coli* DH5α cells. Initially, a *B. burgdorferi* B31 and B313 EcoRI digested DNA library was screened with the DNA probe Y7 (SEQ ID NO: 5). This screening did not result in any positive clones.

An RsaI restriction site was identified in the sequence of the PCR fragment, SEQ ID NO: 4. This site was used in a further attempt to clone the gene encoding the 13 kDa protein as described below. DNA prepared from *B. burgdorferi* B31 was cut with RsaI and the fragment ligated into HincII digested pUC18 (Pharmacia, Uppsala, Sweden) plasmid. The oligonucleotide designated Y7 corresponding to the sequence downstream of the RsaI site, SEQ ID NO: 5, was used together with pUC primers forward and reversed (Pharmacia, Uppsala, Sweden) in a PCR reaction to obtain a DNA fragment corresponding to the downstream part of the gene coding for the 13 kDa protein. Another oligonucleotide designated Y7R corresponding to the sequence upstream of the RsaI site, SEQ ID NO: 6, was constructed and used together with the pUC primers forward and revised in a a PCR reaction with EcoRI digested DNA as template to obtain a DNA fragment corresponding to the upstream part of the gene coding for the 13 kDa protein. However, the obtained total sequence coded for a protein with a calculated molecular weight of 7 kDa. This did not correspond to the expected molecular weight of the full-length DNA fragment coding for the 13 kDa protein.

Therefore, a new oligonucleotide designated Y9, SEQ ID NO: 7, was designed and used together with the oligonucleotide Y7R, SEQ ID NO: 6, to generate a new PCR fragment. This PCR fragment was used as a probe to screen a library of XbaI digested DNA prepared from B. burgdorferi B31 in an attempt to isolate a full-length DNA fragment encoding the 13 kDa protein.

A recombinant plasmid designated pLY-100 recovered from one positive E. coli DH5α clone was isolated. The DNA insert of this plasmid was sequenced and found to comprise a gene fragment containing 537 bp including an ATG start codon followed by an open reading frame (ORF), SEQ ID NO: 18.

8.2 Sequencing of a Gene Encoding the 13 kDa Protein from B. afzelii ACAI and B. garinii* IP90.

The full-length 13 kDa protein gene was retrieved by PCR amplification followed by ligation into a pT7Blue vector (Novagen, Madison, Wis.). Multiple amplifications were used to ensure that the DNA Taq polymerase did not introduce any errors in the sequence.

The following primer pairs and number of clones was used to obtain the full-length and double stranded sequence of the gene encoding the 13 kDa protein in *B. afzelii* ACAI and *B. garinii* P90.

| # of *B. afzelii* ACAI clones[a] | Primer pairs[b] | Primer pairs[c] |
|---|---|---|
| 1 | Y9-Y18 | SEQ ID NO:7 - SEQ ID NO: 13 |
| 1 | Y9-CMV3 | SEQ ID NO:7 - SEQ ID NO: 17 |
| 1 | Y9-Y10 | SEQ ID NO:7 - SEQ ID NO:8 |
| 3 | Y12-Y10 | SEQ ID NO: 10 - SEQ ID NO:8 |
| 2 | Y13-CMV3 | SEQ ID NO: 11 - SEQ ID NO: 17 |

| # of *B. garinii* IP90 clones[a] | Primer pairs[b] | Primer pairs[c] |
|---|---|---|
| 2 | Y9-CMV2 | SEQ ID NO:7 - SEQ ID NO: 16 |
| 1 | Y12-Y10 | SEQ ID NO: 10 - SEQ ID NO:8 |
| 1 | Y11-Y10 | SEQ ID NO:9 - SEQ ID NO:8 |
| 1 | Y13-Y10 | SEQ ID NO: 11 - SEQ ID NO:8 |
| 3 | Y31-CMV2 | SEQ ID NO: 14 - SEQ ID NO: 16 |

[a]Clones obtained by different PCR amplifications
[b]Primer pairs used in different PCR amplifications
[c]Primer pairs used identified by SEQ ID numbers 8.3 Sequence Analysis Sequence analyses were performed using the University of Wisconsin GCG Sequence Analysis Software Version 7.2 for UNIX computer. Search in protein sequence databases was performed at the NCBI using the BLAST network service.

The nucleotide sequences of the gene encoding the 13 kDa protein of *B. burgdorferi* B31, *B. azelii* ACAI, *B. grainii* IP90, are shown in SEQ ID NO: 18, SEQ ID NO: 20, and SEQ ID NO: 22, respectively. The ATG start codon was followed by an ORF of 534 and 531 nucleotides for strains ACAI and IP90, respectively.

The nucleotide sequence of the gene encoding the 13 kDa protein of *B. burgdorferi* B313 was identical to the nucleotide sequence of the gene encoding the 13 kDa protein of *B. burgdorferi* B31.

The deduced amino acid sequences of the 13 kDa protein of *B. burgdorferi* B31, *B. afzelii* ACAI and *B. grainii* IP90 are presented in SEQ ID NO: 19, SEQ ID NO: 21 and SEQ ID NO: 23. The deduced amino acid sequences of the full-length protein consist of 179, 178 and 177 amino acids for the respective strain. The computer analysis predicted a potential leader peptidase 11 cleavage site between amino acid residues at position 12 and 13 (LXXF-C), and the N-terminal peak was found on the hydrophobicity plot (data not shown). Based on this and the fact that the protein was found to be N-terminally blocked, it could be concluded that the 13 kDa protein is a lipoprotein. However, no labelling of the 13 kDa protein with tritiated palmitate could be detected in Bb. This might be explained by the relatively early location of the cysteine, i.e., position 13. Usually the lipoprotein acylation sites are located within the first 16–30 amino acids. Further computer analysis predicted a potential signal peptidase I cleavage site between amino acids 21 and 22 in both *B. burgdorferi* B31 and *B. afzelii* ACAI, while two potential cleavage sites, between amino acids 19 and 20, and between amino acids 21 and 22, were identified in *B. garinii* IP90. Surprisingly, the full-length P13 protein from the strains B31, ACAI and IP90 consisted of, respectively, 179, 178 and 177 amino acids with a calculated molecular weight of 19107 Da, 19197 Da and 19311 Da. The cleavage of the respective leader sequences recognized by signal peptidase I would yield a mature P13 protein composed of: 158 amino acids with a calculated molecular mass of 16,772 Da for *B. burgdorferi* B31; 157 amino acids with a molecular mass of 16,864 for *B. afzelii* ACAI; and 156 or 158 amino acids with molecular masses of 16,872 Da or 17,115 Da, respectively for *B. garinii* IP90, in contrast to the apparent molecular weight of 13 kDa observed on PAGE. It therefore seems likely that P13 is both post-translationally processed and modified. Further analysis, such as determination of C-terminal amino acid and total amino acid composition of the purified P13 protein, will be necessary to finally establish the nature of this modification and processing.

The amino acid sequence of the P13 protein from *B. burgdorferi* B31 was 87.9% and 87.5% identical to the sequences from *B. afzelii* ACAI and *B. grainii* IP90, respectively. When compared with each other, the two latter strains showed 90.5% identity.

The level of similarity and identity between the deduced amino acid sequence of the P13 protein from different Borrelia strains further shows that this protein can be useful as a vaccine against Lyme disease as well as a target for diagnostic use.

The P13 proteins were examined for the sequence similarity to other known proteins in database libraries. There were no other sequences related significantly to the P13 proteins. The best hit in an EMBL database search was a 95 residues long amino acid sequence encoded by the p11 gene on the Bb 49 kb linear plasmid. The encoded amino acid sequence was 41.5% identical in sequence in a 82 amino acid overlap (corresponding to amino acid residues −12 to 70 in SEQ ID NO: 19). For the purposes of reference, this best hits are included herein as SEQ ID NOs: 30 and 31. The P13 gene sequence was compared to the recently completed *B. burgdorferi* B31 genome (Fraser et al., 1997) and was found to be identical with an ORF called BB034. Four additional Bb proteins with a high degree of sequence identity to P13 were also found. Together with these putative peptides denoted BBA01, BBI31, BBH41 and BBQO7, P13 belongs to a protein family designated paralogous family No. 5, formerly No. 48 (Fraser et al., 1997).

8.4 Antigenicity Plot

Potential antigenic regions of the deduced amino acid sequences of the P13 proteins from *B. burgdofferi* B31, *B. afzelii* ACAI and *B. grainii* IP90 were identified by calculation of the antigenic index using the algorithm of Jameson and Wolf (1988). The results are shown in FIG. 4. Proposed epitopic regions having a high antigenic index are e.g. the amino acid sequences corresponding to amino acid residues 19–27, 33–36, 41–47, 95–104, 138–147 and 174–179 in SEQ ID NO: 19; amino acid residues 19–26, 32–35, 40–47, 94–101, 137–146, and 174–178 in SEQ ID NO: 21; and amino acid residues 18–26, 30–33, 39–46, 91–104, 137–145 and 173–177 in SEQ ID NO: 23.

Example 9

Localisation of the P13 Protein Gene 9.1 Separation of DNA by Pulse-field Agarose Gel Electrophoresis For the pulse-field AGE, the DNA prepared from B. burgdorferi B31, B. burgdorferi B313, B. afzelii ACAI and B. grainii IP90 was recovered in 1% agarose blocks as previously described (Ferdows and Barbour, 1989). One-dimensional AGE and pulse-field AGE were performed in 1% agarose in TBE buffer. For the pulse-field AGE pulse times were 0.5 s for 30 min, 8 s for 30 min, 1 s for 3 h, 2 s for 3 h, 4 s for 6 h, 8 s for 8 h at a constant current of 200 V, see FIG. 5A.

9.2 Southern Blotting

Following depurination, denaturation and neutralisation of the gels, the DNA was transferred to a Hybond-N membrane (Amersham, Buckinghamshire, UK) by the method of Southern (Sambrook et al., 1989), and cross-linked with UV light. Filters were prehybridised and hybridised in 0.25 M Na2HPO4 (pH=7.2), 1% BSA, 1mM EDTA, 7% SDS for 1 h and 4 h, respectively, and washed for 15 min in 5×SSC, 0.1% SDS; followed by 15 min in 2×SSC, 0.1% SDS; and 15 in 1×SSC, 0.1% SDS, at the hybridisation temperature. The temperature was 60° C. for probing with a PCR fragment obtained by amplification using the primers Y7R (SEQ ID NO: 6) and Y9 (SEQ ID NO: 7) (see above) [$\alpha$-$^{32}$P]dATP (Amersham, Buckinghamshire, UK), radiolabeled by random primer technique.

The hybridising band corresponded to the position of the 1 Mbp linear chromosome of Lyme disease borreliae, see FIG. 5B.

Example 10

Existence of a P13 Homologue in Related Borrelia Species 10.1 DNA

Total DNA from B. burgdorferi, B. hermsii, B. crocidurae, and B. anserina was digested with EcoRI and separated by AGE.

10.2 Southern Blotting

Following depurination, denaturation and neutralisation of the gels, the DNA was transferred to a Hybond-N membrane (Amersham, Buckinghamshire, UK) by the method of Southern (Sambrook et al., 1989), and cross-linked with UV light. Filters were prehybridised and hybridised in 0.25 M Na2HPO4 (pH=7.2), 1% BSA, 1 mM EDTA, 7% SDS 40 for 1 h and 4 h, respectively, and washed for 15 min in 5×SSC, 0.1% SDS; followed by 15 min in 2×SSC, 0.1% SDS; and 15 in 1×SSC, 0.1% SDS, at the hybridisation temperature. The temperature was 55° C. for probing with a PCR fragment obtained by amplification using the primers Y9 (SEQ ID NO: 7) and Y7R (SEQ ID NO: 6) (see above) [$\alpha$-$^{32}$P]dATP (Amersham, Buckinghamshire, UK), radiolabeled by random primer technique.

There was no hybridization with either the DNA from the relapsing fever Borrelia species, B. hermsii, B. crocidurae, nor the avian borreliosis agent B. anserina (FIG. 6).

Furthermore, the P13 protein gene being localised to the chromosome of borreliae shows a higher degree of conservation among Lyme disease associated borreliae contrary to the plasmid-encoded major outer surface proteins A, B, and C which exhibit a significant species and strain dependent genetic and antigenic polymorphism (Barbour 1986, Jonsson et al., 1992, Wilske et al., 1993).

Example 11

Expression of the P13 Protein from B. burgdorferi B31 in E. coli 11.1 Expression of Full-length P13

Two oligonucleotide primers, Y14 (SEQ ID NO: 12) and Y33 (SEQ ID NO: 15), were designed to anneal to the 5' end containing the lipidation signal and the 3' end of the P13 gene from B. burgdorferi B31. The primers contained BamHI and EcoRI restriction sites, respectively, and were used to amplify the P13 gene in the PCR. PCR amplification was performed using Ampli-Taq DNA polymerase (Perkin Elmer Cetus, Norwalk, Conn.). The PCR product was then treated with the mentioned restriction enzymes, purified by AGE and ligated in fusion with GST (glutathione S-transferase) into the tac promoter based expression vector pGEX-2T (Pharmacia, Uppsala, Sweden). The recombinant plasmid, designated pLY31 3F, was then used to transform E. coli DH5a cells. E. coli DH5α cells containing the insert were grown and induced by adding isopropyl-β-D-thiogalactopyranoside (IPTG) (Sigma, St. Louis, Mo.) to a final concentration of 1 mM to express the introduced P13 gene. The P13 gene product was subsequently identified by SDS-PAGE (FIG. 7A) and Western blot with monoclonal antibody 15G6 against the P13 protein (FIG. 7B).

11.2 Expression of Truncated P13

A similar procedure was used to obtain a truncated variant, i.e. lacking the signal peptide. An oligonucleotide primer, Y13 (SEQ ID NO: 11), was designed to anneal to the 5' end without the lipidation signal sequence) of the P13 gene from B. burgdorferi B31. The primer also contains a BamHI restriction site. The primer was used together with the primer Y33 (SEQ ID NO: 15) in a PCR reaction to amplify the part of the P13 gene without the DNA sequence encoding the signal sequence. A recombinant plasmid designated pLY313T was prepared, E. coli transformed and grown as described above. The truncated P13 gene product was subsequently identified by SDS-PAGE (FIG. 7A) and Western blot with monoclonal antibody 15G6 against the P13 protein (FIG. 7B).

Example 12

DNA Vaccination 12.1 Preparation of DNA Constructs

To enable expression of B. burgdorferi B31 P13 in mammalian cells, the natural leader sequence of the P13 gene was replaced with the human tissue plasminogen activator (hTPA) leader sequence and cloned into the expression vector VR1020 (Luke et al., 1997) to yield plasmid pLY-H (FIG. 8A). A similar plasmid enabling the expression of B. burgdorferi B31 P13 in translational fusion with OspA was designed pLY-HA (FIG. 10B).

More specifically, the DNA encoding TPA 5' UTR and leader peptide, P13 and OspA were isolated from previous plasmid constructs or amplified. In pLY-H the TPA signal was isolated from VR2210 (Luke et al., 1997) by digestion with PstI/KpnI. The P13 gene was PCR amplified from pLY100 using the primers L1 (SEQ ID NO: 24) and L2 (SEQ ID NO: 25). The P13 containing fragment was digested with KpnI/XbaI and introduced together with the PstI/KpnI isolated TPA signal into VR1020 digested with PstI/XbaI.

In pLY-HA the TPA signal was PCR amplified with the primers L5 (SEQ ID NO: 28) and L6 (SEQ ID NO: 29). The P13 gene was PCR amplified from pLY100 using the primers L3 (SEQ ID NO: 26) and L4 (SEQ ID NO: 27) The PCR fragments were digested with the appropriate restriction enzymes. The OspA gene was isolated from VR2210 by digestion with KpnI/XbaI. All three fragments were combined in a three fragment ligation into the PstI/XbaI digested VR1020 to yield pLY-HA.

12.2 Vaccination of Mice

Mice will be injected with the plasmids pLY-h and pLY-HA as well as a negative control plasmid not containing a coding sequence for a Borrelia antigen. The plasmid and control DNA are diluted in standard saline. Three bilateral injections of DNA will be given at two week intervals at a dosage of 50 µg/leg into the rectus femoris muscle.

12.3 Analysis of Immune Response

Sera will be collected after each injection and analyzed by 1) antibody ELISA and 2) growth inhibition of spirochaetes.

12.4 Challenge with Bb Spirochaetes

After the last injection, mice will be challenged with *B. burgdorferi sensu stricto* N40 spirochaetes (same OspA serogroup as B31). Spirochetes will be either injected intradermally in the tail or by the tick challenge model (Telford et al., 1993). Mice will be sacrificed following the challenge. Bladder, heart, plasma, and cross-cuttings of the tibiotarsal joints will be cultured in growth medium. Cultures will be examined for the presence of spirochaetes by phase-contrast microscopy and scored as negative if no spirochaetes are seen in 50 high-power fields.

Example 13

Attempted Cloning of the P13 Gene Encoding the 13 kDa Protein Using Monoclonal Antibodies The clone pMG2 was obtained from Dr. Michael Norgard's laboratory. This clone had been isolated from a library prepared from partial Sau3AI digested DNA of *Borrelia burgdorferi* 297 cloned into the BamHI site of the plasmid pGEX-1 (Pharmacia). The library had been screened with the monoclonal antibody 15G6. After IPTG induction of *E. coli* DH5α cells transfected with the plasmid pMG2, a glutathione-*S-transferase* (GST) fusion protein reacting with the monoclonal antibody 15G6 could be seen in an immunoblot experiment. The fusion protein had a molecular weight of about 36 kDa, 26 kDa for the fusion partner GST plus 10 kDa for the Bb protein fragment.

According to restriction mapping, this clone contained an approximately 300 base pair insert. DNA sequencing showed an open reading frame of 251 bases. The insert was PCR amplified, oligolabelled, and used as a probe to screen libraries prepared from partial HindIII digested DNA from *B. burgdorferi* B31, *B. afzelii* ACAI, and *B. grainii* IP90, respectively.

Two positive clones were obtained from each Borrelia species and subsequently sequenced. A complete sequence determination was obtained from B31 and IP90 and a partial sequence was obtained from ACAL (first half of the gene). The nucleotide sequences were found to encode a 27 kDa protein in size which did not coincide with the expected size of the 13 kDa protein from Bb.

Furthermore, in another expression experiment the expression in *E. coli* of IPTG induced pMG2 and the above mentioned Bb derived clones was studied using the monoclonal antibody 7D4. After induction *E. coli* transfected with all clones as well as the negative control produced two proteins reacting with the antibody, about 36 kDa and 26 kDa in size. These results indicate that the monoclonal antibody 7D4 did not specifically recognise the 13 kDa Bb protein but cross-reacted with other proteins produced by the *E. coli* cells under these conditions.

Later the identified 27 kDa protein has been verified to be encoded by supercoiled plasmids of Bb (Porcella et al., 1996).

Example 14

Mass Spectrometry Analysis

Molecular weight determinations of P13 were performed on a VG Platform II mass spectrometer with a range of 2000 m/z equipped with an electrospray source (Micromass, Altrincham, UK). Prior to injection, the purified P13 preparation was precipitated with methanol:chloroform to remove any trace of SDS contamination. A P13 solution of 20 pmol/ml in water-acetonitrile (50:50 [vol/vol]) was mixed with 5% formic acid and introduced directly into the electrospray source at a flow rate of 5 ml/min. Calibration was performed by a separate introduction using horse heart myoglobin (16,951.5 Da). The MassLynx software was used to calculate the molecular weight.

The mass spectrometry analysis (FIG. 9) indicated a molecular weight of 13.9 kDa compared to the deduced molecular weight of the mature (cleaved) P13 protein of 16.8 kDa but in good agreement with the observed molecular weight of the mature P13 protein of 13 kDa as determined by gel-electrophoresis.

In addition, the whole molecule mass spectrum detected two minor peptide populations increased with 267 Da increments from the major peak. These peptides probably represent further modified subsets of P13. Two possible post-translational modifications can be considered to generate the mass change of 267 Da. Stearoylation gives an average mass change of 266.5 Da while the addition of two pentoses generates a mass change of 264.2 Da.

LIST OF REFERENCES

EP-B-0 036 776
EP-A-0 243 333
EP-A-0 366 238
WO 88/01875
WO 90/04411
U.S. Ser. No. 08/373,455
U.S. Pat. No. 3,791,932
U.S. Pat. No. 3,949,064
U.S. Pat. No. 4,174,384
U.S. Pat. No. 4,358,535
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,603,102
U.S. Pat. No. 4,608,251
U.S. Pat. No. 5,411,732
Adam T, Gassmann G S, Rasiah C, Göbel U B. 1991. Phenotypic and genotypic analysis of *Borrelia burgdorferi* isolates from various sources. Infection and Immunity, 59: 2579–2585.
Adelman J P, Hayflick J S, Vasser M, Seeburg P H. 1983. In vitro deletional mutagenesis for bacterial production of the 20,000-dalton form of human pituitary growth hormone. DNA. 2(3):183–93.

Anderson J F, Magnarelli L A, McAnich J B. 1988. Journal of Clinical Microbiology, 26: 2209–2212.

Arimitsu Y, Takashima I, Yoshii Z, Higashi Y, Kameyama S, Mizuguchi J. 1991. Journal of Infectious Diseases, 163: 682–683.

Baranton G, Postic D, Saint Girons I, Boerlin P, Piffaretti J-C, Assous M, Grimont PAD. 1992. Delineation of *Borrelia burgdorferi* sensu stricto, *Borrelia garinni* sp. nov., and group VS461 associated with Lyme borreliosis. International Journal of Systematic Bacteriology, 42: 378–383.

Barbour A G, Tessier S L, Hayes S F. 1984. Variation in a major surface protein of Lyme disease spirochaetes. Infection and Immunity, 45: 94–100.

Barbour A G. 1984. Immunochemical analysis of Lyme disease spirochaetes. The Yale Journal of Biology and Medicine, 57: 581–586.

Barbour A G. 1986. Polymorphisms of major surface proteins of *Borrelia burgdorferi*. Zbl Bakt Hyg, 263: 83–91.

Barbour A G. 1988. Laboratory aspects of Lyme borreliosis Clinical Microbiology Reviews, 1: 399–414.

Barthold S W, Bockenstedt L K. 1993. Passive immunising activity of sera from mice infected with *Borrelia burgdorferi*. Infection and Immunity, 61: 4696–4702.

Bergström S, Sjöstedt A, Dotevall L, Kaijser B, Ekstrand-Hammarström B, Wallberg C, Skogman G, Barbour A G. 1991. Diagnosis of Lyme borreliosis by an enzyme immunoassay detecting immunoglobulin G reactive to purified *Borrelia burgdorferi* cell components. European Journal of Clinical Microbiology and Infectious Diseases, 10: 422–427.

Beaucage S L, Caruthers M M et al., 1981. Tetrahedron Letters, 22: 1859–1862.

Bolivar F, Rodriguez R L, Greene P J, Betlach M C, Heyneker H L, Boyer H W. 1977. Construction and characterization of new cloning vehicles. II. A multipurpose cloning system. Gene, 2: 95–113.

Burgdorfer W, Barbour A G, Hayes S F, Benach J L, Grunwaldt E, Davis J P. 1983 Lyme disease—a tick borne spirochetosis? Science, 216: 1317–1319.

Burman N, Bergström S, Restrepo B I, Barbour A G. 1990. The variable antigens Vmp7 and Vmp21 of the relapsing fever bacterium *Borrelia hermsii* are structurally analogous to the VSG proteins of the African trypanosome. Molecular Microbiology, 4: 1715–1726.

Canica M M, Nato F, duMerle L, Mazie J C, Baranton G, Postic D. 1993. Monoclonal antibodies for identification of *Borrelia afzelii* sp. nov. associated with late cutaneous manifestations of Lyme borreliosis. Scandinavian Journal of Infectious Diseases, 25: 441–448.

Chang A C, Nunberg J H, Kaufman R J, Erlich H A, Schimke R T, Cohen S N. 1978. Phenotypic expression in *E. coli* of a DNA sequence coding for mousedihydrofolate reductase. Nature. 275(5681):617–24, Craft J E, Grodzicki R L, Steere A C. 1984. Antibody response in Lyme disease: evaluation of diagnostic tests. Journal of Infectious Diseases, 149: 789–795.

Crea R, Kraszewski A, Hirose T, Itakura K. 1978. Chemical synthesis of genes for human insulin. Proceedings of the National Academy of Sciences USA. 75(12):5765–5769.

Eichenlaub R. 1979. Mutants of the mini-F plasmid pML31 thermosensitive in replication. Journal of Bacteriology, 138: 559–566.

Erdile L F, Brandt M-N, Warakomski D J, Westrack G J, Sadziene A, Barbour A G, Mays J P. 1993. Role of attached lipid in immunogenicity of *Borrelia burgdorferi* OspA. Infection and Immunity, 61: 81–90.

Ferdows M S, Barbour A G. 1989. Megabase-sized linear DNA in the bacterium *Borrelia burgdorferi*, the Lyme disease agent. Proceedings of National Academy of Science, 86: 5969–5973.

Fiers W, Contreras R, Haegemann G, Rogiers R, Van de Voorde A, Van Heuverswyn H, Van Herreweghe J, Volckaert G, Ysebaert M. 1978. Complete nucleotide sequence of SV40 DNA. Nature. 273(5658):113–20.

Fikrig E, Barthold S W, Marcantonio N, DePonte K, Kantor F S, Flavell R A. 1992. Roles of OspA, OspB, and flagellin in protective immunity to Lyme borreliosis in laboratory mice. Infection and Immunity, 60: 657–661.

Fikrig E, Barthold S W, Persing D H, Sun X, Kantor F S, Flavell R A. 1992. *Borrelia burgdorferi* strain 25015: characterization of outer surface protein A and vaccination against infection. Journal of Immunology, 148: 2256–2260.

Fraser C M, Casjens S, Huang W M, Sutton G G, Clayton R, Lathigra R, White O, Ketchum K A, Dodson R, Hikey E K, Gwinn M, Doughery B, Tomb J F, Fleischmann R D, Richardson D, Peterson J, Kervalage A R, Quackenbush J, Salzberg S, Hanson M, van Vugt R, Palmer N, Adams M D, Gocayne J, Venter J C et al., 1997. Genomic sequence of a Lyme diseases spirochaete, *Borrelia burgdorferi*. Nature, 390: 580–586.

Goeddel D V, Heyneker H L, Hozumi T, Arentzen R, Itakura K, Yansura D G, Ross M J, Miozzari G, Crea R, Seeburg PH. 1979. Direct expression in *Escherichia coli* of a DNA sequence coding for human growth hormone. Nature. 281(5732):544–548.

Goodman J L, Jarkovich P, Kramber J M, Johnson R C. 1991. Molecular detection of persistent *Borrelia burgdorferi* in the urine of patients with active Lyme disease. Infection and Immunity, 59: 269–278.

Hess et al., 1968. Advances in Enzyme Regulation, 7: 149–166.

Hitzeman R A, Clarke L, Carbon J. 1980. Isolation and characterization of the yeast 3-phP13 oglycerokinase gene (PGK) by an immunological screeningtechnique. Journal of Biological Chemistry. 255(24):12073–12080.

Holland M J, Holland J P. 1978. Isolation and identification of yeast messenger ribonucleic acids coding for enolase, glyceraldehyde-3-phP13 ate dehydrogenase, and phP13 oglycerate kinase. Biochemistry. 17(23):4900–4907.

Honarvar N, Schaible U E, Galanos C, Wallich R ansd Simon M M. 1994. A 14,000 MW lipoprotein and a glycolipid-like structure of *Borrelia burgdorferi* induce proliferation and immunoglobulin production in mouse B cells at high frequencies. Immunology 82: 389–396.

Hopp T P, Woods K R. 1981. Proceedings of the National Academy of Sciences USA, 78:3824–3828.

Itakura K, Hirose T, Crea R, Riggs A D, Heyneker H L, Bolivar F, Boyer H W. 1977. Expression in *Escherichia coli* of a chemically synthesized gene for the hormone somatostatin. Science. 198(4321):1056–63, Jameson B A, Wolf H. 1988. Computer Applications in the biosciences, 4:181–186.

Jones E W. 1977. Proteinase mutants of *Saccharomyces cerevisiae*. Genetics, 85(1):23–33.

Jonsson M, Noppa L, Barbour A G, Bergström S. 1992. Heterogeneity of outer membrane proteins in *Borrelia burgdorferi*: comparison of osp operons of three isolates of different geographic origins. Infection and Immunity, 60: 1845–1853.

Katona L I, Beck G and Habicht G S. 1992. Purification and immunological characterization of a major low-molecular-weight lipoprotein from *Borrelia burgdorferi*. Infect. Immun., 60: 4995–5003.

Kingsman A J, Clarke L, Mortimer R K, Carbon J. 1979. Replication in *Saccharomyces cerevisiae* of plasmid pBR313 carrying DNA from the yeast trpI region. Gene. 7(2):141–52.

Kryuchechnikov V N, Korenberg E I, Scherbakov S V, Kovalevsky Y V, Levin M L. 1988. Identification of Borrelia isolated in the USSR from *Ixodes persulcatus schulze* ticks. Journal of Microbiology, Epidemiology and Immunobiology, 12: 41–44.

Kyte J, Doolittle R F. 1982. Journal of Molecular Biology, 157:105–132.

Laemmli U K. 1970. Nature 227:680–685

Lebech A M, Hindersson P, Vuust J, Hansen K J. 1991. Comparison of in vitro culture and polymerase chain reaction for detection of *Borrelia burgdorferi* in tissue from experimentally infected animals. Journal of Clinical Microbiology, 29: 731–737.

Luke C J, Carner K, Liang X, Barbour A G. 1997. An OspA-based DNA Vaccine protects mice against infection with *Borrelia burgdorferi*. The Journal of Infectious Diseases, 30 175:91–97.

Magnarelli L A., Anderson J F, Barbour A G. 1989. Enzyme-linked immunosorbent assays for Lyme disease: reactivity of subunits of *Borrelia burgdofferi*. Cross-reactivity in serologic tests for Lyme disease and other spirochetal infections. Journal of Infectious Diseases, 159: 43–49.

Marconi R T, Garon C F. 1992. Phylogenetic analysis of the genus Borrelia: a comparison of North American and European isolates of *Borrelia burgdorferi*. Journal of Bacteriology, 174: 241–244.

Marconi R T, Konkel M E, Garon C F. 1993. Variability of osp genes and gene products among species of Lyme disease spirochaetes. Infection and Immunity, 61: 2611–2617.

Marconi R T, Samuels D S, Schwan T G, Garon C F. 1993. Identification of a protein in several Borrelia species which is related to OspC of Lyme disease spirochaetes. Journal of Clinical Microbiology, 31: 2577–2583.

Matsudaira P. 1987. Sequence from picomole quantities of proteins electroblotted onto polyvinylidene difluoride membranes. Journal of Biological Chemistry, 262: 10035–10038.

Messing et al., 1981. Third Cleveland Symposium on Macromolecules and Recombinant DNA, Ed. A Walton, Elsevier, Amsterdam.

Nielsen P E, Egholm M, Berg R H, Buchardt O. 1991. Sequence-selective recognition of DNA by strand displacement with a thymine-substituted polyamide. Science, 254: 1497–1500.

Norris S J, Carter C J, Howell J K, Barbour A G. 1992. Low-passage-associated proteins of *Borrelia burgdorferi* B31: Characterization and molecular cloning of OspD, a surface exposed, plasmid-encoded lipoprotein. Infection and Immunity, 60: 4662–4672.

Norton Hughes C A, Engstrom S M, Coleman L A, Kodner C B, Johnson R C. 1993. Protective immunity is induced by a *Borrelia burgdofferi* mutant that lacks OspA and OspB. Infection and Immunity, 61: 5115–5122.

Porcella S F; Popova T G, Akins D R, Li M, Radolf J D, Norgard M V. 1996. *Borrelia burgdorferi* supercoiled plasmids encode multicopy tandem reading frames and a lipoprotein gene family. Journal of Bacteriology. 178: 3293–3307.

Rahn D W, Malavista S E. 1991. Annals of Internal Medicine, 114: 472–481.

Remington: The Science and Practice of Pharmacy, 19$^{th}$ ed., Gennaro, A R, 1995.

Rosa P A, Schwan T G. 1989. A specific and sensitive assay for the Lyme disease spirochaete *Borrelia burgdorferi* using the polymerase chain reaction. Journal of Infectious Diseases, 160:1018–1029.

Šadziene A, Thompson P A, Barbour A G. 1993. In vitro inhibition of *Borrelia burgdorferi* growth by antibodies. Journal of Infectious Diseases, 167: 165–172.

Šadziene A, Thomas D D and Barbour A G. 1994. *Borrelia burgdorferi* mutant lacking Osp: Biological and immunological characterization. Infection and Immunity, 63: 1573–1580.

Sambri V, Moroni A, Massaria F, Brocchi E, De Simone F and Cevenini R. 1991. Immunological characterization of a low molecular mass polypeptidic antigen of *Borrelia burgdorferi*. FEMS Microb. Immunol. 76: 345–350.

Sambrook J, Fritsch EF, Maniatis T. 1989. Molecular cloning: a laboratory manual, 2nd ed. Cold Spring Harbor Laboratory, Cold Spring Harbor, N.Y.

Schaible U E, Kramer M D, Eichmann K, Modolell M, Museteanu C, Simon M M. 1990. Monoclonal antibodies specific for the outer surface protein A (OspA) of *Borrelia burgdorferi* prevent Lyme borreliosis in severe combined immunodeficiency (scid) mice. Proceedings of the National Academy of Sciences USA 87: 3768–72.

Schmid G P. 1985. Reviews of infectious diseases, 7: 41–49.

Shanafelt M C, Hinderson P, Soderberg C, Mensi N, Turck C W, Webb D, Yssel H, Peltz G. 1991. T cell and antibody reactivity with the *Borrelia burgdorferi* 60-kDa heat shock protein in Lyme arthritis. Journal of Immunology, 146: 3985–3992.

Siebenlist U, Simpson R B, Gilbert W. 1980. *E. coli* RNA polymerase interacts homologously with two different promoters. Cell. 20(2):269–281.

Steere A C, Malavista S E, Syndman D R. 1977. Arthritis and reuhmatism, 20: 7–17.

Steere A C, Taylor E, Wilson M L, Levine J F, Spielman A. 1986. Journal of Infectious Diseases, 154: 295–300.

Stinchcomb D T, Struhl K, Davis R W. 1979. Isolation and characterisation of a yeast chromosomal replicator. Nature. 282(5734):39–43.

Telford S R, Fikrig E, Barthold S W, Rosa Brunet L, Spielman A, Flavell R A. 1993. Protection against antigenically variable *Borrelia burgdorferi* conferred by recombinant vaccines. Journal of Experimental Medicine, 178: 755–758.

Tschumper G, Carbon J. 1980. Sequence of a yeast DNA fragment containing a chromosomal replicator and the TRP1 gene. Gene. 10(2):157–66.

Ulmer J B, Donnelly J J, Parker S E, Rhodes G H, Feigner P L, Dwarki V J, Gromkowski S H, Deck R R, DeWitt C M, Friedman A. et al., 1993. Heterologous protection against influenza by injection of DNA encoding a viral protein. Science. 259(5102):1745–1749.

von Heijne G. 1986. A new method for predicting signal sequences cleavage sites. Nucleic Acid Research, 11: 4683–4690.

Wallich R, Moter S E, Simon M M, Ebnet K, Heiberger A, Kramer M D. 1990. The *Borrelia burgdorferi* flagellum-associated 41-kilodalton antigen (flagellin): molecular cloning, expression, and amplification of the gene. Infection and Immunity, 58: 1711–1719.

Wilske B, Preac-Mursic V, Jauris S, Hofman A, Pradel I, Soutschek E, Schwab E, Will G, Wanner G. 1993. Immunological and molecular polymorphisms of OspC, an immunodominant major outer surface protein of *Borrelia burgdorferi*. Infection and Immunity, 61: 2182–2191.

Zingg B C, Anderson J F, Johnson R C, LeFebvre R B. 1993. Comparative analysis of genetic variability among *Borrelia burgdorferi* isolates from Europe and the United States by restriction enzyme analysis, gene restriction fragment length polymorphism, and pulse-field gel electrophoresis. Journal of Clinical Microbiology, 31: 3115–3122.

Asbrink E, Hovmark A, Hederstedt B. 1984. The spirochetal etiology of acrodermatitis chronica atrophicans Herxheimer. Acta Dermatologica et Venereologica, 64: 506–512.

What is claimed is:

1. An isolated nucleic acid molecule which encodes a first polypeptide of SEQ ID NO: 19 or a second polypeptide which is at least one epitope of the first polypeptide, wherein the second polypeptide binds specifically in a western blot analysis with a rabbit polyclonal antibody raised against a third polypeptide having an apparent molecular weight of 13 kDa as determined by SDS-PAGE followed by visualization, wherein said third polypeptide is derived from *Borrelia burgdorferi* B313 and encoded by the nucleotide sequence of SEQ ID NO: 18, and wherein said rabbit polyclonal antibody does not bind specifically in a western blot analysis with proteins from at least 95% of spirochaetes randomly selected from the group consisting of *Borrelia hermsii, Borrelia crocidurae, Borrelia anserina,* and *Borrelia hispanica;* or hybridises readily under highly stringent hybridization conditions of 5–10° C. below the melting point ($T_m$) with SEQ ID NO: 18, or with a DNA molecule complementary thereto, but fails to readily hybridize under highly stringent hybridization conditions of 5–10° C. under the $T_m$ with genomic DNA from at least 95% of spirochaetes randomly selected from the group consisting of *Borrelia hermsii, Borrelia crocidurae, Borrelia anserina,* and *Borrelia hispanica;* or encodes a first polypeptide of SEQ ID NO: 19 or a second polypeptide which is at least one epitope of the first polypeptide, wherein the second polypeptide binds specifically in a western blot analysis with a rabbit polyclonal antibody raised against a third polpeptide having an apparent molecular weight of 13 kDa as determined by SDS-PAGE followed by visualization, said third polypeptide derived from *Borrelia burgdorferi* B313 and being encoded by the nucleotide sequence of SEQ ID NO: 18, and wherein said rabbit polyclonal antibody does not bind specifically in a western blot analysis with proteins from at least 95% of spirochaetes randomly selected from the group consisting of *Borrelia hermsii, Borrelia crocidurae, Borrelia anserina,* and *Borrelia hispanica;* and hybridises readily under highly stringent hybridization conditions of 5–10° C. below the $T_m$ with SEQ ID NO: 18, or with a DNA molecule complementary thereto, but fails to readily hybridize under highly stringent hybridization conditions of 5–10° C. under the $T_m$ with genomic DNA from at least 95% of spirochaetes randomly selected from the group consisting of *Borrelia hermsii, Borrelia crocidurae, Borrelia anserina,* and *Borrelia hispanica.*

2. The nucleic acid molecule according to claim 1, which encodes the second polypeptide, said second polpeptide being present in whole cell preparations of *Borrelia burgdorferi* B31, *Borrelia burgdorferi* B313, *Borrelia garinii* IP90, and/or *Borrelia afzelii* ACAI but being absent from whole cell preparations of at least 95% of randomly selected *Borrelia hermsii, Borrelia crocidurae, Borrelia anserina,* or *Borrelia hispanica.*

3. The nucleic acid molecule according claim 1, which encodes the third polypeptide having an apparent molecular weight of 13 kDa as determined by SDS-PAGE, said polypeptide being present in whole cell preparations of *Borrelia burgdorferi* B31, *Borrelia burgdorferi* B313, *Borrelia garinii* IP90, and/or *Borrelia afzelii* ACAI but being absent from whole cell preparations of at least 95% of randomly selected *Borrelia hermsii, Borrelia crocidurae, Borrelia anserina,* and *Borrelia hispanica.*

4. The nucleic acid molecule according to claim 1, which encodes a polypeptide comprising at least one epitope of the third polpeptide having an apparent molecular weight of 13 kDa as determined by SDS-PAGE, said third polypeptide being present in whole cell preparations of *Borrelia burgdorferi* B31, *Borrelia burgdorferi* B313, *Borrelia garinii* IP90, or *Borrelia afzelii* ACAI but being absent from whole cell preparations of at least 95% of randomly selected *Borrelia hermsii, Borrelia crocidurae, Borrelia anserina,* and *Borrelia hispanica.*

5. The nucleic acid molecule according to claim 1, which encodes a polypeptide which has an amino acid sequence exhibiting a sequence identity of at least 50% with SEQ ID NO: 19, SEQ ID NO: 21, or SEQ ID NO: 23, or with subsequences thereof having a length of at least 10 contiguous amino acid residues.

6. The nucleic acid molecule according to claim 1, wherein the nucleotide sequence has a sequence homology of at least 70% with SEQ ID NO: 18, or with subsequences thereof encoding a polypeptide of at least 10 contiguous amino acid residues.

7. The nucleic acid molecule according to claim 1, which comprises a nucleic acid molecule encoding a polypeptide which comprises at least one amino acid sequence selected from the group consisting of amino acid residues 19–27, 33–36, 41–47, 95–104, 138–147 and 174–179 in SEQ ID NO: 19; amino acid residues 19–26, 32–35, 40–47, 94–101, 137–146, and 174–178 in SEQ ID NO: 21; amino acid residues 18–26, 30–33, 39–46, 91–104, 137–145 and 173–177 in SEQ ID NO: 23.

8. The nucleic acid molecule according to claim 1 which comprises a nucleotide sequence encoding a polypeptide which includes an amino acid sequence selected from the group consisting of SEQ ID NOs: 19, 21, and 23.

9. The nucleic acid molecule according to claim 1, which comprises the nucleotide sequence of SEQ ID No: 18.

10. The nucleic acid molecule according to claim 1, which encodes a fusion polypeptide.

11. The nucleic acid molecule according to claim 1, which is a DNA molecule.

12. The diagnostic composition adapted for the determination of *Borrelia burgdorferi sensu lato* in a sample the composition comprising an amount of the nucleic acid according to claim 1 which is effective to detectably bind to a nucleic acid molecule from *Borrelia burgdorferi sensu lato* present in the sample, the composition optionally comprising a detectable label.

13. The diagnostic kit comprising
a nucleic acid molecule according to claim 1 and a means for detecting the binding between the nucleic acid molecule and nucleic acid bound thereto, or
a set of nucleic acid primers which, when used in a molecular amplification procedure together with the nucleic acid molecule, will result in specific amplification of said nucleic acid molecule, and a means for detecting the amplified nucleic acid molecule.

14. The nucleic acid molecule according to claim 3, wherein the encoded polypeptide is present in fraction B from *Borrelia burgdorferi* B31, *Borrelia burgdorferi* B313, *Borrelia garinii* IP90, or *Borrelia afzelii* ACAI.

15. The nucleic acid molecule according to claim 14, wherein the encoded protein is a surface exposed protein of *Borrelia burgdorferi* B31, *Borrelia burgdorferi* B313, *Borrelia garinii* IP90, or *Borrelia afzelii* ACAI.

16. The nucleic acid molecule according to claim 8 which consists of nucleotide sequence encoding a polpeptide consisting of an amino acid sequence selected from the group consisting of SEQ ID NOs: 19, 21, and 23.

17. The nucleic acid molecule according to claim 9, which consists of the nucleotide sequence of SEQ ID NO: 18.

18. The nucleic acid molecule according to claim 10, which encodes a fusion polypeptide which comprises, as a fusion partner, a polypeptide which enhances the immunogenicity of the fusion polypeptide relative to the immunogenicity of polypeptide not comprising said second fusion partner or which facilitates the expression of the fusion polypeptide in a host cell and/or the subsequent purification of the polypeptide.

19. The nucleic acid molecule according to claim 10, which encodes a fusion polypeptide comprising, as a fusion partner, a polypeptide which
has the same amino acid sequence as at least one amino acid sequence selected from the group consisting of amino acid residues 19–27, 33–36, 41–147, 95–104, 138–147 and 174–179 in SEQ ID NO: 19; amino acid residues 19–26, 32–35, 40–47, 94–101, 137–46, and 174–178 in SEQ ID NO: 21; and amino acid residues 18–26, 30–33, 39–46, 91–104, 137–145 and 173–177 in SEQ ID NO: 23,
is a lipoprotein selected from the outer membrane lipoprotein from *E. coli* and OspA from *Borrelia burgdorferi sensu lato,*
is a viral protein selected from Hepatitis B surface antigen, Hepatitis B core antigen, and the influenza virus non-structural protein NS1,
is an immunoglobulin binding protein selected from protein A, protein G, and the ZZ-peptide,
is a T-cell epitope,
is a B-cell epitope,
is a bacterial fimbrial protein selected from the pilus components pilin and papA. and/or
is the maltose binding protein, glutathione S-transferase, β-galactosidase, calmodulin binding protein or polyhistidine.

20. An isolated nucleic acid molecule that comprises SEQ ID NO: 18.

21. An isolated nucleic acid molecule that encodes SEQ ID NO: 19.

22. The nucleic acid molecule according to claim 21, which encodes a polypeptide which has an amino acid sequence exhibiting a sequence identity of at least 75% with SEQ ID NO: 19, SEQ ID NO: 21, or SEQ ID NO: 23, or with subsequences thereof having a length of at least 10 contiguous amino acid residues.

23. The nucleic acid molecule according to claim 22, which encodes a polypeptide which has an amino acid sequence exhibiting a sequence identity of a least 80% with SEQ ID NO: 19, SEQ ID NO: 21, or SEQ ID NO: 23, or with subsequences thereof having a length of at least 10 contiguous amino acid residues.

24. The nucleic acid molecule according to claim 23, which encodes a polypeptide which has an amino acid sequence exhibiting a sequence identity of at least 85% with SEQ ID NO: 19, SEQ ID NO: 21, or SEQ ID NO: 23, or with subsequences thereof having a length of at least 10 contiguous amino acid residues.

25. The nucleic acid molecule according to claim 24, which encodes a polypeptide which has an amino acid sequence exhibiting a sequence identity of at least 90% with SEQ ID NO: 19, SEQ ID NO: 21, or SEQ ID NO: 23, or with subsequences thereof having a length of at least 10 contiguous amino acid residues.

26. The nucleic acid molecule according to claim 25, which encodes a polypeptide which has an amino acid sequence exhibiting a sequence identity of at least 92% with SEQ ID NO: 19, SEQ ID NO: 21, or SEQ ID NO: 23, or with subsequences thereof having a length of at least 10 contiguous amino acid residues.

27. The nucleic acid molecule according to claim 26, which encodes a polypeptide which has an amino acid sequence exhibiting a sequence identity of at least 94% with SEQ ID NO: 19, SEQ ID NO: 21, or SEQ ID NO: 23, or with subsequences thereof having a length of at least 10 contiguous amino acid residues.

28. The nucleic acid molecule according to claim 27, which encodes a polypeptide which has an amino acid sequence exhibiting a sequence identity of at least 95% with SEQ ID NO: 19, SEQ ID NO: 21, or SEQ ID NO: 23, or with subsequences thereof having a length of at least 10 contiguous amino acid residues.

29. The nucleic acid molecule according to claim 28, which encodes a polypeptide which has an amino acid sequence exhibiting a sequence identity of at least 96% with SEQ ID NO: 19, SEQ ID NO: 21, or SEQ ID NO: 23, or with subsequences thereof having a length of at least 10 contiguous amino acid residues.

30. The nucleic acid molecule according to claim 6, wherein the nucleotide sequence has a sequence homology of at least 75% with SEQ ID NO: 18, or with subsequences thereof encoding a polypeptide of at least 10 contiguous amino acid residues.

31. The nucleic acid molecule according to claim 30, wherein the nucleotide sequence has a sequence homology of at least 80% with SEQ ID NO: 18, or with subsequences thereof encoding a polypeptide of at least 10 contiguous amino acid residues.

32. The nucleic acid molecule according to claim 31, wherein the nucleotide sequence has a sequence homology of at least 85% with SEQ ID NO: 18, or with subsequences thereof encoding a polypeptide of at least 10 contiguous amino acid residues.

33. The nucleic acid molecule according to claim 32, wherein the nucleotide sequence has a sequence homology of at least 87% with SEQ ID NO: 18, or with subsequences thereof encoding a polypeptide of at least 10 contiguous amino acid residues.

34. The nucleic acid molecule according to claim 33, wherein the nucleotide sequence has a sequence homology of at least 89% with SEQ ID NO: 18, or with subsequences thereof encoding a polypeptide of at least 10 contiguous amino acid residues.

35. The nucleic acid molecule according to claim 34, wherein the nucleotide sequence has a sequence homology of at least 90% with SEQ ID NO: 18, or with subsequences thereof encoding a polypeptide of at least 10 contiguous amino acid residues.

36. The nucleic acid molecule according to claim 35, wherein the nucleotide sequence has a sequence homology of at least 92% with SEQ ID NO: 18, or with subsequences thereof encoding a polypeptide of at least 10 contiguous amino acid residues.

37. The nucleic acid molecule according to claim 36, wherein the nucleotide sequence has a sequence homology of at least 94% with SEQ ID NO: 18, or with subsequences thereof encoding a polypeptide of at least 10 contiguous amino acid residues.

38. The nucleic acid molecule according to claim 37, wherein the nucleotide sequence has a sequence homology of at least 95% with SEQ ID NO: 18, or with subsequences thereof encoding a polypeptide of at least 10 contiguous amino acid residues.

* * * * *

UNITED STATES PATENT AND TRADEMARK OFFICE
CERTIFICATE OF CORRECTION

PATENT NO. : 6,610,838 B1
DATED : August 26, 2003
INVENTOR(S) : Sven Bergstrom

It is certified that error appears in the above-identified patent and that said Letters Patent is hereby corrected as shown below:

Title page,
Item [73], Assignee, change "Amea" to -- Umea --.

Column 64,
Line 18, change "said second polpeptide" to -- said second polypeptide --.
Line 25, change "according claim 1" to -- according to claim 1 --.

Signed and Sealed this

Seventeenth Day of February, 2004

JON W. DUDAS
*Acting Director of the United States Patent and Trademark Office*